United States Patent [19]

Androphy et al.

[11] Patent Number: 5,667,965

[45] Date of Patent: Sep. 16, 1997

[54] PAPILLOMAVIRUS E2 TRANS-ACTIVATION REPRESSORS

[75] Inventors: Elliot J. Androphy, Natick; James G. Barsoum, Lexington, both of Mass.

[73] Assignees: Biogen, Inc., Cambridge; New England Medical Center Hospitals, Inc., Boston, both of Mass.

[21] Appl. No.: 455,972

[22] Filed: May 31, 1995

Related U.S. Application Data

[60] Division of Ser. No. 94,128, Sep. 24, 1993, which is a continuation-in-part of Ser. No. 646,998, Jan. 28, 1991, Pat. No. 5,219,990.

[51] Int. Cl.$^6$ .............................. C12P 21/06; C12Q 1/70; C12N 7/00; C12N 7/02
[52] U.S. Cl. .......................... 435/5; 435/69.1; 435/235.1; 435/320.1; 536/23.72
[58] Field of Search ........................ 435/69.1, 5, 235.1, 435.239, 320.1, 240.1; 536/23.72

[56] References Cited

U.S. PATENT DOCUMENTS

| | | | |
|---|---|---|---|
| 4,777,239 | 10/1988 | Schoolnik et al. | 530/236 |
| 5,219,990 | 6/1993 | Androphy et al. | 530/350 |

FOREIGN PATENT DOCUMENTS

| | | |
|---|---|---|
| 0302758 | 8/1989 | European Pat. Off. . |
| WO 89/12461 | 12/1989 | WIPO . |

OTHER PUBLICATIONS

Aaronson, S.A. et al., "Development of 3T3-like Lines form Balb/c Mouse Embryo Cultures: Transformation Susceptibility to SV40", *J. Cell Physiol.*, 72, pp. 141–148 (1968).

Androphy, E.J. et al., "Bovine Papillomavirus E2-Trans-Activating Gene Product Binds to Specific Sites in Papillomavirus DNA", *Nature*, 325, pp. 70–73 (1987).

Barsoum, J., "Introduction of Stable High-Copy-Number DNA into Chinese Hamster Ovary Cells by Electroporation", *DNA Cell Biol.*, 9, pp. 293–300 (1990).

Barsoum, J. et al., "Mechanism of Action of the Papillomavirus E2 Repressor: Repression in the Absence of DNA Binding", *J. Virol.*, 66, pp. 3941–3945 (1992).

Cate, R.L. et al., "Isolation of the Bovine and Human Genes for Mullerian Inhibiting Substance and Expression of the Human Gene in Animal Cells", *Cell*, 45, pp. 685–698 (1986).

Chen, E.Y. et al., "The Primary Structure and Genetic Organization of the Bovine Papillomavirus Type 1 Genome", *Nature*, 299, pp. 529–534 (1982).

Chodosh, L.A., "Mobility Shift DNA–Binding Assay Using Gel Electrophoresis" in *Current Protocols in Molecular Biology*, pp. 12.2.1–12.2.10 (1990 F.M. Ausubel et al., eds.).

Choe, J, et al., "Bovine Papillomavirus Type 1 Encodes Two Forms of a Transcriptional Repressor: Structural and Functional Analysis of New Viral cDNAs", *J. Virol.*, 63, pp. 1743–1755 (1989).

Chu, G. et al., "Electroporation for the Efficient Transfection of Mammalian Cells with DNA", *Nuc. Acids Res.*, 15, pp. 1311–1326 (1987).

Dartmann, K. et al., "The Nucleotide Sequence and Genome Organization of Human Papilloma Virus Type 11", *Virology*, 151, pp. 124–130 (1986).

De Villiers, E.M., "Heterogeneity of the Human Papillomavirus Group", *J. Virol.*, 63, pp. 4898–4903 (1989).

Dostatni N., et al., "A Dimer of BPV–1 E2 Containing A Protease Resistant Core Interacts with its DNA Target", *EMBO J.*, 7, pp. 3807–3816 (1988).

Giri, I. et al., "Structural and Mutational Analysis of E2 Trans–Activating Proteins of Papillomaviruses Reveals Three Distinct Functional Domains", *EMBO J.*, 7, pp. 2823–2829 (1988a).

Giri, I. et al., "Study of the E2 Gene Product of the Cottontail Rabbit Papillomavirus Reveals a Common Mechanism of Transactivation Among Papillomaviruses", *J. Virol.*, 62, pp. 1573–1581 (1988b).

Gorman, C.M. et al., "Recombinant Genomes which Express Chloramphenicol Acetyltransferase in Mammalian Cells", *Mol. Cell. Biol.*, 2, pp. 1044–1051 (1982).

Haugen, T.H. et al., "Sequence–Specific and General Transcriptional Activation by the Bovine Papillomavirus–1 E2 trans–Activator Require an N–Terminal Amphipathic Helix–Containing E2 Domain", *EMBO J.*, 7, pp. 4245–4253 (1988).

Haugen, T.H. et al., "Trans–Activation of an Upstream Early Gene Promoter of Bovine Papillomavirus–1 by a Product of the Vital E2 Gene", *EMBO J.*, 6, pp. 145–242 (1987).

Hawley–Nelson, P. et al., "The Specific DNA Recognition Sequence of the Bovine Papillomavirus E2 Protein is an E2–Dependent Enhancer", *EMBO J.*, 7, pp. 525–531 (1988).

Hirochika, H. et al., "Enhancers and trans–Acting E2 Transcriptional Factors of Papillomaviruses", *J. Virol.*, 61, pp. 2599–2606 (1987).

Hirochika, H. et al., "Functional Mapping of the Human Papillomavirus Type 11 Transcriptional Enhancer and its Interaction with the trans–Acting E2 Proteins", *Genes Dev.*, 2, 54–67 (1988).

Hoffmann, P., et al., "Stimulation of Human and Murine Adherent Cells by Bacterial Lipoprotein and Synthetic Lipopeptide Analogues", *Immunobiology*, 177, pp. 158–170 (1988).

Kost, T.A. et al., "The Nucleotide Sequence of the Chick Cytoplasmic β–Actin Gene", *Nuc. Acids Res.*, 11, pp. 8287–8301 (1983).

Kunkel, T.A. et al., "Rapid and Efficient Site–Specific Mutagenesis Without Phenotypic Selection", *Meth. Enzymol.*, 154, pp. 367–382 (1987).

Lambert, P.F. et al., "Functional Analysis Of The Papilloma Virus E2 Trans–Activator In *Saccharomyces cerevisiae*", *Genes & Devel.*, 3, pp. 38–48 (1989).

Lambert, P.F. et al., "Phenotypic Analysis of Bovine Papillomavirus Type 1 E2 Repressor Mutants", *J. Virol.* 64, pp. 950–956 (1990).

Lambert, P.F. et al., "A Transcriptional Repressor Encoded by BPV–1 Shares a Common Carboxy–Terminal Domain with the E2 Transactivator", *Cell*, 50, pp. 69–78 (1987).

Lambert, P.F. et al., "Genetic Assignment of Multiple E2 Gene Products in Bovine Papillomavirus–Transformed Cells", *J. Virol.*, 63, pp. 3151–3154 (1989).

Li, R. et al., "Specific Recognition Nucleotides and Their DNA Context Determine the Affinity of E2 Protein for 17 Binding Sites in the BPV–1 Genome", *Genes Dev.*, pp. 510–526 (1989).

McBride A.A. and P.M. Howley, "Characterization Of The DNA Binding/Dimerization Domain Shared By The E2 Regulatory Proteins Of BPV–1" *J. Cell. Biochem.*, Supp.13C:191 (Abstract #I 135) (1989a).

McBride, A.A. et al., "E2 Polypeptides Encoded by Bovine Papillomavirus Type 1 Form Dimers through the Common Carboxyl–Terminal Domain: Transactivation is Mediated by the Conserved Amino–Terminal Domain", *Proc. Natl. Acad Sci. USA*, 86, pp. 510–514 (1989b).

McBride, A.A. et al., "Phosphorylation Sites of the E2 Transcriptional Regulatory Proteins of Bovine Papillomavirus Type 1", *J. Virol.* 63, pp. 5076–5085 (1989c).

McBride, A.A. et al., "Bovine Papillomavirus With A Mutation In The E2 Serine 301 Phosphorylation Site Replicates At A High Copy Number", *J. Virol.*, 65, pp. 528–534 (1991).

McBride, A.A. et al., "E2 Polypeptides Encoded by Bovine Papillomavirus Type 1 Form Dimers through the Cmmmon Carboxyl–Terminal Domain: Transactivation is Mediated by the Conserved Amino–Terminal Domain", *Proc. Natl. Acad Sci. USA*, 86, pp. 510–514 (1989).

McBride, A.A. et al., "The Carboxy–Terminal Domain Shared by the Bovine Papillomavirus E2 Transactivator and Repressor Proteins Contains a Specific DNA Binding Activity", *EMBO J.*, 7, pp. 533–539 (1988).

McKay, R.D.G., "Binding of a Simian Virus 40 T Antigen–Related Protein to DNA", *J. Mol. Biol.*, 145, pp. 471–488 (1981).

Merrifield R.B., "Solid Phase Peptide Synthesis. I. The Synthesis of a Tetrapeptide", *J. Am. Chem. Soc.*, 85, pp. 2149–2154 (1963).

Mohr, I.J. et al., "Targeting the E1 Replication Protein to the Papillomavirus Origin of Replication by Complex Formation with the E2 Transactivator", *Science*, 250, pp. 1694–1699 (1990).

Morrissey, L.C. et al., "Trans–Activation by the Bovine Papillomavirus E2 Protein in *Saccharomyces cerevisiae*", *J. Virol.*, 63, pp. 4422–4425 (1989).

Moskaluk, C. et al., "The E2 'Gene' of Bovine Papillomavirus Encodes an Enhancer Binding Protein", *Proc. Natl. Acad. Sci. USA*, 84, pp. 1215–1218 (1987).

Moskaluk, C. et al., "Interaction of the Bovine Papillomavirus Type 1 E2 Transcriptional Control Protein with the Viral Enhancer: Purification of the DNA–Binding Domain and Analysis of Its Contact Points with DNA", *J. Virol.*, 62, pp. 1925–1931 (1988a).

Moskaluk, C. et al., "DNA Bending is Induced in an Enhancer by the DNA–Binding Domain of the Bovine Papillomavirus E2 Protein", *Proc. Natl. Acad. Sci. USA*, 85, pp. 1826–1830 (1988b).

Moskaluk, C. et al., "The Bovine Papillomavirus Type 1 Transcriptional Activator E2 Protein Binds to Its DNA Recognition Sequence as a Dimer", *Virology*, 169, pp. 236–238 (1989).

Myers, R.M. et al., "A General Method for Saturation Mutagenesis of Cloned DNA Fragments", *Science*, 229, pp. 242–247 (1985).

Prakash, S.S. et al., "Amino Acids Necessary For DNA Contact And Dimerization Imply Novel Motifs In The Papillomavirus E2 Trans–Activator", *Genes and Devel.*, 6, pp. 105–116 (1992).

Seiler–Tuyns, A. et al., "Expression and Regulation of Chicken Actin Genes Introduced into Mouse Myogenic and Nonmyogenic Cells", *Proc. Natl. Acad. Sci.USA*, 81, pp. 2980–2984 (1984).

Selden, R.F., "Assay for Human Growth Hormone," in *Current Protocols in Molecular Biology*, pp. 9.7.1–9.7.3 (1990, F.M, Ausubel et el., eds,).

Shen, W.C. et al., "Conjugation of poly–L–lysine to Albumin and Horseradish Peroxidase: A Novel Method of Enhancing the Cellular Uptake of Proteins", *Proc. Natl. Acad. Sci. USA*, 75, pp. 1872–1876 (1978).

Sousa, R. et al., "Control of Papillomavirus Gene Expression", *Biochim. Biophys. Acta*, 1032, pp. 19–37 (1990).

Spalholz, B.A. et al., "Transactivation of a Bovine Papilloma Virus Transcriptional Regulatory Element by the E2 Gene Product", *Cell*, 42, pp. 183–191 (1985).

Spalholz, B.A. et al., "Bovine Papillomavirus Transcriptional Regulation: Localization of the E2–Responsive Elements of the Long Control Region", *J. Virol.*, 61, pp. 2128–2137 (1987).

Stenlund, A. et al. "The E2 trans–Activator Can Act as a Repressor by Interfering with a Cellular Transcription Factor", *Genes Dev.*, 4, pp. 123–136 (1990).

Studier, F.W. et al., "Use of T7 RNA Polymerase to Direct Expression of Cloned Genes", *Meth. Enzymol.*, 185, pp. 60–89 (1990).

*Primary Examiner*—Robert A. Wax
*Assistant Examiner*—Karen Cochrane Carlson

*Attorney, Agent, or Firm*—Fish & Neave; James F. Haley, Jr.; Madge R. Kanter

[57] ABSTRACT

This invention relates to E2 trans-activation repressors which interfere with normal functioning of the native full-length E2 transcriptional activation protein of the papillomavirus. Native full-length E2 trans-activation protein activates transcription of papillomavirus only through binding to DNA, and it binds to DNA only in the form of a pre-formed homodimer—a pair of identical polypeptide subunits held together by non-covalent interactions. The E2 trans-activation repressors of this invention are proteins, polypeptides or other molecules that dimerize with full-length native E2 polypeptides to form inactive heterodimers, thus interfering with the formation of active homodimers comprising full-length native E2 polypeptides, thereby repressing papillomavirus transcription and replication. The E2 trans-activation repressors of this invention are advantageously used in the treatment of papillomavirus infections and their associated diseases.

1 Claim, 17 Drawing Sheets

FIG. 1

```
PRO VAL ASP LEU ALA SER ARG GLN GLU GLU GLU GLN
285
                         ser             tyr
SER PRO ASP THR GLU GLU GLU PRO VAL THR LEU PRO
        300                                  310
                     tyr
ARG ARG THR ASN ASP GLY PHE HIS LEU LEU LYS ALA
                                             val
GLY GLY SER CYS PHE ALA LEU ILE SER GLY THR ALA ASN
                                    320
 leu       met    S,R,G,F,Y                   tyr  leu
GLN VAL LYS     CYS       TYR ARG PHE ARG VAL LYS KYS ASN HIS
                     340          leu
                                  ARG
                            ser                    ile
ARG HIS ARG TYR GLU ASN CYS THR THR TRP PHE THR VAL ALA ASP
350                                 360              ARG
                                                      370
 tyr                         leu    ser         ile
ASN GLY ALA GLU GLN GLY GLN ALA ILE LEU ILE THR PHE GLY
                                                   380
                        trp                 ile
SER PRO LEU PRO SER GLN ARG GLN ASP PHE LEU LYS HIS VAL
                                            390
                val  ile                           11 new a.a.
PRO LEU PRO PRO GLY MET ASN ILE SER GLY PHE THR ALA SER LEU ASP PHE END
                             400                             410    leu-22 a.a.
```

| Mutant | Alternate Designation | Amino Acid | Mutation | DNA Binding | Dimerization | Repression |
|---|---|---|---|---|---|---|
| 316Y | 393 | 316 | D→Y | + | + | − |
| 317STOP | 352 | 317 | G→stop | − | − | − |
| 333V | 44 | 333 | G→V | − | − | − |
| 337L | 294 | 337 | Q→L | − | + | + |
| 339M | 388 | 339 | K→M | − | + | + |
| 340S | EA28 | 340 | C→S | + | + | + |
| 340R | — | 340 | C→R | − | + | + |
| 340F | — | 340 | C→F | − | + | + |
| 340G | — | 340 | C→G | + | + | + |
| 340Y | — | 340 | C→Y | − | + | + |
| 344L | 38 | 344 | R→L | − | + | + |
| 360S | 213W | 360 | W→S | super-shift | − | − |

FIG. 2A

| Mutant | Alternate Designation | Amino Acid | Mutation | DNA Binding | Dimerization | Repression |
|---|---|---|---|---|---|---|
| 366Y/376L | 354 | 366/376 | N→Y, I→L | + | + | − |
| 370I | 10 | 370 | R→I | + | + | (±) |
| 386W | 9 | 386 | R→W | + | + | + |
| 399I | 111 | 399 | M→I | + | + | + |
| 402* | 3812SS | 402 | 4 aa insert | super-shift | − | − |
| 408* | 36 | 402 | Δ;+ 11aa | + | + | (±) |
| 411* | 211 | 411 | STOP→L | + | + | − |
| 374S/375L 391I | 3SLI | 374,375,391 | A→S, Q→L, K→I | super-shift | (±) | − |

FIG. 2B

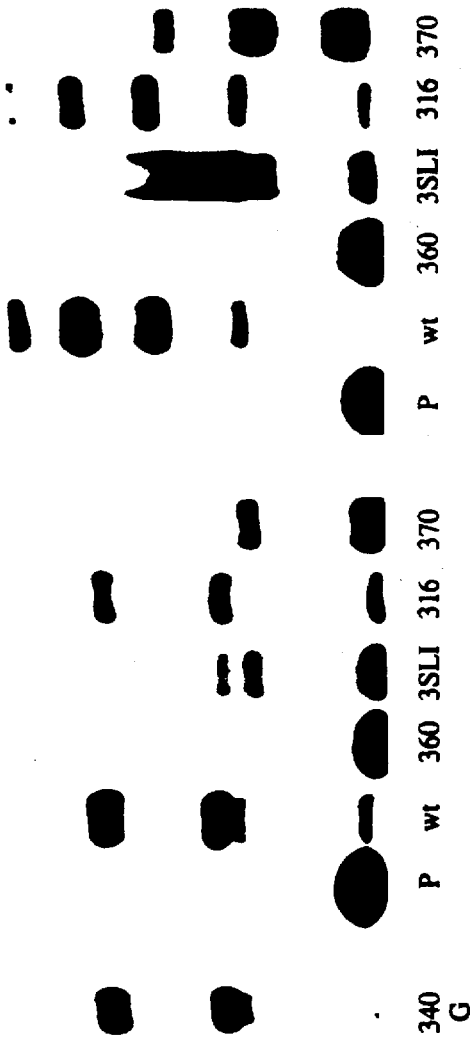

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bovine papillomavirus
        ( B ) STRAIN: Type 1

( i x ) FEATURE:
    ( A ) NAME/KEY: CDS
    ( B ) LOCATION: 1..378

( x i ) SEQUENCE DESCRIPTION: SEQ ID NO:1:

| CCG | GTG | GAC | TTG | GCA | TCA | AGG | CAG | GAA | GAA | GAG | GAG | CAG | TCG | CCC | GAC | 48 |
| Pro | Val | Asp | Leu | Ala | Ser | Arg | Gln | Glu | Glu | Glu | Glu | Gln | Ser | Pro | Asp | |
| 1 | | | | 5 | | | | | 10 | | | | | 15 | | |
| TCC | ACA | GAG | GAA | GAA | CCA | GTG | ACT | CTC | CCA | AGG | CGC | ACC | ACC | AAT | GAT | 96 |
| Ser | Thr | Glu | Glu | Glu | Pro | Val | Thr | Leu | Pro | Arg | Arg | Thr | Thr | Asn | Asp | |
| | | | 20 | | | | | 25 | | | | | 30 | | | |
| GGA | TTC | CAC | CTG | TTA | AAG | GCA | GGA | GGG | TCA | TGC | TTT | GCT | CTA | ATT | TCA | 144 |
| Gly | Phe | His | Leu | Leu | Lys | Ala | Gly | Gly | Ser | Cys | Phe | Ala | Leu | Ile | Ser | |
| | | 35 | | | | | 40 | | | | | 45 | | | | |
| GGA | ACT | GCT | AAC | CAG | GTA | AAG | TGC | TAT | CGC | TTT | CGG | GTG | AAA | AAG | AAC | 192 |
| Gly | Thr | Ala | Asn | Gln | Val | Lys | Cys | Tyr | Arg | Phe | Arg | Val | Lys | Lys | Asn | |
| | 50 | | | | 55 | | | | | 60 | | | | | | |
| CAT | AGA | CAT | CGC | TAC | GAG | AAC | TGC | ACC | ACC | ACC | TGG | TTC | ACA | GTT | GCT | 240 |
| His | Arg | His | Arg | Tyr | Glu | Asn | Cys | Thr | Thr | Thr | Trp | Phe | Thr | Val | Ala | |
| 65 | | | | | 70 | | | | | 75 | | | | | 80 | |
| GAC | AAC | GGT | GCT | GAA | AGA | CAA | GGA | CAA | GCA | CAA | ATA | CTG | ATC | ACC | TTT | 288 |
| Asp | Asn | Gly | Ala | Glu | Arg | Gln | Gly | Gln | Ala | Gln | Ile | Leu | Ile | Thr | Phe | |
| | | | | 85 | | | | | 90 | | | | | 95 | | |
| GGA | TCG | CCA | AGT | CAA | AGG | CAA | GAC | TTT | CTG | AAA | CAT | GTA | CCA | CTA | CCT | 336 |
| Gly | Ser | Pro | Ser | Gln | Arg | Gln | Asp | Phe | Leu | Lys | His | Val | Pro | Leu | Pro | |
| | | | 100 | | | | | 105 | | | | | 110 | | | |
| CCT | GGA | ATG | AAC | ATT | TCC | GGC | TTT | ACA | GCC | AGC | TTG | GAC | TTC | | | 378 |
| Pro | Gly | Met | Asn | Ile | Ser | Gly | Phe | Thr | Ala | Ser | Leu | Asp | Phe | | | |
| | | | 115 | | | | | 120 | | | | | 125 | | | |
| TGA | | | | | | | | | | | | | | | | 381 |

( 2 ) INFORMATION FOR SEQ ID NO:2:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Pro | Val | Asp | Leu | Ala | Ser | Arg | Gln | Glu | Glu | Glu | Glu | Gln | Ser | Pro | Asp |
| 1 | | | | 5 | | | | | 10 | | | | | 15 | |
| Ser | Thr | Glu | Glu | Glu | Pro | Val | Thr | Leu | Pro | Arg | Arg | Thr | Thr | Asn | Asp |
| | | | 20 | | | | | 25 | | | | | 30 | | |
| Gly | Phe | His | Leu | Leu | Lys | Ala | Gly | Gly | Ser | Cys | Phe | Ala | Leu | Ile | Ser |
| | | 35 | | | | | 40 | | | | | 45 | | | |
| Gly | Thr | Ala | Asn | Gln | Val | Lys | Cys | Tyr | Arg | Phe | Arg | Val | Lys | Lys | Asn |
| | 50 | | | | 55 | | | | | 60 | | | | | |
| His | Arg | His | Arg | Tyr | Glu | Asn | Cys | Thr | Thr | Thr | Trp | Phe | Thr | Val | Ala |
| 65 | | | | | 70 | | | | | 75 | | | | | 80 |
| Asp | Asn | Gly | Ala | Glu | Arg | Gln | Gly | Gln | Ala | Gln | Ile | Leu | Ile | Thr | Phe |
| | | | | 85 | | | | | 90 | | | | | 95 | |
| Gly | Ser | Pro | Ser | Gln | Arg | Gln | Asp | Phe | Leu | Lys | His | Val | Pro | Leu | Pro |
| | | | 100 | | | | | 105 | | | | | 110 | | |
| Pro | Gly | Met | Asn | Ile | Ser | Gly | Phe | Thr | Ala | Ser | Leu | Asp | Phe | | |
| | | | 115 | | | | | 120 | | | | | 125 | | |

( 2 ) INFORMATION FOR SEQ ID NO:3:

( i ) SEQUENCE CHARACTERISTICS:

(A) LENGTH: 381 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Bovine papillomavirus
  (B) STRAIN: Type 1

(ix) FEATURE:
  (A) NAME/KEY: CDS
  (B) LOCATION: 1..378

(xi) SEQUENCE DESCRIPTION: SEQ ID NO:3:

| | | | | | | | | | | | | | | | | |
|---|---|---|---|---|---|---|---|---|---|---|---|---|---|---|---|---|
| CCG | GTG | GAC | TTG | GCA | TCA | AGG | CAG | GAA | GAA | GAG | GAG | CAG | TCG | CCC | GAC | 48 |
| Pro | Val | Asp | Leu | Ala | Ser | Arg | Gln | Glu | Glu | Glu | Glu | Gln | Ser | Pro | Asp | |
| 1 | | | | 5 | | | | | 10 | | | | | 15 | | |
| TCC | ACA | GAG | GAA | GAA | CCA | GTG | ACT | CTC | CCA | AGG | CGC | ACC | ACC | AAT | GAT | 96 |
| Ser | Thr | Glu | Glu | Glu | Pro | Val | Thr | Leu | Pro | Arg | Arg | Thr | Thr | Asn | Asp | |
| | | | 20 | | | | | 25 | | | | | 30 | | | |
| GGA | TTC | CAC | CTG | TTA | AAG | GCA | GGA | GGG | TCA | TGC | TTT | GCT | CTA | ATT | TCA | 144 |
| Gly | Phe | His | Leu | Leu | Lys | Ala | Gly | Gly | Ser | Cys | Phe | Ala | Leu | Ile | Ser | |
| | | 35 | | | | | 40 | | | | | 45 | | | | |
| GGA | ACT | GCT | AAC | CTG | GTA | AAG | TGC | TAT | CGC | TTT | CGG | GTG | AAA | AAG | AAC | 192 |
| Gly | Thr | Ala | Asn | Leu | Val | Lys | Cys | Tyr | Arg | Phe | Arg | Val | Lys | Lys | Asn | |
| | 50 | | | | | 55 | | | | | 60 | | | | | |
| CAT | AGA | CAT | CGC | TAC | GAG | AAC | TGC | ACC | ACC | ACC | TGG | TTC | ACA | GTT | GCT | 240 |
| His | Arg | His | Arg | Tyr | Glu | Asn | Cys | Thr | Thr | Thr | Trp | Phe | Thr | Val | Ala | |
| 65 | | | | | 70 | | | | | 75 | | | | | 80 | |
| GAC | AAC | GGT | GCT | GAA | AGA | CAA | GGA | CAA | GCA | CAA | ATA | CTG | ATC | ACC | TTT | 288 |
| Asp | Asn | Gly | Ala | Glu | Arg | Gln | Gly | Gln | Ala | Gln | Ile | Leu | Ile | Thr | Phe | |
| | | | | 85 | | | | | 90 | | | | | 95 | | |
| GGA | TCG | CCA | AGT | CAA | AGG | CAA | GAC | TTT | CTG | AAA | CAT | GTA | CCA | CTA | CCT | 336 |
| Gly | Ser | Pro | Ser | Gln | Arg | Gln | Asp | Phe | Leu | Lys | His | Val | Pro | Leu | Pro | |
| | | | 100 | | | | | 105 | | | | | 110 | | | |
| CCT | GGA | ATG | AAC | ATT | TCC | GGC | TTT | ACA | GCC | AGC | TTG | GAC | TTC | | | 378 |
| Pro | Gly | Met | Asn | Ile | Ser | Gly | Phe | Thr | Ala | Ser | Leu | Asp | Phe | | | |
| | | 115 | | | | | 120 | | | | | 125 | | | | |
| TGA | | | | | | | | | | | | | | | | 381 |

(2) INFORMATION FOR SEQ ID NO:4:

(i) SEQUENCE CHARACTERISTICS:
    (A) LENGTH: 126 amino acids
    (B) TYPE: amino acid
    (D) TOPOLOGY: linear (ii) MOLECULE TYPE: protein (xi) SEQUENCE DESCRIPTION: SEQ ID NO:4:

| | | | | | | | | | | | | | | | |
|---|---|---|---|---|---|---|---|---|---|---|---|---|---|---|---|
| Pro | Val | Asp | Leu | Ala | Ser | Arg | Gln | Glu | Glu | Glu | Glu | Gln | Ser | Pro | Asp |
| 1 | | | | 5 | | | | | 10 | | | | | 15 | |
| Ser | Thr | Glu | Glu | Glu | Pro | Val | Thr | Leu | Pro | Arg | Arg | Thr | Thr | Asn | Asp |
| | | | 20 | | | | | 25 | | | | | 30 | | |
| Gly | Phe | His | Leu | Leu | Lys | Ala | Gly | Gly | Ser | Cys | Phe | Ala | Leu | Ile | Ser |
| | | 35 | | | | | 40 | | | | | 45 | | | |
| Gly | Thr | Ala | Asn | Leu | Val | Lys | Cys | Tyr | Arg | Phe | Arg | Val | Lys | Lys | Asn |
| | 50 | | | | | 55 | | | | | 60 | | | | |
| His | Arg | His | Arg | Tyr | Glu | Asn | Cys | Thr | Thr | Thr | Trp | Phe | Thr | Val | Ala |

|  | 65 |  |  |  | 70 |  |  |  | 75 |  |  |  | 80 |  |
|---|---|---|---|---|---|---|---|---|---|---|---|---|---|---|
| Asp | Asn | Gly | Ala | Glu | Arg | Gln | Gly | Gln | Ala | Gln | Ile | Leu | Ile | Thr | Phe |
|  |  |  |  | 85 |  |  |  | 90 |  |  |  | 95 |  |

| Gly | Ser | Pro | Ser | Gln | Arg | Gln | Asp | Phe | Leu | Lys | His | Val | Pro | Leu | Pro |
|  |  |  | 100 |  |  |  | 105 |  |  |  | 110 |  |

| Pro | Gly | Met | Asn | Ile | Ser | Gly | Phe | Thr | Ala | Ser | Leu | Asp | Phe |
|  |  | 115 |  |  |  | 120 |  |  |  | 125 |

( 2 ) INFORMATION FOR SEQ ID NO:5:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i i i ) HYPOTHETICAL: NO ( i v ) ANTI-SENSE: NO ( i x ) FEATURE:
        ( A ) NAME/KEY: CDS
        ( B ) LOCATION: 1..378

( x i ) SEQUENCE DESCRIPTION: SEQ ID NO:5:

| CCG | GTG | GAC | TTG | GCA | TCA | AGG | CAG | GAA | GAA | GAG | GAG | CAG | TCG | CCC | GAC | 48 |
| Pro | Val | Asp | Leu | Ala | Ser | Arg | Gln | Glu | Glu | Glu | Glu | Gln | Ser | Pro | Asp |  |
| 1 |  |  |  | 5 |  |  |  |  | 10 |  |  |  |  | 15 |  |  |

| TCC | ACA | GAG | GAA | GAA | CCA | GTG | ACT | CTC | CCA | AGG | CGC | ACC | ACC | AAT | GAT | 96 |
| Ser | Thr | Glu | Glu | Glu | Pro | Val | Thr | Leu | Pro | Arg | Arg | Thr | Thr | Asn | Asp |  |
|  |  |  | 20 |  |  |  |  | 25 |  |  |  |  | 30 |  |  |  |

| GGA | TTC | CAC | CTG | TTA | AAG | GCA | GGA | GGG | TCA | TGC | TTT | GCT | CTA | ATT | TCA | 144 |
| Gly | Phe | His | Leu | Leu | Lys | Ala | Gly | Gly | Ser | Cys | Phe | Ala | Leu | Ile | Ser |  |
|  |  | 35 |  |  |  |  | 40 |  |  |  |  | 45 |  |  |  |  |

| GGA | ACT | GCT | AAC | CAG | GTA | ATG | TGC | TAT | CGC | TTT | CGG | GTG | AAA | AAG | AAC | 192 |
| Gly | Thr | Ala | Asn | Gln | Val | Met | Cys | Tyr | Arg | Phe | Arg | Val | Lys | Lys | Asn |  |
|  | 50 |  |  |  |  | 55 |  |  |  |  | 60 |  |  |  |  |  |

| CAT | AGA | CAT | CGC | TAC | GAG | AAC | TGC | ACC | ACC | ACC | TGG | TTC | ACA | GTT | GCT | 240 |
| His | Arg | His | Arg | Tyr | Glu | Asn | Cys | Thr | Thr | Thr | Trp | Phe | Thr | Val | Ala |  |
| 65 |  |  |  | 70 |  |  |  |  | 75 |  |  |  |  | 80 |

| GAC | AAC | GGT | GCT | GAA | AGA | CAA | GGA | CAA | GCA | CAA | ATA | CTG | ATC | ACC | TTT | 288 |
| Asp | Asn | Gly | Ala | Glu | Arg | Gln | Gly | Gln | Ala | Gln | Ile | Leu | Ile | Thr | Phe |  |
|  |  |  |  | 85 |  |  |  |  | 90 |  |  |  |  | 95 |

| GGA | TCG | CCA | AGT | CAA | AGG | CAA | GAC | TTT | CTG | AAA | CAT | GTA | CCA | CTA | CCT | 336 |
| Gly | Ser | Pro | Ser | Gln | Arg | Gln | Asp | Phe | Leu | Lys | His | Val | Pro | Leu | Pro |  |
|  |  |  | 100 |  |  |  |  | 105 |  |  |  |  | 110 |  |  |  |

| CCT | GGA | ATG | AAC | ATT | TCC | GGC | TTT | ACA | GCC | AGC | TTG | GAC | TTC |  |  | 378 |
| Pro | Gly | Met | Asn | Ile | Ser | Gly | Phe | Thr | Ala | Ser | Leu | Asp | Phe |  |  |  |
|  |  | 115 |  |  |  |  | 120 |  |  |  |  | 125 |  |  |  |  |

| TGA |  |  |  |  |  |  |  |  |  |  |  |  |  |  |  | 381 |

( 2 ) INFORMATION FOR SEQ ID NO:6:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Pro | Val | Asp | Leu | Ala | Ser | Arg | Gln | Glu | Glu | Glu | Glu | Gln | Ser | Pro | Asp |
| 1 |  |  |  | 5 |  |  |  |  | 10 |  |  |  |  | 15 |  |

| Ser | Thr | Glu | Glu | Glu | Pro | Val | Thr | Leu | Pro | Arg | Arg | Thr | Thr | Asn | Asp |

|  |  |  | 20 |  |  |  | 25 |  |  |  | 30 |  |  |
|---|---|---|---|---|---|---|---|---|---|---|---|---|---|

```
Gly  Phe  His  Leu  Leu  Lys  Ala  Gly  Gly  Ser  Cys  Phe  Ala  Leu  Ile  Ser
          35                      40                      45

Gly  Thr  Ala  Asn  Gln  Val  Met  Cys  Tyr  Arg  Phe  Arg  Val  Lys  Lys  Asn
          50                      55                      60

His  Arg  His  Arg  Tyr  Glu  Asn  Cys  Thr  Thr  Thr  Trp  Phe  Thr  Val  Ala
65                            70                      75                      80

Asp  Asn  Gly  Ala  Glu  Arg  Gln  Gly  Gln  Ala  Gln  Ile  Leu  Ile  Thr  Phe
                         85                      90                      95

Gly  Ser  Pro  Ser  Gln  Arg  Gln  Asp  Phe  Leu  Lys  His  Val  Pro  Leu  Pro
               100                      105                     110

Pro  Gly  Met  Asn  Ile  Ser  Gly  Phe  Thr  Ala  Ser  Leu  Asp  Phe
          115                     120                     125
```

( 2 ) INFORMATION FOR SEQ ID NO:7:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bovine papillomavirus
        ( B ) STRAIN: Type 1

( i x ) FEATURE:
        ( A ) NAME/KEY: CDS
        ( B ) LOCATION: 1..378

( x i ) SEQUENCE DESCRIPTION: SEQ ID NO:7:

```
CCG  GTG  GAC  TTG  GCA  TCA  AGG  CAG  GAA  GAA  GAG  GAG  CAG  TCG  CCC  GAC         48
Pro  Val  Asp  Leu  Ala  Ser  Arg  Gln  Glu  Glu  Glu  Glu  Gln  Ser  Pro  Asp
1                        5                        10                       15

TCC  ACA  GAG  GAA  GAA  CCA  GTG  ACT  CTC  CCA  AGG  CGC  ACC  ACC  AAT  GAT         96
Ser  Thr  Glu  Glu  Glu  Pro  Val  Thr  Leu  Pro  Arg  Arg  Thr  Thr  Asn  Asp
               20                       25                       30

GGA  TTC  CAC  CTG  TTA  AAG  GCA  GGA  GGG  TCA  TGC  TTT  GCT  CTA  ATT  TCA        144
Gly  Phe  His  Leu  Leu  Lys  Ala  Gly  Gly  Ser  Cys  Phe  Ala  Leu  Ile  Ser
               35                       40                       45

GGA  ACT  GCT  AAC  CAG  GTA  AAG  TTC  TAT  CGC  TTT  CGG  GTG  AAA  AAG  AAC        192
Gly  Thr  Ala  Asn  Gln  Val  Lys  Phe  Tyr  Arg  Phe  Arg  Val  Lys  Lys  Asn
     50                       55                       60

CAT  AGA  CAT  CGC  TAC  GAG  AAC  TGC  ACC  ACC  ACC  TGG  TTC  ACA  GTT  GCT        240
His  Arg  His  Arg  Tyr  Glu  Asn  Cys  Thr  Thr  Thr  Trp  Phe  Thr  Val  Ala
65                       70                       75                       80

GAC  AAC  GGT  GCT  GAA  AGA  CAA  GGA  CAA  GCA  CAA  ATA  CTG  ATC  ACC  TTT        288
Asp  Asn  Gly  Ala  Glu  Arg  Gln  Gly  Gln  Ala  Gln  Ile  Leu  Ile  Thr  Phe
                         85                       90                       95

GGA  TCG  CCA  AGT  CAA  AGG  CAA  GAC  TTT  CTG  AAA  CAT  GTA  CCA  CTA  CCT        336
Gly  Ser  Pro  Ser  Gln  Arg  Gln  Asp  Phe  Leu  Lys  His  Val  Pro  Leu  Pro
               100                      105                      110

CCT  GGA  ATG  AAC  ATT  TCC  GGC  TTT  ACA  GCC  AGC  TTG  GAC  TTC                  378
Pro  Gly  Met  Asn  Ile  Ser  Gly  Phe  Thr  Ala  Ser  Leu  Asp  Phe
          115                      120                      125

TGA                                                                                  381
```

( 2 ) INFORMATION FOR SEQ ID NO:8:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Pro Val Asp Leu Ala Ser Arg Gln Glu Glu Glu Glu Gln Ser Pro Asp
 1               5                  10                  15

Ser Thr Glu Glu Glu Pro Val Thr Leu Pro Arg Arg Thr Thr Asn Asp
             20                  25                  30

Gly Phe His Leu Leu Lys Ala Gly Gly Ser Cys Phe Ala Leu Ile Ser
         35                  40                  45

Gly Thr Ala Asn Gln Val Lys Phe Tyr Arg Phe Arg Val Lys Lys Asn
     50                  55                  60

His Arg His Arg Tyr Glu Asn Cys Thr Thr Thr Trp Phe Thr Val Ala
 65                  70                  75                  80

Asp Asn Gly Ala Glu Arg Gln Gly Gln Gln Ile Leu Ile Thr Phe
                 85                  90                  95

Gly Ser Pro Ser Gln Arg Gln Asp Phe Leu Lys His Val Pro Leu Pro
             100                 105                 110

Pro Gly Met Asn Ile Ser Gly Phe Thr Ala Ser Leu Asp Phe
             115                 120                 125
```

( 2 ) INFORMATION FOR SEQ ID NO:9:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bovine papillomavirus
        ( B ) STRAIN: Type 1

( i x ) FEATURE:
        ( A ) NAME/KEY: CDS
        ( B ) LOCATION: 1..378

( x i ) SEQUENCE DESCRIPTION: SEQ ID NO:9:

```
CCG GTG GAC TTG GCA TCA AGG CAG GAA GAA GAG GAG CAG TCG CCC GAC      48
Pro Val Asp Leu Ala Ser Arg Gln Glu Glu Glu Glu Gln Ser Pro Asp
 1               5                  10                  15

TCC ACA GAG GAA GAA CCA GTG ACT CTC CCA AGG CGC ACC ACC AAT GAT      96
Ser Thr Glu Glu Glu Pro Val Thr Leu Pro Arg Arg Thr Thr Asn Asp
             20                  25                  30

GGA TTC CAC CTG TTA AAG GCA GGA GGG TCA TGC TTT GCT CTA ATT TCA     144
Gly Phe His Leu Leu Lys Ala Gly Gly Ser Cys Phe Ala Leu Ile Ser
         35                  40                  45

GGA ACT GCT AAC CAG GTA AAG CGC TAT CGC TTT CGG GTG AAA AAG AAC     192
Gly Thr Ala Asn Gln Val Lys Arg Tyr Arg Phe Arg Val Lys Lys Asn
     50                  55                  60

CAT AGA CAT CGC TAC GAG AAC TGC ACC ACC ACC TGG TTC ACA GTT GCT     240
His Arg His Arg Tyr Glu Asn Cys Thr Thr Thr Trp Phe Thr Val Ala
 65                  70                  75                  80
```

| | | | | | | | | | | | | | | | | |
|---|---|---|---|---|---|---|---|---|---|---|---|---|---|---|---|---|
| GAC | AAC | GGT | GCT | GAA | AGA | CAA | GGA | CAA | GCA | CAA | ATA | CTG | ATC | ACC | TTT | 288 |
| Asp | Asn | Gly | Ala | Glu | Arg | Gln | Gly | Gln | Ala | Gln | Ile | Leu | Ile | Thr | Phe | |
| | | | | 85 | | | | | 90 | | | | | 95 | | |
| GGA | TCG | CCA | AGT | CAA | AGG | CAA | GAC | TTT | CTG | AAA | CAT | GTA | CCA | CTA | CCT | 336 |
| Gly | Ser | Pro | Ser | Gln | Arg | Gln | Asp | Phe | Leu | Lys | His | Val | Pro | Leu | Pro | |
| | | | 100 | | | | | 105 | | | | | 110 | | | |
| CCT | GGA | ATG | AAC | ATT | TCC | GGC | TTT | ACA | GCC | AGC | TTG | GAC | TTC | | | 378 |
| Pro | Gly | Met | Asn | Ile | Ser | Gly | Phe | Thr | Ala | Ser | Leu | Asp | Phe | | | |
| | | 115 | | | | | 120 | | | | | 125 | | | | |
| TGA | | | | | | | | | | | | | | | | 381 |

( 2 ) INFORMATION FOR SEQ ID NO:10:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Pro | Val | Asp | Leu | Ala | Ser | Arg | Gln | Glu | Glu | Glu | Gln | Ser | Pro | Asp |
| 1 | | | | 5 | | | | | 10 | | | | | 15 |
| Ser | Thr | Glu | Glu | Glu | Pro | Val | Thr | Leu | Pro | Arg | Arg | Thr | Thr | Asn | Asp |
| | | | 20 | | | | | 25 | | | | | 30 | | |
| Gly | Phe | His | Leu | Leu | Lys | Ala | Gly | Gly | Ser | Cys | Phe | Ala | Leu | Ile | Ser |
| | | 35 | | | | | 40 | | | | | 45 | | | |
| Gly | Thr | Ala | Asn | Gln | Val | Lys | Arg | Tyr | Arg | Phe | Arg | Val | Lys | Lys | Asn |
| | 50 | | | | | 55 | | | | | 60 | | | | |
| His | Arg | His | Arg | Tyr | Glu | Asn | Cys | Thr | Thr | Thr | Trp | Phe | Thr | Val | Ala |
| 65 | | | | | 70 | | | | | 75 | | | | | 80 |
| Asp | Asn | Gly | Ala | Glu | Arg | Gln | Gly | Gln | Ala | Gln | Ile | Leu | Ile | Thr | Phe |
| | | | | 85 | | | | | 90 | | | | | 95 | |
| Gly | Ser | Pro | Ser | Gln | Arg | Gln | Asp | Phe | Leu | Lys | His | Val | Pro | Leu | Pro |
| | | | 100 | | | | | 105 | | | | | 110 | | |
| Pro | Gly | Met | Asn | Ile | Ser | Gly | Phe | Thr | Ala | Ser | Leu | Asp | Phe | | |
| | | 115 | | | | | 120 | | | | | 125 | | | |

( 2 ) INFORMATION FOR SEQ ID NO:11:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bovine papillomavirus
        ( B ) STRAIN: Type 1

( i x ) FEATURE:
        ( A ) NAME/KEY: CDS
        ( B ) LOCATION: 1..378

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| CCG | GTG | GAC | TTG | GCA | TCA | AGG | CAG | GAA | GAA | GAG | GAG | CAG | TCG | CCC | GAC | 48 |
| Pro | Val | Asp | Leu | Ala | Ser | Arg | Gln | Glu | Glu | Glu | Glu | Gln | Ser | Pro | Asp | |
| 1 | | | | 5 | | | | | 10 | | | | | 15 | | |
| TCC | ACA | GAG | GAA | GAA | CCA | GTG | ACT | CTC | CCA | AGG | CGC | ACC | ACC | AAT | GAT | 96 |

| | | | | | | | | | | | | | | | |
|---|---|---|---|---|---|---|---|---|---|---|---|---|---|---|---|
|Ser|Thr|Glu|Glu|Glu|Pro|Val|Thr|Leu|Pro|Arg|Arg|Thr|Thr|Asn|Asp|
| | |  |20| | | | |25| | | | |30| | |

```
GGA TTC CAC CTG TTA AAG GCA GGA GGG TCA TGC TTT GCT CTA ATT TCA      144
Gly Phe His Leu Leu Lys Ala Gly Gly Ser Cys Phe Ala Leu Ile Ser
            35                  40                  45

GGA ACT GCT AAC CAG GTA AAG TAC TAT CGC TTT CGG GTG AAA AAG AAC      192
Gly Thr Ala Asn Gln Val Lys Tyr Tyr Arg Phe Arg Val Lys Lys Asn
     50                  55                  60

CAT AGA CAT CGC TAC GAG AAC TGC ACC ACC ACC TGG TTC ACA GTT GCT      240
His Arg His Arg Tyr Glu Asn Cys Thr Thr Thr Trp Phe Thr Val Ala
 65              70                  75                      80

GAC AAC GGT GCT GAA AGA CAA GGA CAA GCA CAA ATA CTG ATC ACC TTT      288
Asp Asn Gly Ala Glu Arg Gln Gly Gln Ala Gln Ile Leu Ile Thr Phe
                     85                  90                  95

GGA TCG CCA AGT CAA AGG CAA GAC TTT CTG AAA CAT GTA CCA CTA CCT      336
Gly Ser Pro Ser Gln Arg Gln Asp Phe Leu Lys His Val Pro Leu Pro
             100                 105                 110

CCT GGA ATG AAC ATT TCC GGC TTT ACA GCC AGC TTG GAC TTC              378
Pro Gly Met Asn Ile Ser Gly Phe Thr Ala Ser Leu Asp Phe
         115                 120                 125

TGA                                                                  381
```

(2) INFORMATION FOR SEQ ID NO:12:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:12:

```
Pro Val Asp Leu Ala Ser Arg Gln Glu Glu Glu Gln Ser Pro Asp
 1               5                   10                  15

Ser Thr Glu Glu Glu Pro Val Thr Leu Pro Arg Arg Thr Thr Asn Asp
             20                  25                  30

Gly Phe His Leu Leu Lys Ala Gly Gly Ser Cys Phe Ala Leu Ile Ser
             35                  40                  45

Gly Thr Ala Asn Gln Val Lys Tyr Tyr Arg Phe Arg Val Lys Lys Asn
     50                  55                  60

His Arg His Arg Tyr Glu Asn Cys Thr Thr Thr Trp Phe Thr Val Ala
 65              70                  75                      80

Asp Asn Gly Ala Glu Arg Gln Gly Gln Ala Gln Ile Leu Ile Thr Phe
                     85                  90                  95

Gly Ser Pro Ser Gln Arg Gln Asp Phe Leu Lys His Val Pro Leu Pro
             100                 105                 110

Pro Gly Met Asn Ile Ser Gly Phe Thr Ala Ser Leu Asp Phe
         115                 120                 125
```

(2) INFORMATION FOR SEQ ID NO:13:

(i) SEQUENCE CHARACTERISTICS:
        (A) LENGTH: 381 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO ( v i ) ORIGINAL SOURCE:
  ( A ) ORGANISM: Bovine papillomavirus
  ( B ) STRAIN: Type 1

( i x ) FEATURE:
  ( A ) NAME/KEY: CDS
  ( B ) LOCATION: 1..378

( x i ) SEQUENCE DESCRIPTION: SEQ ID NO:13:

```
CCG GTG GAC TTG GCA TCA AGG CAG GAA GAA GAG GAG CAG TCG CCC GAC        48
Pro Val Asp Leu Ala Ser Arg Gln Glu Glu Glu Glu Gln Ser Pro Asp
 1               5                  10                  15

TCC ACA GAG GAA GAA CCA GTG ACT CTC CCA AGG CGC ACC ACC AAT GAT        96
Ser Thr Glu Glu Glu Pro Val Thr Leu Pro Arg Arg Thr Thr Asn Asp
                20                  25                  30

GGA TTC CAC CTG TTA AAG GCA GGG TCA TGC TTT GCT CTA ATT TCA           144
Gly Phe His Leu Leu Lys Ala Gly Gly Ser Cys Phe Ala Leu Ile Ser
            35                  40                  45

GGA ACT GCT AAC CAG GTA AAG TGC TAT CGC TTT CTG GTG AAA AAG AAC       192
Gly Thr Ala Asn Gln Val Lys Cys Tyr Arg Phe Leu Val Lys Lys Asn
        50                  55                  60

CAT AGA CAT CGC TAC GAG AAC TGC ACC ACC ACC TGG TTC ACA GTT GCT       240
His Arg His Arg Tyr Glu Asn Cys Thr Thr Thr Trp Phe Thr Val Ala
 65                  70                  75                  80

GAC AAC GGT GCT GAA AGA CAA GGA CAA GCA CAA ATA CTG ATC ACC TTT       288
Asp Asn Gly Ala Glu Arg Gln Gly Gln Ala Gln Ile Leu Ile Thr Phe
                85                  90                  95

GGA TCG CCA AGT CAA AGG CAA GAC TTT CTG AAA CAT GTA CCA CTA CCT       336
Gly Ser Pro Ser Gln Arg Gln Asp Phe Leu Lys His Val Pro Leu Pro
            100                 105                 110

CCT GGA ATG AAC ATT TCC GGC TTT ACA GCC AGC TTG GAC TTC              378
Pro Gly Met Asn Ile Ser Gly Phe Thr Ala Ser Leu Asp Phe
        115                 120                 125

TGA                                                                   381
```

( 2 ) INFORMATION FOR SEQ ID NO:14:

( i ) SEQUENCE CHARACTERISTICS:
    ( A ) LENGTH: 126 amino acids
    ( B ) TYPE: amino acid
    ( D ) TOPOLOGY: linear ( i i ) MOLECULE TYPE: protein ( x i ) SEQUENCE DESCRIPTION: SEQ ID NO:14:

```
Pro Val Asp Leu Ala Ser Arg Gln Glu Glu Glu Glu Gln Ser Pro Asp
 1               5                  10                  15

Ser Thr Glu Glu Glu Pro Val Thr Leu Pro Arg Arg Thr Thr Asn Asp
                20                  25                  30

Gly Phe His Leu Leu Lys Ala Gly Gly Ser Cys Phe Ala Leu Ile Ser
            35                  40                  45

Gly Thr Ala Asn Gln Val Lys Cys Tyr Arg Phe Leu Val Lys Lys Asn
        50                  55                  60

His Arg His Arg Tyr Glu Asn Cys Thr Thr Thr Trp Phe Thr Val Ala
 65                  70                  75                  80

Asp Asn Gly Ala Glu Arg Gln Gly Gln Ala Gln Ile Leu Ile Thr Phe
                85                  90                  95

Gly Ser Pro Ser Gln Arg Gln Asp Phe Leu Lys His Val Pro Leu Pro
            100                 105                 110

Pro Gly Met Asn Ile Ser Gly Phe Thr Ala Ser Leu Asp Phe
        115                 120                 125
```

( 2 ) INFORMATION FOR SEQ ID NO:15:

( i ) SEQUENCE CHARACTERISTICS:
        ( A ) LENGTH: 222 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bovine papillomavirus
        ( B ) STRAIN: Type 1

( i x ) FEATURE:
        ( A ) NAME/KEY: CDS
        ( B ) LOCATION: 1..219

( x i ) SEQUENCE DESCRIPTION: SEQ ID NO:15:

```
GTA AAG TGC TAT CGC TTT CGG GTG AAA AAG AAC CAT AGA CAT CGC TAC      48
Val Lys Cys Tyr Arg Phe Arg Val Lys Lys Asn His Arg His Arg Tyr
 1               5                  10                  15

GAG AAC TGC ACC ACC ACC TGG TTC ACA GTT GCT GAC AAC GGT GCT GAA      96
Glu Asn Cys Thr Thr Thr Trp Phe Thr Val Ala Asp Asn Gly Ala Glu
             20                  25                  30

AGA CAA GGA CAA GCA CAA ATA CTG ATC ACC TTT GGA TCG CCA AGT CAA     144
Arg Gln Gly Gln Ala Gln Ile Leu Ile Thr Phe Gly Ser Pro Ser Gln
         35                  40                  45

AGG CAA GAC TTT CTG AAA CAT GTA CCA CTA CCT CCT GGA ATG AAC ATT     192
Arg Gln Asp Phe Leu Lys His Val Pro Leu Pro Pro Gly Met Asn Ile
     50                  55                  60

TCC GGC TTT ACA GCC AGC TTG GAC TTC TGA                             222
Ser Gly Phe Thr Ala Ser Leu Asp Phe
 65                  70
```

( 2 ) INFORMATION FOR SEQ ID NO:16:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Val Lys Cys Tyr Arg Phe Arg Val Lys Lys Asn His Arg His Arg Tyr
 1               5                  10                  15

Glu Asn Cys Thr Thr Thr Trp Phe Thr Val Ala Asp Asn Gly Ala Glu
             20                  25                  30

Arg Gln Gly Gln Ala Gln Ile Leu Ile Thr Phe Gly Ser Pro Ser Gln
         35                  40                  45

Arg Gln Asp Phe Leu Lys His Val Pro Leu Pro Pro Gly Met Asn Ile
     50                  55                  60

Ser Gly Phe Thr Ala Ser Leu Asp Phe
 65                  70
```

( 2 ) INFORMATION FOR SEQ ID NO:17:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AGCAACTAGT CCCAAG                                                               16

( 2 ) INFORMATION FOR SEQ ID NO:18:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:18:

CTCGAGAAGC TTGACGGATC CG                                                        22

( 2 ) INFORMATION FOR SEQ ID NO:19:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:19:

TGCAGAGCTC TTCGAACTGC CTAGGCTTAA                                                 30

( 2 ) INFORMATION FOR SEQ ID NO:20:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:20:

GATCCTTTGC CGCCAC                                                                16

( 2 ) INFORMATION FOR SEQ ID NO:21:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:21:

GAAACGGCGG TGGTAC                                                                16

( 2 ) INFORMATION FOR SEQ ID NO:22:

( i ) SEQUENCE CHARACTERISTICS:
( A ) LENGTH: 258 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 1..255

( x i ) SEQUENCE DESCRIPTION: SEQ ID NO:22:

```
ATG GCT AGC AAC ACT ACA CCC ATA GTA CAT TTA AAA GGT GAT GCT AAT    48
Met Ala Ser Asn Thr Thr Pro Ile Val His Leu Lys Gly Asp Ala Asn
 1           5                  10                      15

ACT TTA AAA TGT TTA AGA TAT AGA TTT AAA AAG CAT TGT ACA TTG TAT    96
Thr Leu Lys Cys Leu Arg Tyr Arg Phe Lys Lys His Cys Thr Leu Tyr
        20                  25                  30
```

| | | | | | | | | | | | | | | | | |
|---|---|---|---|---|---|---|---|---|---|---|---|---|---|---|---|---|
| ACT | GCA | GTG | TCG | TCT | ACA | TGG | CAT | TGG | ACA | GGA | CAT | AAT | GTA | AAA | CAT | 144 |
| Thr | Ala | Val | Ser | Ser | Thr | Trp | His | Trp | Thr | Gly | His | Asn | Val | Lys | His | |
| | | 35 | | | | | 40 | | | | | 45 | | | | |
| AAA | AGT | GCA | ATT | GTT | ACA | CTT | ACA | TAT | GAT | AGT | GAA | TGG | CAA | CGT | GAC | 192 |
| Lys | Ser | Ala | Ile | Val | Thr | Leu | Thr | Tyr | Asp | Ser | Glu | Trp | Gln | Arg | Asp | |
| | 50 | | | | | 55 | | | | | 60 | | | | | |
| CAA | TTT | TTG | TCT | CAA | GTT | AAA | ATA | CCA | AAA | ACT | ATT | ACA | GTG | TCT | ACT | 240 |
| Gln | Phe | Leu | Ser | Gln | Val | Lys | Ile | Pro | Lys | Thr | Ile | Thr | Val | Ser | Thr | |
| 65 | | | | | 70 | | | | | 75 | | | | | 80 | |
| GGA | TTT | ATG | TCT | ATA | TGA | | | | | | | | | | | 258 |
| Gly | Phe | Met | Ser | Ile | | | | | | | | | | | | |
| | | | | 85 | | | | | | | | | | | | |

(2) INFORMATION FOR SEQ ID NO:23:

(i) SEQUENCE CHARACTERISTICS:
        (A) LENGTH: 85 amino acids
        (B) TYPE: amino acid
        (D) TOPOLOGY: linear (ii) MOLECULE TYPE: protein (xi) SEQUENCE DESCRIPTION: SEQ ID NO:23:

| | | | | | | | | | | | | | | |
|---|---|---|---|---|---|---|---|---|---|---|---|---|---|---|
| Met | Ala | Ser | Asn | Thr | Thr | Pro | Ile | Val | His | Leu | Lys | Gly | Asp | Ala | Asn |
| 1 | | | | 5 | | | | | 10 | | | | | 15 | |
| Thr | Leu | Lys | Cys | Leu | Arg | Tyr | Arg | Phe | Lys | Lys | His | Cys | Thr | Leu | Tyr |
| | | | 20 | | | | | 25 | | | | | 30 | | |
| Thr | Ala | Val | Ser | Ser | Thr | Trp | His | Trp | Thr | Gly | His | Asn | Val | Lys | His |
| | | | 35 | | | | | 40 | | | | | 45 | | |
| Lys | Ser | Ala | Ile | Val | Thr | Leu | Thr | Tyr | Asp | Ser | Glu | Trp | Gln | Arg | Asp |
| | 50 | | | | | 55 | | | | | 60 | | | | |
| Gln | Phe | Leu | Ser | Gln | Val | Lys | Ile | Pro | Lys | Thr | Ile | Thr | Val | Ser | Thr |
| 65 | | | | | 70 | | | | | 75 | | | | | 80 |
| Gly | Phe | Met | Ser | Ile | | | | | | | | | | | |
| | | | | 85 | | | | | | | | | | | |

(2) INFORMATION FOR SEQ ID NO:24:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..369

(xi) SEQUENCE DESCRIPTION: SEQ ID NO:24:

| | | | | | | | | | | | | | | | | |
|---|---|---|---|---|---|---|---|---|---|---|---|---|---|---|---|---|
| ATG | GTA | CCA | GAC | ACC | GGA | AAC | CCC | TGC | CAC | ACC | ACT | AAG | TTG | TTG | CAC | 48 |
| Met | Val | Pro | Asp | Thr | Gly | Asn | Pro | Cys | His | Thr | Thr | Lys | Leu | Leu | His | |
| 1 | | | | 5 | | | | | 10 | | | | | 15 | | |
| AGA | GAC | TCA | GTG | GAC | AGT | GCT | CCA | ATC | CTC | ACT | GCA | TTT | AAC | AGC | TCA | 96 |
| Arg | Asp | Ser | Val | Asp | Ser | Ala | Pro | Ile | Leu | Thr | Ala | Phe | Asn | Ser | Ser | |
| | | | 20 | | | | | 25 | | | | | 30 | | | |
| CAC | AAA | GGA | CGG | ATT | AAC | TGT | AAT | AGT | AAC | ACT | ACA | CCC | ATA | GTA | CAT | 144 |
| His | Lys | Gly | Arg | Ile | Asn | Cys | Asn | Ser | Asn | Thr | Thr | Pro | Ile | Val | His | |
| | | 35 | | | | | 40 | | | | | 45 | | | | |
| TTA | AAA | GGT | GAT | GCT | AAT | ACT | TTA | AAA | TGT | TTA | AGA | TAT | AGA | TTT | AAA | 192 |
| Leu | Lys | Gly | Asp | Ala | Asn | Thr | Leu | Lys | Cys | Leu | Arg | Tyr | Arg | Phe | Lys | |
| | 50 | | | | | 55 | | | | | 60 | | | | | |
| AAG | CAT | TGT | ACA | TTG | TAT | ACT | GCA | GTG | TCG | TCT | ACA | TGG | CAT | TGG | ACA | 240 |
| Lys | His | Cys | Thr | Leu | Tyr | Thr | Ala | Val | Ser | Ser | Thr | Trp | His | Trp | Thr | |
| 65 | | | | | 70 | | | | | 75 | | | | | 80 | |

```
GGA CAT AAT GTA AAA CAT AAA AGT GCA ATT GTT ACA CTT ACA TAT GAT    288
Gly His Asn Val Lys His Lys Ser Ala Ile Val Thr Leu Thr Tyr Asp
                 85                  90                  95

AGT GAA TGG CAA CGT GAC CAA TTT TTG TCT CAA GTT AAA ATA CCA AAA    336
Ser Glu Trp Gln Arg Asp Gln Phe Leu Ser Gln Val Lys Ile Pro Lys
            100                 105                 110

ACT ATT ACA GTG TCT ACT GGA TTT ATG TCT ATA TGA                    372
Thr Ile Thr Val Ser Thr Gly Phe Met Ser Ile
        115                 120
```

( 2 ) INFORMATION FOR SEQ ID NO:25:

( i ) SEQUENCE CHARACTERISTICS:
        ( A ) LENGTH: 123 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met Val Pro Asp Thr Gly Asn Pro Cys His Thr Thr Lys Leu Leu His
 1               5                  10                  15

Arg Asp Ser Val Asp Ser Ala Pro Ile Leu Thr Ala Phe Asn Ser Ser
            20                  25                  30

His Lys Gly Arg Ile Asn Cys Asn Ser Asn Thr Thr Pro Ile Val His
        35                  40                  45

Leu Lys Gly Asp Ala Asn Thr Leu Lys Cys Leu Arg Tyr Arg Phe Lys
    50                  55                  60

Lys His Cys Thr Leu Tyr Thr Ala Val Ser Ser Thr Trp His Trp Thr
65                  70                  75                  80

Gly His Asn Val Lys His Lys Ser Ala Ile Val Thr Leu Thr Tyr Asp
                85                  90                  95

Ser Glu Trp Gln Arg Asp Gln Phe Leu Ser Gln Val Lys Ile Pro Lys
            100                 105                 110

Thr Ile Thr Val Ser Thr Gly Phe Met Ser Ile
        115                 120
```

( 2 ) INFORMATION FOR SEQ ID NO:26:

( i ) SEQUENCE CHARACTERISTICS:
        ( A ) LENGTH: 939 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..936

( x i ) SEQUENCE DESCRIPTION: SEQ ID NO:26:

```
ATG GAA CCG GTC GAC CCG CGT CTG GAA CCA TGG AAA CAC CCC GGG TCC     48
Met Glu Pro Val Asp Pro Arg Leu Glu Pro Trp Lys His Pro Gly Ser
 1               5                  10                  15

CAG CCG AAA ACC GCG TGC ACC AAC TGC TAC TGC AAA AAA TGC TGC TTC     96
Gln Pro Lys Thr Ala Cys Thr Asn Cys Tyr Cys Lys Lys Cys Cys Phe
            20                  25                  30

CAC TGC CAG GTT TGC TTC ATC ACC AAA GCC CTA GGT ATC TCT TAC GGC    144
His Cys Gln Val Cys Phe Ile Thr Lys Ala Leu Gly Ile Ser Tyr Gly
        35                  40                  45

CGT AAA AAA CGT CGT CAG CGA CGT CGT CCG CCG CAG GGA TCT TCC ATG    192
Arg Lys Lys Arg Arg Gln Arg Arg Arg Pro Pro Gln Gly Ser Ser Met
    50                  55                  60
```

| | | | | | | | | | | | | | | | | |
|---|---|---|---|---|---|---|---|---|---|---|---|---|---|---|---|---|
| GCC | GGT | GCT | GGA | CGC | ATT | TAC | TAT | TCT | CGC | TTT | GGT | GAC | GAG | GCA | GCC | 240 |
| Ala | Gly | Ala | Gly | Arg | Ile | Tyr | Tyr | Ser | Arg | Phe | Gly | Asp | Glu | Ala | Ala | |
| 65 | | | | 70 | | | | 75 | | | | | | | 80 | |
| AGA | TTT | AGT | ACA | ACA | GGG | CAT | TAC | TCT | GTA | AGA | GAT | CAG | GAC | AGA | GTG | 288 |
| Arg | Phe | Ser | Thr | Thr | Gly | His | Tyr | Ser | Val | Arg | Asp | Gln | Asp | Arg | Val | |
| | | | | 85 | | | | | 90 | | | | | 95 | | |
| TAT | GCT | GGT | GTC | TCA | TCC | ACC | TCT | TCT | GAT | TTT | AGA | GAT | CGC | CCA | GAC | 336 |
| Tyr | Ala | Gly | Val | Ser | Ser | Thr | Ser | Ser | Asp | Phe | Arg | Asp | Arg | Pro | Asp | |
| | | | | 100 | | | | | 105 | | | | | 110 | | |
| GGA | GTC | TGG | GTC | GCA | TCC | GAA | GGA | CCT | GAA | GGA | GAC | CCT | GCA | GGA | AAA | 384 |
| Gly | Val | Trp | Val | Ala | Ser | Glu | Gly | Pro | Glu | Gly | Asp | Pro | Ala | Gly | Lys | |
| | | | 115 | | | | | 120 | | | | | 125 | | | |
| GAA | GCC | GAG | CCA | GCC | CAG | CCT | GTC | TCT | TCT | TTG | CTC | GGC | TCC | CCC | GCC | 432 |
| Glu | Ala | Glu | Pro | Ala | Gln | Pro | Val | Ser | Ser | Leu | Leu | Gly | Ser | Pro | Ala | |
| | 130 | | | | | 135 | | | | | 140 | | | | | |
| TGC | GGT | CCC | ATC | AGA | GCA | GGC | CTC | GGT | TGG | GTA | CGG | GAC | GGT | CCT | CGC | 480 |
| Cys | Gly | Pro | Ile | Arg | Ala | Gly | Leu | Gly | Trp | Val | Arg | Asp | Gly | Pro | Arg | |
| 145 | | | | | 150 | | | | | 155 | | | | | 160 | |
| TCG | CAC | CCC | TAC | AAT | TTT | CCT | GCA | GGC | TCG | GGG | GGC | TCT | ATT | CTC | CGC | 528 |
| Ser | His | Pro | Tyr | Asn | Phe | Pro | Ala | Gly | Ser | Gly | Gly | Ser | Ile | Leu | Arg | |
| | | | | 165 | | | | | 170 | | | | | 175 | | |
| TCT | TCC | TCC | ACC | CCG | GTG | CAG | GGC | ACG | GTA | CCG | GTG | GAC | TTG | GCA | TCA | 576 |
| Ser | Ser | Ser | Thr | Pro | Val | Gln | Gly | Thr | Val | Pro | Val | Asp | Leu | Ala | Ser | |
| | | | 180 | | | | | 185 | | | | | 190 | | | |
| AGG | CAG | GAA | GAA | GAG | GAG | CAG | TCG | CCC | GAC | TCC | ACA | GAG | GAA | GAA | CCA | 624 |
| Arg | Gln | Glu | Glu | Glu | Glu | Gln | Ser | Pro | Asp | Ser | Thr | Glu | Glu | Glu | Pro | |
| | | | 195 | | | | | 200 | | | | | 205 | | | |
| GTG | ACT | CTC | CCA | AGG | CGC | ACC | ACC | AAT | GAT | GGA | TTC | CAC | CTG | TTA | AAG | 672 |
| Val | Thr | Leu | Pro | Arg | Arg | Thr | Thr | Asn | Asp | Gly | Phe | His | Leu | Leu | Lys | |
| | 210 | | | | | 215 | | | | | 220 | | | | | |
| GCA | GGA | GGG | TCA | TGC | TTT | GCT | CTA | ATT | TCA | GGA | ACT | GCT | AAC | CAG | GTA | 720 |
| Ala | Gly | Gly | Ser | Cys | Phe | Ala | Leu | Ile | Ser | Gly | Thr | Ala | Asn | Gln | Val | |
| 225 | | | | | 230 | | | | | 235 | | | | | 240 | |
| AAG | TGC | TAT | CGC | TTT | CGG | GTG | AAA | AAG | AAC | CAT | AGA | CAT | CGC | TAC | GAG | 768 |
| Lys | Cys | Tyr | Arg | Phe | Arg | Val | Lys | Lys | Asn | His | Arg | His | Arg | Tyr | Glu | |
| | | | | 245 | | | | | 250 | | | | | 255 | | |
| AAC | TGC | ACC | ACC | ACC | TGG | TTC | ACA | GTT | GCT | GAC | AAC | GGT | GCT | GAA | AGA | 816 |
| Asn | Cys | Thr | Thr | Thr | Trp | Phe | Thr | Val | Ala | Asp | Asn | Gly | Ala | Glu | Arg | |
| | | | 260 | | | | | 265 | | | | | 270 | | | |
| CAA | GGA | CAA | GCA | CAA | ATA | CTG | ATC | ACC | TTT | GGA | TCG | CCA | AGT | CAA | AGG | 864 |
| Gln | Gly | Gln | Ala | Gln | Ile | Leu | Ile | Thr | Phe | Gly | Ser | Pro | Ser | Gln | Arg | |
| | | | 275 | | | | | 280 | | | | | 285 | | | |
| CAA | GAC | TTT | CTG | AAA | CAT | GTA | CCA | CTA | CCT | CCT | GGA | ATG | AAC | ATT | TCC | 912 |
| Gln | Asp | Phe | Leu | Lys | His | Val | Pro | Leu | Pro | Pro | Gly | Met | Asn | Ile | Ser | |
| | 290 | | | | | 295 | | | | | 300 | | | | | |
| GGC | TTT | ACA | GCC | AGC | TTG | GAC | TTC | TGA | | | | | | | | 939 |
| Gly | Phe | Thr | Ala | Ser | Leu | Asp | Phe | | | | | | | | | |
| 305 | | | | | 310 | | | | | | | | | | | |

( 2 ) INFORMATION FOR SEQ ID NO:27:

( i ) SEQUENCE CHARACTERISTICS:
        ( A ) LENGTH: 312 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

| | | | | | | | | | | | | | | | |
|---|---|---|---|---|---|---|---|---|---|---|---|---|---|---|---|
| Met | Glu | Pro | Val | Asp | Pro | Arg | Leu | Glu | Pro | Trp | Lys | His | Pro | Gly | Ser |
| 1 | | | | 5 | | | | | 10 | | | | | 15 | |
| Gln | Pro | Lys | Thr | Ala | Cys | Thr | Asn | Cys | Tyr | Cys | Lys | Lys | Cys | Cys | Phe |

|     |     |     | 20  |     |     |     | 25  |     |     |     | 30  |     |     |     |
|-----|-----|-----|-----|-----|-----|-----|-----|-----|-----|-----|-----|-----|-----|-----|

His Cys Gln Val Cys Phe Ile Thr Lys Ala Leu Gly Ile Ser Tyr Gly
                35                  40                  45

Arg Lys Lys Arg Arg Gln Arg Arg Pro Pro Gln Gly Ser Ser Met
        50                  55                  60

Ala Gly Ala Gly Arg Ile Tyr Tyr Ser Arg Phe Gly Asp Glu Ala Ala
65                      70                  75                      80

Arg Phe Ser Thr Thr Gly His Tyr Ser Val Arg Asp Gln Asp Arg Val
                85                  90                      95

Tyr Ala Gly Val Ser Ser Thr Ser Ser Asp Phe Arg Asp Arg Pro Asp
            100                 105                 110

Gly Val Trp Val Ala Ser Glu Gly Pro Glu Gly Asp Pro Ala Gly Lys
            115                 120                 125

Glu Ala Glu Pro Ala Gln Pro Val Ser Ser Leu Leu Gly Ser Pro Ala
    130                 135                 140

Cys Gly Pro Ile Arg Ala Gly Leu Gly Trp Val Arg Asp Gly Pro Arg
145                 150                 155                 160

Ser His Pro Tyr Asn Phe Pro Ala Gly Ser Gly Gly Ser Ile Leu Arg
                165                 170                 175

Ser Ser Ser Thr Pro Val Gln Gly Thr Val Pro Val Asp Leu Ala Ser
            180                 185                 190

Arg Gln Glu Glu Glu Gln Ser Pro Asp Ser Thr Glu Glu Pro
            195                 200                 205

Val Thr Leu Pro Arg Arg Thr Thr Asn Asp Gly Phe His Leu Leu Lys
    210                 215                 220

Ala Gly Gly Ser Cys Phe Ala Leu Ile Ser Gly Thr Ala Asn Gln Val
225                 230                 235                 240

Lys Cys Tyr Arg Phe Arg Val Lys Lys Asn His Arg His Arg Tyr Glu
            245                 250                 255

Asn Cys Thr Thr Thr Trp Phe Thr Val Ala Asp Asn Gly Ala Glu Arg
            260                 265                 270

Gln Gly Gln Ala Gln Ile Leu Ile Thr Phe Gly Ser Pro Ser Gln Arg
            275                 280                 285

Gln Asp Phe Leu Lys His Val Pro Leu Pro Pro Gly Met Asn Ile Ser
    290                 295                 300

Gly Phe Thr Ala Ser Leu Asp Phe
305                 310

( 2 ) INFORMATION FOR SEQ ID NO:28:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:28:

CTCCCATGGC TAGCAACACT ACACCC 26

( 2 ) INFORMATION FOR SEQ ID NO:29:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:29:

CTCCCATGGT ACCAGACACC GGAAACC                          27

( 2 ) INFORMATION FOR SEQ ID NO:30:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GGGGGATCCT CATATAGACA TAAATCC                          27

( 2 ) INFORMATION FOR SEQ ID NO:31:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 4
        ( D ) OTHER INFORMATION: /note="N in nucleotide position 4
        represents any nucleotide but is usuall..."

( i x ) FEATURE:
        ( A ) NAME/KEY: misc_feature
        ( B ) LOCATION: 9
        ( D ) OTHER INFORMATION: /note="N in nucleotide position 9
        represents any nucleotide but is usuall..."

( x i ) SEQUENCE DESCRIPTION: SEQ ID NO:31:

ACCNNNNNNG GT                                          12

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..4
        ( D ) OTHER INFORMATION: /note="Nucleotides 1-4 represent
        the 5'overhang of a BamHI-NcoI linker"

( x i ) SEQUENCE DESCRIPTION: SEQ ID NO:32:

GATCCTTTGC CGCCAC                                      16

( 2 ) INFORMATION FOR SEQ ID NO:33:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..4
        ( D ) OTHER INFORMATION: /note="Nucleotides 1-4 represent
        the 5'overhanging end of a BamHI-NcoI linker"

( x i ) SEQUENCE DESCRIPTION: SEQ ID NO:33:

```
CATGGTGGCG GCAAAG                                                              16
```

PAPILLOMAVIRUS E2 TRANS-ACTIVATION REPRESSORS

This application is a continuation of co-pending application Ser. No. 08/094,128, filed Sep. 24, 1993, which claims priority under 35 U.S.C. § 119 from PCT patent application PCT/US92/00652, filed Jan. 28, 1992, designating the United States, which is a continuation in part of U.S. application Ser. No. 07/646,998, filed Jan. 28, 1991, now issued as U.S. Pat. No. 5,219,990.

TECHNICAL FIELD OF INVENTION

This invention relates to E2 trans-activation repressors which interfere with normal functioning of the native full-length E2 transcriptional activation protein of the papillomavirus. Native full-length E2 trans-activation protein activates transcription of papillomavirus only through binding to DNA, and it binds to DNA only in the form of a pre-formed homodimer—a pair of identical polypeptide subunits held together by non-covalent interactions. The E2 trans-activation repressors of this invention are proteins, polypeptides or other molecules that dimerize with full-length native E2 polypeptides to form inactive heterodimers, thus interfering with the formation of active homodimers comprising full-length native E2 polypeptides, thereby repressing papillomavirus transcription and replication. The E2 trans-activation repressors of this invention are advantageously used in the treatment of papillomavirus infections and their associated diseases.

BACKGROUND ART

Papillomaviruses are a group of small DNA viruses that cause disease and pathological conditions in animals and humans. These tumorigenic viruses produce benign tumors or lesions which may, in some instances, develop into malignancies. Papillomaviruses have been implicated as a cause of cervical cancer, as well as other anogenital and epithelial malignancies.

Papillomaviruses consist of icosahedral particles containing protein and a single, circular, double-stranded DNA molecule averaging 7.8 kbp. To date, more than ten animal papillomaviruses and more than fifty-five human papillomaviruses have been identified (R. Sousa et al., "Control of Papillomavirus Gene Expression", *Biochimica et Biophysica Acta*, 1032, pp. 19–37 (1990); E. M. DeVilliers, "Heterogeneity of the Human Papillomavirus Group", *J. Virol.*, 63, pp. 4898–903 (1989)). One particularly studied papillomavirus is bovine papillomavirus ("BPV").

All known papillomaviruses encode similar proteins that perform analogous functions in infected cells. The E2 transcriptional activation protein ("the E2 protein") is a trans-acting factor that activates transcription through specific binding to cis-acting E2 enhancer sequences (i.e., E2 binding sites) in vital DNA (E. J. Androphy et al., "Bovine Papillomavirus E2 Trans-Activating Gene Product Binds to Specific Sites in Papillomavirus DNA", *Nature*, 324, pp. 70–73 (1987)). The 410 amino acid papillomavirus E2 protein has been shown to induce promoter expression in a classical enhancer mechanism (B. A. Spalholz et al., "trans-activation of a Bovine Papilloma Virus Transcriptional Regulatory Element by the E2 Gene Product", *Cell*, 42, pp. 183–91 (1985)). As with other transcription factors, the functions of E2 protein appear to be localized to discrete modular domains (I. Giri and M. Yaniv, "Structural and Mutational Analysis of E2 Trans-Activating Proteins of Papillomaviruses Reveals Three Distinct Functional Domains", *EMBO J.* 7 pp. 2823–29 (1988)).

Papillomavirus infections are non-lytic in their natural hosts, indicating that transcription and replication of the papillomavirus are tightly controlled. An upstream regulatory region ("URR") is found immediately 5' to the early genes of SPY and other papillomaviruses. The URR contains cis-acting regulatory signals, including an origin of DNA replication and several promoters that function in early gene transcription. The URR also contains enhancer elements that activate transcription from the URR promoters and heterologous promoters (Sousa et al., supra).

The E2 enhancer elements are conditional, in that they stimulate transcription only when activated by a protein encoded by a papillomavirus E2 open reading frame ("ORF"). Gene products from the E2 ORF include the full-length transcriptional activator E2 protein and at least two truncated versions of the E2 protein in BPV1 that function as transcriptional repressors. Transcriptional activation and repression of viral genes by E2 gene products constitute critical regulatory circuits in papillomavirus gene expression and DNA replication. E2 genes and DNA binding sites for E2 gene products appear to be characteristic of all papillomaviruses, although placement of the binding sites may vary Id.

Transcriptional regulation by the E2 protein depends on its direct binding to the nucleotide sequence 5'ACCNNNNNNGGT3' (SEQ ID NO: 31), which is found within cis-acting E2 enhancer elements in all papillomaviruses (Androphy et al., supra; Dartmann et al., "The Nucleotide Sequence and Genome Organization of Human Papilloma Virus Type 11", *Virology*, 151, pp 124–30 (1986); H. Hirochika et al., "Enhancers and Trans-Acting E2 Transcriptional Factors of Papillomaviruses", *J. Virol.*, 61, pp. 2599–606 (1987); P. Hawley-Nelson et al., "The Specific DNA Recognition Sequence of the Bovine Papillomavirus E2 Protein is an E2-Dependent Enhancer", *EMBO J.*, 7, pp. 525–31 (1988); A. A. McBride et al., "The Carboxy-Terminal Domain Shared by the Bovine Papillomavirus E2 Transactivator and Repressor Proteins Contains a Specific DNA Binding Activity", *EMBO J.*, 7, pp. 533–39 (1988)). In SEQ ID NO: 31, N represents any nucleotide; however nucleotide 4 of SEQ ID NO: 31 is usually G, and nucleotide 9 of SEQ ID NO: 31 is usually c. E2 binding sites appear to be positioned in close proximity to the viral promoters, with seventeen E2 binding sites being present throughout the bovine papillomavirus genome (R. Li et al., "Specific Recognition Nucleotides and their DNA Context Determine the Affinity of E2 Protein for 17 Binding Sites in the BPV-1 Genome", *Genes Dev.*, 3, pp. 510–26 (1989)). Enhancer elements containing E2 binding sites are found in the URR's of all papillomaviruses, as well as in other sites near promoters throughout the viral genome.

E2 binding sites may function as an element in viral DHA replication, as well as a classical transcriptional enhancer element. E2-mediated DNA binding, therefore, is essential for the natural life cycle of papillomaviruses.

European patent application 302,758 refers to the use of modified forms of E2 protein that bind to, and block, E2 binding sites on papillomavirus DNA without resulting in trans-activation. That application also refers to repression of E2 activation through the use of DNA fragments that mimic E2 binding sites, and thus bind with E2 trans-activators, making them unavailable for binding to E2 sites on the viral DNA.

E2 protein also binds the papillomavirus replication protein known as E1. It has been proposed that when an E2/E1 complex binds to an E2 binding site, replication of the viral genome occurs (M. Botchan et al., International Papillomavirus Workshop, Heidelberg, Germany (May 1990); Mohr et al., "Targeting the E1 Replication Protein to the Papillomavirus Origin of Replication by Complex Formation with the E2 Transactivator", *Science*, 250, pp. 1654–99 (1990)).

Full-length E2 transcriptional activator polypeptides (monomers) have a molecular weight of about 50 kD. Although amino acid sequence homology among E2 proteins of various papillomaviruses is low (ca. 35%), the E2 proteins share conserved motifs that constitute unique structural domains having distinct functions (Giri and Yaniv, supra).

The C-terminal domain of the E2 polypeptide is responsible for recognition of E2 binding sites on viral DNA. The N-terminal domain of the E2 polypeptide is responsible for transcriptional activation following binding of the protein to viral DNA (A. A. McBride et al., "E2 Polypeptides Encoded by Bovine Papillomavirus Type 1 Form Dimers Through The Common Carboxyl-Terminal Domain: trans-Activation is Mediated by the Conserved Amino Terminal Domain", *Proc. Natl. Acad. Sci. USA*, 86, pp. 510–14 (1989)). The E2 protein binds to viral DNA in vivo only in the form of a pre-existing homodimer Id. Dimeric E2 proteins exert control of papillomavirus promoters by directly binding to an inverted repeat that has been found in all such viruses.

In bovine papillomavirus models, and in some human papillomaviruses, at least two N-terminally truncated E2 proteins occur naturally and act as native repressors. It has been experimentally confirmed in vitro that truncated forms of E2 proteins which retain their ability to bind DNA but do not trans-activate, are competitive inhibitors of trans-activation-competent E2 polypeptides (P. F. Lambert et al., "A Transcriptional Repressor Encoded By BPV-1 Shares A Common Carboxy-Terminal Domain With The E2 Transactivator", *Cell*, 50, pp. 69–78 (1987); A. Stenlund and M. R. Botchan, "The E2 Trans-Activator Can Act as a Repressor by Interfering with a Cellular Transcription Factor", *Genes Dev.*, 4, pp. 123–36 (1990); J. Choe et al., "Bovine Papillomavirus Type 1 Encodes Two Forms of a Transcriptional Repressor: Structural and Functional Analysis of New Viral cDNAs", *J. Virol.*, 63, pp. 1743–55 (1989)). That inhibition has never been definitively attributed to competition for DNA binding sites, for E2 polypeptides in the dimerization process, or for both. It has been suggested that transcriptional repression occurs through direct competition with the native full-length, i.e., transcriptionally active E2 protein at the DNA binding site. PCT patent application WO89/12461 refers to peptide inhibitors of viral gene expression and viral replication. Those inhibitors are said to bind to trans-activator binding sites in viral DNA, thus blocking normal binding of native trans-activating proteins to those sites. And it has been suggested that formation of non-functional protein complexes could also prevent E2 activation of transcription (P. F. Lambert et al., supra).

Although it is known that papillomavirus E2 protein is the sequence-specific DNA binding protein that coordinates papillomavirus transcription, the structures of its DNA binding and dimerization motifs have never been determined. Both the DNA binding activity and the dimerization signal of the papillomavirus E2 trans-activation protein reside in the carboxy terminal 100 amino acids of the protein (McBride et al., supra). The C-terminal 100, 125 or 249 amino acids of E2 protein (each of which lacks trans-activation activity) all repress E2-dependent gene expression (T. Haugen et al., "Sequence-Specific and General Transcriptional Activation by the Bovine Papillomavirus-1 E2 Trans-Activator Require an N-Terminal Amphipathic Helix-Containing E2 Domain", *EMBO J.*, 7, pp. 4245–53 (1988)). Although the capacity for E2 dimerization, as well as the capacity for site-specific DNA binding, are known to reside in the C-terminal domain of the E2 polypeptide, the amino acid region within that domain responsible for E2 dimerization has not been identified (Giri and Yaniv, supra). To date, the dimerization function of the E2 polypeptide has not been separated from its DNA-binding function. Accordingly, repressors that inhibit papillomavirus transcription and replication by interfering with dimerization of native full-length E2 polypeptides have remained unknown.

DISCLOSURE OF THE INVENTION

By virtue of the present invention, the dimerization function of the E2 polypeptide has been separated from its DNA binding function. That separation has enabled, for the first time, the production of E2 trans-activation repressor polypeptides that are homologous to papillomavirus E2 polypeptides and which inhibit transcription and replication of papillomaviruses by interfering with dimerization of native full-length E2 polypeptides. These E2 trans-activation repressors advantageously exert their anti-viral effects by interfering with E2-protein-mediated enhancement of papillomavirus transcription in cells infected with that virus. The E2 trans-activation repressors of this invention are characterized by their ability to form inactive E2 heterodimers with full-length native E2 polypeptides produced by the papillomavirus and, therefore, to interfere with the formation of active homodimers by those polypeptides. By virtue of those abilities, the E2 trans-activation repressors reduce the availability of full-length native E2 polypeptides for formation of active homodimers, thus repressing papillomavirus transcription and replication.

According to one embodiment of this invention, E2 trans-activation repressors comprise at least the dimerization region, but less than the DNA binding domain, of the E2 polypeptide. Such repressors, which interfere with DNA binding by full-length E2 polypeptides through formation of inactive heterodimers and which comprise less than the DNA binding domain of the E2 polypeptide, by virtue of their reduced size, advantageously reduce the potential problem of repressor uptake into papillomavirus-infected cells. These repressors are useful in processes and compositions for treating papillomavirus infections.

This invention also relates to methods for isolating mutations in DNA encoding polypeptides that are homologous to native E2 polypeptides and which form inactive heterodimers with native full-length E2 polypeptides. Such mutations are useful in processes and compositions for the treatment of papillomavirus infections.

BRIEF DESCRIPTION OF THE DRAWINGS

FIG. 1 depicts the amino acid sequence of a segment of the wild type BPV1 E2 polypeptide between amino acids 285 and 410, which is the "DNA binding domain". Rectangles (and abbreviations immediately above the rectangles) indicate changes made in that amino acid sequence to produce E2 mutants (homologues), including the E2 trans-activation repressors of this invention.

FIGS. 2A and 2B tabulate the DNA binding, dimerization and repression activities of various E2 mutants prepared according to this invention.

FIGS. 3A, 3B and 3C show autoradiograms of electrophoresis gels from DNA binding ("gel shift") assays.

DETAILED DESCRIPTION OF THE INVENTION

Figures 4A, 4B:
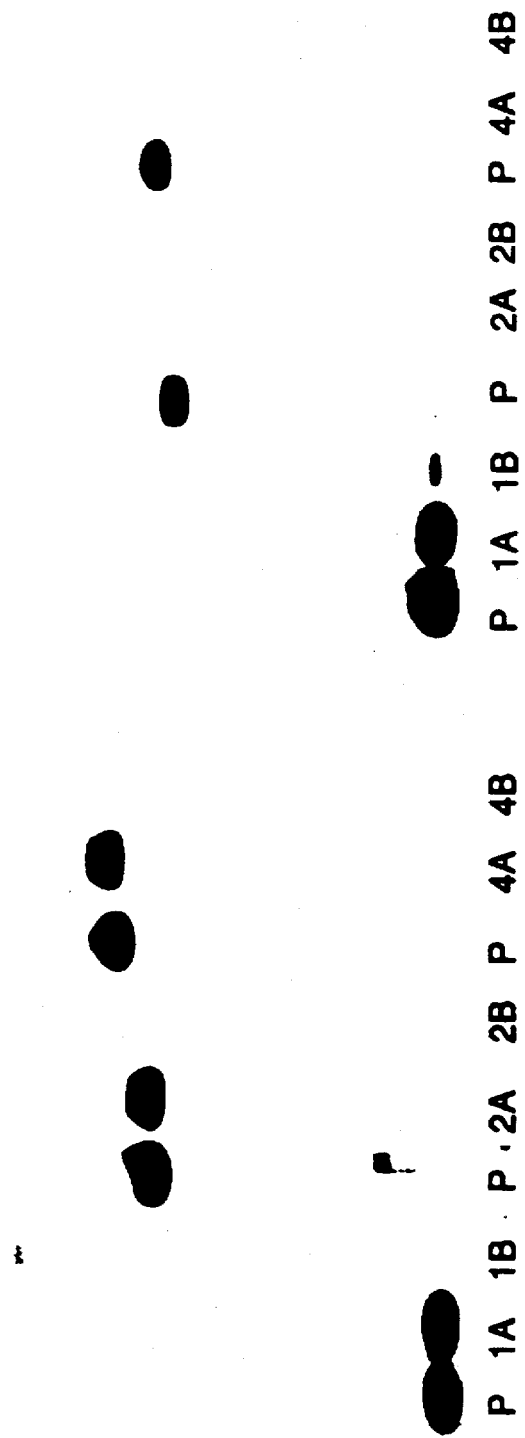
FIGS. 4A and 4B show autoradiograms of electrophoresis gels from a super-shift DNA binding assay performed with dimerization-defective mutant polypeptide 360S.

In order that the invention herein described may be more fully understood, the following detailed description is set forth.

In the description, the following terms are employed:

E2 trans-Activation Repressor—Any protein, polypeptide or other molecule that interferes with transcriptional activation of papillomavirus resulting from binding of full-length native E2 polypeptides in the form of pre-existing homodimers to E2 binding sites on DNA.

DNA Binding Domain—Amino acids 285–410 of BPV1 E2 protein, or the corresponding homologous region of an HPV E2 protein.

Native Minimal DNA Binding Domain—Amino acids 325–410 of BPV1 E2 protein, or amino acids 283–365 of HPV16 E2 protein, each amino acid sequence being sufficient for dimerization and binding to E2 DNA binding sites.

Homologous—An amino acid sequence very similar to at least a portion of the "DNA binding domain" but having at least one mutation therefrom, or a nucleic acid sequence encoding an amino acid sequence very similar to at least a portion of the "DNA binding domain" but having at least one mutation therefrom.

Homologue—A polypeptide or nucleic acid that is homologous to a native E2 polypeptide or a native E2 gene, respectively.

Mutant—Homologue or homologous.

Mutation—A substitution, insertion or deletion in a gene encoding a desired protein or polypeptide.

E2 Protein Dimerization Region—The region of the DNA binding domain that is necessary and sufficient for dimerization but not sufficient for binding of the dimer resulting from that dimerization to DNA.

Transport Moiety—Any covalent addition to an E2 trans-activation repressor that facilitates entry of that repressor into target cells.

Inactive Heterodimers—Dimers that comprise two non-identical polypeptide subunits and which do not bind to E2 binding sites on DNA.

Active homodimers—Dimers that comprise two identical E2 polypeptide subunits held together by non-covalent interactions and which cause transcriptional activation upon binding to E2 DNA binding sites.

Reporter Gene—A gene whose expression depends on the occurrence of a cellular event of interest and can be conveniently observed in a genetically transformed host strain.

Reporter Plasmid—A plasmid vector that comprises one or more reporter genes.

Reporter Strain—A genetically transformable unicellular host strain that comprises one or more reporter plasmids.

Amino Acid—A monomeric unit of a peptide, polypeptide or protein. The twenty protein amino acids (L-isomers) are: phenylalanine ("Phe" or "F"), leucine ("Leu", "L"), isoleucine ("Ile", "I"), methionine ("Met", "M"), valine ("Val", "V"), serine ("Ser", "S"), proline ("Pro", "P"), threonine ("Thr", "T"), alanine ("Ala", "A"), tyrosine ("Tyr", "Y"), histidine ("His", "H"), glutamine ("Gln", "Q"), asparagine ("Asn", "N"), lysine ("Lys", "K"), aspartic acid ("Asp", "D"), glutamic acid ("Glu", "E"), cysteine ("Cys", "C"), tryptophan ("Trp", "W"), arginine ("Arg", "R") and glycine ("Gly", "G").

As set forth in the examples of this application, E2 trans-activation repressors may be produced by random mutations and site-directed mutations in the C-terminal, 126-residue DNA binding domain of the E2 gene. Those mutations yielding functionally defective mutants or homologues of E2 polypeptides may be isolated following transformation of a unicellular host strain carrying an E2 trans-activation reporter plasmid. The isolated mutations may then be analyzed in terms of:

a) expression of a protein that is recognized by E2 antibodies and that has approximately the molecular weight (50 kD) expected for a full-length native E2 polypeptide;

b) nucleotide sequence of the mutated region of the E2 gene—the region of the E2 gene that encodes the DNA binding domain—which is in the C-terminal region of the E2 polypeptide;

c) capacity of the mutant (homologous) polypeptide corresponding to the C-terminal region of the native E2 polypeptide, to bind to E2 DNA binding sites;

d) capacity of the mutant (homologous) polypeptide corresponding to the C-terminal region of the native E2 polypeptide, to dimerize with itself;

e) capacity of the mutant (homologous) polypeptide corresponding to the C-terminal region of the native E2 polypeptide, to repress E2-dependent trans-activation in eukaryotic cells.

By virtue of this invention, for the first time, the E2 protein dimerization region—the region of the amino acid sequence in the E2 DNA binding domain that is responsible for dimerization independent of DNA binding interactions—was located between amino acids 325 and 410 of the native E2 protein. In addition, it was recognized that the E2 protein dimerization region itself is sufficient to repress trans-activation by full-length E2 proteins and that DNA binding is not required for repression of E2 trans-activation. Further, it was discovered that several mutations in the E2 amino acid sequence abolish DNA binding without abolishing dimerization.

According to one embodiment of this invention, an E2 trans-activation repressor comprises a polypeptide having an amino acid sequence homologous to the E2 DNA binding domain (SEQ ID NO: 1), or homologous to a polypeptide fragment thereof, said polypeptide being capable of forming inactive heterodimers with the full-length native E2 polypeptides produced by the papillomavirus and said inactive heterodimers being incapable of binding to E2 DNA binding sites. Alternatively, an E2 trans-activation repressor of this invention consists essentially of a polypeptide having an amino acid sequence homologous to the native E2 DNA binding domain (SEQ ID NO: 1), or homologous to a polypeptide fragment thereof, said polypeptide being capable of forming inactive heterodimers with the full-length native E2 polypeptide and said inactive heterodimers being incapable of binding to E2 DNA binding sites.

In another embodiment of this invention, an E2 trans-activation repressor comprises a polypeptide that is a fragment of the native E2 DNA binding domain. Alternatively, an E2 trans-activation repressor of this invention consists essentially of a polypeptide that is a fragment of the native E2 DNA binding domain.

In another embodiment of this invention, an E2 trans-activation repressor comprises an amino acid sequence selected from the group consisting of the amino acid sequence defined by SEQ ID NO: 3, the amino acid sequence defined by SEQ ID NO: 5, the amino acid sequence defined by SEQ ID NO: 7, the amino acid sequence defined by SEQ ID NO: 9, the amino acid sequence defined by SEQ ID NO: 11, the amino acid sequence defined by SEQ ID NO: 13, the amino acid sequence defined by SEQ ID NO: 15, the amino acid sequence defined by SEQ ID NO: 23, and the amino acid sequence defined by SEQ ID NO: 25. E2 trans-activation repressors of this invention may also consist essentially of any one of those amino acid sequences.

It should be understood that this invention also relates to E2 trans-activation repressors other than those defined by SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 23 and SEQ ID NO: 25. More particularly, E2 trans-activation repressors according to this invention include polypeptides comprising fragments of the E2 DNA binding domain or amino acid sequences homologous to the E2 binding domain, so long as those polypeptides demonstrate the capacity to repress E2 trans-activation by interfering with formation of active E2 homodimers.

The E2 trans-activation repressors of this invention may be chemically synthesized by conventional peptide synthesis techniques, such as solid phase synthesis (R. B. Merrifield, "Solid Phase Peptide Synthesis. I. The Synthesis Of A Tetrapeptide", *J. Am. Chem. Soc.*, 83, pp. 2149–54 (1963)). Alternatively, they may be prepared in appropriate hosts transformed with DNA sequences that code for the desired E2 trans-activation polypeptide. For example, an E2 trans-activation repressor of this invention may be prepared in a process comprising the steps a) culturing appropriate hosts that have been transformed with and which express a DNA sequence encoding that polypeptide; and b) recovering the E2 trans-activation repressor from the culture.

E2 trans-activation repressors according to this invention may also be produced by truncating a full-length native E2 gene, or a portion thereof, at various positions to encode a polypeptide that is a fragment of the native E2 binding domain and that comprises the E2 dimerization region, but lacks sequences necessary for DNA binding. For example, a papillomavirus E2 gene may be truncated so as to encode a polypeptide consisting of a sequence beginning between about amino acid 338 and amino acid 360, and ending at about amino acid 410. Such truncation of the full-length native E2 gene, or a portion thereof, may be accomplished by conventional techniques involving restriction digestion and oligonucleotide linkers, or by exonuclease digestion. A combination of such methods may also be employed to design E2 repressors other than those illustrated herein.

When an E2 trans-activation repressor of this invention is produced by expression in a unicellular host transformed with a DNA sequence encoding the repressor, the DNA sequence should be operatively linked to an expression control sequence in an appropriate expression vector and employed in that vector to transform an appropriate unicellular host. Such operative linking of a DNA sequence encoding an E2 trans-activation repressor of this invention to an expression control sequence, of course, includes the provision of a translation start signal in the correct reading frame upstream of that DNA sequence. If the particular DNA sequence to be expressed does not begin with a methionine, the start signal will result in an additional amino acid—methionine—being located at the N-terminus of the product. While such methionyl-containing E2 trans-activation repressors may be employed directly in the compositions and methods of this invention, it is usually more desirable to remove the methionine before use. Methods are available in the art to remove such N-terminal methionines from polypeptides expressed with them. For example, certain hosts and fermentation conditions permit removal of substantially all of the N-terminal methionine in vivo. Other hosts require in vitro removal of the N-terminal methionine. Such in vivo and in vitro methods are well known in the art.

A wide variety of host/expression vector combinations may be employed in expressing DNA sequences encoding the E2 trans-activation repressors of this invention. Useful expression vectors, for example, may consist of segments of chromosomal, non-chromosomal and synthetic DNA sequences, such as various known derivatives of SV40 and known bacterial plasmids, e.g., plasmids from *E. coli*, including col E1, pCR1, pBR322, pMB9, pET-3A and their derivatives, wider host range plasmids, e.g., RP4, phage DNAs, e.g., the numerous derivatives of phage λ, e.g., NM989, and other DNA phages, e.g., M13 and filamentous single-stranded DNA phages, yeast plasmids, such as the 2µ plasmid or derivatives thereof, and vectors derived from combinations of plasmids and phage DNAs, such as plasmids which have been modified to employ phage DNA or other expression control sequences. For animal cell expression, we prefer to use plasmid pJOD, which contains the adenovirus major late promoter augmented by the presence of the SV40 enhancer (J. Barsoum, "Introduction of Stable High Copy Number DNA into Chinese Hamster Ovary Cells by Electropotation", *DNA and Cell Biol.*, 9, pp. 293–300 (1990)).

In addition, any of a wide variety of expression control sequences—sequences that control the expression of a DNA sequence when operatively linked to it—may be used in these vectors to express DNA sequences encoding the E2 trans-activation repressors of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. For animal cell expression, we prefer to use an expression control sequence derived from the adenovirus major late promoter augmented by the presence of the SV40 enhancer.

A wide variety of unicellular host cells are also useful in expressing DNA sequences encoding the E2 trans-activation repressors of this invention. These hosts may include well known eukaryotic and prokaryotic hosts, such as strains of *E. coli*, Pseudomonas, Bacillus, Streptomyces, Saccharomyces and other fungi, animal cells, such as Chinese hamster ovary ("CHO") and mouse cells in culture, African green monkey cells, such as COS 1, COS 7, BSC 1, BSC 40, and BMT 10, insect cells in culture, human cells in culture and plant cells in culture. For animal cell expression, we prefer CHO cells.

It should of course be understood that not all vectors and expression control sequences will function equally well to express DNA sequences encoding the E2 trans-activation repressors of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered, as the vector must replicate in it. The vector's copy number, the ability to control that copy number and the expression of any other proteins encoded by the vector, such as antibiotic markers, should also be considered.

In selecting an expression control sequence, a variety of factors should also be considered. These include, for example, the relative strength of the system, its controllability and its compatibility with the DNA sequence encoding the particular E2 trans-activation repressor of this invention, particularly with respect to potential secondary structures. Unicellular hosts should be selected by consideration of their compatibility with the chosen vector, any potential toxicity of the product coded for on expression by the DNA sequences of this invention to them, their secretion characteristics, their ability to fold proteins correctly, their fermentation requirements and the ease of purification of the products coded for on expression by DNA sequences encoding the particular E2 trans-activation repressor of this invention.

The E2 trans-activation repressor polypeptides produced on expression of the DNA sequences of this invention may be isolated from the fermentation or animal cell cultures and purified using any of a variety of conventional methods. One of skill in the art may select the most appropriate isolation and purification techniques without departing from the scope of this invention.

E2 trans-activation repressors according to this invention also include non-peptide chemicals—peptidomimetics—which are capable of specifically forming an inactive complex with native full-length E2 polypeptides so as to prevent them from forming active homodimers and thereby blocking papillomavirus transcription and translation. And molecules that form a stable complex with E2 polypeptides so as to prevent them from forming active homodimers may be designed on the basis of three-dimensional data on the E2 dimerization domain. Three-dimensional data on the E2 dimerization domain may be obtained by X-ray crystallography.

The structural motif represented in BPV1 by amino acids 333 through 344 of the E2 protein is highly conserved among papillomaviruses, including human papillomaviruses (Giri and Yaniv, supra). Several papillomavirus E2 repressors of this invention comprise mutations in that highly conserved motif. It should be understood that the BPV1-derived E2 trans-activation repressors of this invention are useful in the treatment of human papillomavirus infections. It should be further understood that the illustrative processes for the production of E2 trans-activation repressors from the bovine papillomavirus, BPV1, described in this application, may similarly be employed to produce E2 trans-activation repressors from human papillomaviruses, as demonstrated in Example 7.

The processes and compositions of this invention may be used to treat any mammal, including humans. According to this invention, mammals are treated by the pharmaceutically acceptable administration of an E2 trans-activation repressor in a pharmaceutically effective amount and for a period of time sufficient to inhibit or lessen the spread of papillomavirus infection, to reduce the symptoms of the specific papillomavirus-associated disease, or to prevent their recurrence.

Diseases which may be treated by the processes and compositions of this invention are those caused by the etiological agent, papillomavirus. Such diseases include, for example, epithelial malignancies, anogenital malignancies, such as cervical cancer, malignant lesions, benign lesions, papillomacarcinomas, papilloadenocystomas, papilloma neurophathicum, papillomatosis, cutaneous and mucosal papillomas, condylomas, oral, pharyngeal, laryngeal, and tongue papillomas, fibroblastic tumors and other pathological conditions associated with papillomavirus. The E2 trans-activation repressors of this invention may also be used to treat epithelial and internal fibropapillomas in animals. In addition, the methods and compositions of this invention may be used for the recidivism prophylaxis of solid tumors.

According to this invention, E2 trans-activation repressors may be in any pharmaceutically acceptable dosage form, including those which may be administered intratumorally, peritumorally, interlesionally, intravenously, intramuscularly, subcutaneously or periolesionally, or by topical routes, to exert local therapeutic effects.

Such dosage forms may include pharmaceutically acceptable carriers and adjuvants which are known to those of skill of the art. These carriers and adjuvants include, for example, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogenphosphate, sodium chloride, zinc salts, colloidal silica, magnesium trisilicate, polyvinyl pyrrolidone, cellulose-based substances and polyethylene glycol. Adjuvants for topical or gel base forms of E2 trans-activation repressors may, for example, be selected from the group consisting of sodium carboxymethylcellulose, polyacrylates, polyoxyethylene-polyoxypropylene-block polymers, polyethylene glycol and wood wax alcohols. For all administrations, conventional depot forms may be used.

The pharmaceutical compositions of this invention may be formulated using conventional methods to prepare pharmaceutically useful compositions. Such compositions preferably include at least one pharmaceutically acceptable carrier. See, e.g., *Remington's pharmaceutical Sciences* (E. W. Martin). In addition, the compositions preferably include a pharmaceutically acceptable buffer, preferably phosphate buffered saline, together with a pharmaceutically acceptable compound for adjusting isotonic pressure, such as, for example, sodium chloride, mannitol or sorbitol.

Pharmaceutical compositions according to this invention may include one or more E2 trans-activation repressors as active ingredients. Alternatively, a composition containing one E2 trans-activation repressor may be administered to a patient in combination with, or sequentially with, a composition containing a different E2 trans-activation repressor.

The most effective mode of administration and dosage regimen of the E2 trans-activation repressor will depend upon the type of disease to be treated, the severity and course of that disease, previous therapy, the patient's health status and response to the E2 repressor and the judgment of the treating physician. The E2 repressor may be administered to the patient at one time or over a series of treatments.

According to one embodiment of this invention, papillomavirus-infected cells may be saturated with an E2 trans-activation repressor which forms inactive heterodimers with the native full-length E2 polypeptides produced by that virus, to interfere with the formation of active homodimers comprising native full-length E2 polypeptides, thus repressing viral transcription and replication.

Depending on the severity of the papillomavirus infection or its associated disease, for parenteral regimens, a dose of between about 1 and 1000 mg/kg body weight of the E2 trans-activation repressor may be administered to the patient, via one or several administrations, or released from a depot form per treatment. Alternatively, a dose of between about 1 and 1000 µg/ml of the E2 trans-activation repressor may be administered to a patient per application via topical routes.

According to an alternate embodiment of this invention, an E2 trans-activation repressor may be administered serially or in combination with other therapeutics used in the treatment of papillomavirus infections or diseases caused by them. Such therapeutics include interferons, such as IFN-γ, IFN-α and IFN-β derived from natural sources or produced by recombinant techniques, other cell mediators formed by leukocytes or produced by recombinant techniques such as for example, interleukin-1, interleukin-2, tumor necrosis factor, macrophage colony stimulating factor, macrophage migration inhibitory factor, macrophage activation factor, lymphotoxin and fibroblast growth factor. Alternatively, the E2 trans-activation repressor may be administered serially or in combination with conventional therapeutic agents or regimens such as, for example, salicylic acid, podophyllotoxin, retinoic acid, surgery, laser therapy and cryotherapy. Such combination therapies may advantageously utilize less than conventional dosages of those agents, or involve less radical regimens, thus avoiding any potential toxicity or risks associated with those therapies.

The E2 trans-activation repressors of this invention may be delivered to papillomavirus-infected cells either directly or indirectly. Direct delivery of E2 trans-activation repressors may be facilitated by chemical modification of the polypeptides themselves. One such modification involves increasing the lipophilicity of the E2 trans-activation repressor in order to increase binding to the cell surface, in turn, stimulating non-specific endocytosis of the protein. Lipophilicity may be increased by adding a lipophilic moiety (e.g., one or more fatty acid molecules) to the E2 repressor. A wide variety of fatty acids may be employed. For example, the protein may be palmitoylated. Alternatively, a lipopeptide may be produced by fusion or cross-linking, to permit the E2 repressor to resemble the natural lipopeptide from *E. coli*, tripalmitoyl-S-glycerylcysteil-seryl-serine, at its amino terminus. This lipopeptide has been shown to increase the uptake of fused peptides (P. Hoffmann et al., "Stimulation Of Human And Murine Adherent Cells By Bacterial Lipoprotein And Synthetic Lipopeptide Analogues", *Immunobiol.*, 177, pp. 158–70 (1988)). Lipophilicity may also be increased by esterification of the protein at tyrosine residues or other amino acid residues. And uptake of the E2 trans-activation repressor may be increased by addition of a basic polymer such as polyarginine or polylysine (W. C. Shen and H. J. P. Ryser, "Conjugation Of Poly-L-Lysine Albumin And Horseradish Peroxidase: A Novel Method Of Enhancing The Cellular Uptake Of Proteins", *Proc. Natl. Acad. Sci USA*, 75, pp. 1872–76 (1978)).

Because some uptake mechanisms for E2 trans-activation repressors may involve passage through lysosomes and since long half-life in the target cells is desirable, an E2 trans-activation repressor of this invention may be modified to increase its protease resistance and, in turn, the half-life of the polypeptide in circulation and cells. In one embodiment of the present invention, the protease resistance of an E2 trans-activation repressor is increased by incorporation of D-amino acids instead of L-amino acids at some or all residues of the polypeptide. In another embodiment, the amino terminus, or carboxy terminus, or both termini of an E2 repressor are blocked by chemical modification. In a further embodiment of this invention, lysosomal proteases are inhibited by an E2 trans-activation repressor in a composition comprising a lysomotrophic agent, such as chloroquine, amantadine, monensin, methylamine, or ammonium chloride.

Direct delivery of E2 trans-activation repressors according to this invention may also be effected by the use of transport moieties, such as protein carriers known to cross cell membranes. For example, an E2 trans-activation repressor may be fused to a carrier protein, preferably by a genetic fusion which may be expressed in a system such as *E. coli* or yeast. According to one embodiment of this invention, the amino terminus of the E2 trans-activation repressor may be fused to the carboxy terminus of a transport moiety using standard techniques.

Nucleotide sequences encoding such carrier-E2 trans-activation repressor fusion proteins, operatively linked to regulatory sequences, may be constructed and introduced into appropriate expression systems using conventional recombinant DNA procedures. The resulting fusion protein may then be purified and tested for its capacity to (1) enter intact eukaryotic cells and (2) inhibit E2-dependent gene expression and viral DNA replication once inside the intact eukaryotic cells.

In choosing a useful carrier protein, those of skill in the art will recognize the desirability of appropriate control experiments designed, inter alia, to test the possibility that the carrier portion of the fusion protein itself interacts with elements of the E2 transcriptional regulation system. If the carrier portion of the fusion protein is found to have undesirable interactions, such as activation of E2-dependent enhancer elements, the portions of the carrier sequence responsible for these interactions should be identified and deleted in a way which permits the sequence to retain its carrier capacity. Alternately, one of several conventional carrier sequences which do not interact with elements of the E2 transcriptional regulation system can be substituted.

Useful carrier proteins include, for example, bacterial hemolysins or "blending agents", such as alamethicin or sulfhydryl activated lysins. Other carrier moieties which may be used include cell entry components of bacterial toxins, such as Pseudomonas exotoxin, tetanus toxin, ricin toxin, and diphtheria toxin. Also useful is melittin, from bee venom. Other useful carrier proteins include proteins which are viral receptors, cell receptors or cell ligands for specific receptors that are internalized, i.e., those which cross mammalian cell membranes via specific interactions with cell surface receptors. Such cell ligands include, for example, epidermal growth factor, fibroblast growth factor, transferrin and platelet-derived growth factor. Alternatively, the ligand may be a non-peptide, such as mannose-6-phodphate, which permits internalization by the mannose-6-phosphate receptor. The transport moiety may also be selected from bacterial immunogens, parasitic immunogens, vital immunogens, immunoglobulins or fragments thereof that bind to target molecules, cytokines, growth factors, colony stimulating factors and hormones. A transport moiety may also be derived from the tat protein of HIV-1.

As an alternative or addition to the above-described chemical modifications and protein carriers, which may be employed alone or in combination, other agents which allow penetration of the keratinized cell layer may be employed to facilitate delivery of the E2 trans-activation repressors of this invention to papillomavirus-infected cells. In topical applications, for example, the E2 trans-activation repressor may be administered in combination with dimethylsulfoxide, an agent which promotes penetration of cell membranes by substances mixed with it. Useful keratinolytic agents include, for example, salicylic acid, urea, and α-hydroxyacids. For such applications, the E2 trans-activation repressor and any other agent may be administered topically, in cream or gel form.

Indirect delivery of an E2 trans-activation repressor to papillomavirus-infected cells may be carried out by delivering a gene encoding an E2 trans-activation repressor, with appropriate expression control sequences, into those cells. A gene encoding an E2 trans-activation repressor may be introduced into target cells by treating the infected cells, for example, by scraping them to allow uptake of DNA, by electropotation, by direct injection, or through the use of defective recombinant viruses, such as retroviruses. For example, a DNA sequence encoding an E2 trans-activation repressor may be introduced into target cells using a retrovirus by transcribing the DNA sequence encoding an E2 trans-activation repressor into an RNA sequence and incorporating the resulting RNA sequence into a defective recombinant retrovirus.

In order that the invention described herein may be more fully understood, the following examples are set forth. It should be understood that these examples are for illustrative purposes only and are not to be construed as limiting this invention in any manner. Throughout these examples, all molecular cloning reactions were carried out according to methods in T. Maniatie et al., *Molecular Cloning: A Laboratory Manual,* Cold Spring Harbor Laboratory (1982) or J. Sambrook et al., *Molecular Cloning—A Laboratory Manual,* Cold Spring Harbor Laboratory (1982) or J. Sambrook et al., *Molecular Cloning—A Laboratory Manual.* 2nd Ed., Cold Spring Harbor Press (1989), using enzymes obtained from New England Biolabs (Beverly, Mass.), except where otherwise noted. We confirmed the integrity of all plasmid constructions by DNA sequencing.

EXAMPLE 1

Chemical Mutagenesis, phenotypic Selection Of Mutants And Site-Directed Mutagenesis We cloned the full-length coding strand of the wild type BPV1 E2 gene from plasmid pCO-E2 (Hawley-Nelson et al., supra) into the filamentous single-stranded DNA bacteriophage M13 strain mp18 (Life Technologies, Inc., Gaithersburg, Md.) and isolated single-stranded DNA for chemical mutagenesis of the E2 protein DNA binding domain. See Chapter 4 of Sambrook et al., supra, for standard procedures pertaining to the use of bacteriophage M13.

In summary, in order to generate a large number of mutants, we chemically mutagenized and reverse-transcribed one strand of the BPV1 E2 gene, transferred the double-stranded segment into a wild type E2 yeast expression vector and isolated mutants that were limited in gene induction. Random mutations in the DNA encoding the 126-residue C-terminal DNA binding domain of the E2 protein were produced by chemical mutagenesis, essentially according to the method of R. M. Myers et al., "A General Method for Saturation Mutagenesis of Cloned DNA Fragments", *Science,* 229, pp. 242–47 (1985). The method of Myers et al., supra, involves brief exposure of single-stranded DNA to chemicals such as nitrous acid, formic acid, hydrazaine, or potassium permanganate, that damage all four bases without damaging the phosphodiester backbone of the DNA.

More specifically, we treated 20 μg of single-stranded M13 DNA containing the full-length E2 gene with 1.3 mM potassium permanganate for between about 5 and 10 min. In a variation of the procedure, we treated the single-stranded DNA with 12 M formic acid for between about 5 and 10 min. With either chemical reagent, we carried out the reaction at room temperature and stopped it by addition of 1/10 volume of 2.5 M sodium acetate (pH 7.0). We separated the chemically modified, single-stranded DNA from the reaction mixture by precipitating it twice with cold ethanol in the presence of yeast tRNA carrier. We further purified the chemically modified DNA by agarose gel electrophoresis.

For second strand synthesis, we annealed synthetic oligonucleotide primers complementary to the single-stranded DNA 3' to the BstX1 site which is at nucleotide 3881 in the 3' non-coding region of the BPV1 E2 gene. Any portion of this region may be used for priming, and the exact length of the primer is not critical—so long as the primer is of a sufficient length to form a stable duplex. Conditions for annealing of primers and techniques of primer extension are well known in the art. We used a primer having the sequence 5' AGCAACTAGTCCCAAG 3', (SEQ ID NO: 17) which is complementary to nucleotides 3904 to 3919 of BPV1. For primer extension, we used T7 polymerass (Sequenase 2.0, U.S. Biochemicals, Cleveland, Ohio). The primer extension reaction was carried out at 37° C. for about 1 hr, in the presence of all four dNTPs, according to the vendor's recommendations. Alternatively, we used murine leukemia virus reverse transcriptass (Life Technologies, Inc., Gaithersburg, Md.) at 40° C. for primer extension. When the polymerase used for second strand synthesis encountered a damaged base in the template strand, it incorporated any one of the four dNTPs. Random transitions and transversions, involving all four bases, were, therefore, likely to be produced at potentially any point in the nucleotide sequence. Thus, synthesis of the complementary DNA strand led to mutation at sites on the coding strand where chemical reaction took place.

We digested the primer extension products (i.e., double-stranded DNA) with restriction endonucleases KpnI and BstX1 to release a population of 426.bp randomly mutagenized E2 gene fragments encoding the C-terminal region of the E2 protein.

We purified the mutagenized fragments on an agarose gel and subcloned them into the wild type E2 gene in yeast expression vector pYE2 (Morrissey et al., Supra), replacing the corresponding wild type 426 bp KpnI-BstXI fragment with a mutagenized fragment. Plasmid pYE2 comprises a galactose upstream activating sequence ("GALUAS") and downstream restriction sites such that the GAL UAS can conveniently be used to drive expression of the homologous E2 sequences. Gene expression from GAL UAS is induced by the presence of galactose but strongly repressed by glucose. Thus, expression of the E2 sequences and E2 homologous sequences may be regulated by choice of yeast culture medium. In addition, plasmid pYE2 contains a ura gene, a selectable marker that permits growth of hosts on selective media lacking uracil.

FIG. 1 depicts the sequence of amino acids 285–410 of the wild type BPV1 E2 protein (E. Y. Chen et al., "The Primary Structure and Genetic Organization of the Bovine Papillomavirus Type 1 Genome", Nature, 299, 529–34 (1982)). This region of the BPV1 E2 protein is known as the DNA binding domain (Girl and Yaniv, supra). FIG. 1 also depicts changes in the amino acid sequence of the BPV1 E2 DNA binding domain which characterized various E2 transcription repressor mutants prepared according to this invention. As shown in FIG. 1, mutations were scattered throughout the DNA binding domain. Several of the dimerization defective E2 mutants were characterized by two or three nucleotide alterations from the native E2 protein sequence.

The cysteine at position 340 of the wild type E2 protein in FIG. 1 is present in all papillomavirus E2 proteins whose sequences are known. Furthermore, DNA binding activity of E2 protein is dependent on the presence of reducing agents. Accordingly, we generated mutations at position 340 in order to determine the criticality of that cysteine. We used site-directed mutagenesis to substitute the three other nucleotides for G and for C in the TGC codon for cysteine 340 in the BPV1 E2 gene. We performed the site-directed mutagenesis according to the method of Kunkel et al., "Rapid and Efficient Site-Specific Mutagenesis without Phenotypic Selection", Methods Enzymol. 154, pp. 367–82 (1987).

FIG. 2 identifies various E2 trans-activation repressor mutants prepared according to this invention and summarizes their DNA binding, dimerization and repression activities, as assayed in the following examples.

EXAMPLE 2

Screening Mutations By trans-activation Of A Reporter Gene In Yeast

We tested the E2 mutants for trans-activation of a reporter gene in an E2 trans-activation reporter strain. More specifically, we used pYE2, carrying the population of E2 mutations, to transform reporter strain BGW1-7A, a yeast strain which contained yeast reporter plasmid pBY-4 (Morrissey et al., supra). Plasmid pBY-4 contains a β-galactosidase reporter gene under the control of an E2-dependent promoter, plus a Leu2 gene, which serves as a selectable marker. Expression of the β-galactosidase gene in pBY-4 was rendered E2 dependent by having it under the control of an appropriately placed cyc-1 minimal promoter preceded upstream by four E2 binding sites. We then selected for transformants that contained both plasmids on a 2% glucose/minimal medium without leucine and uracil. Transfer of cells to glucose minimal medium lacking leucine and uracil provided strong positive selection pressure for transformants harboring both plasmid pYE2 and plasmid pBY-4, while leaving expression of E2 sequences uninduced.

Although not required, a step involving such selection pressure without expression of E2 sequences, immediately following transformation, is preferred, in order to exclude the possibility that expression of E2 protein or E2 homologues might confer a selective disadvantage that would discriminate against the desired transformants in a mixed population.

The colonies selected were then replica plated onto selective yeast minimal medium containing 100 mM potassium phosphate (pH 6.9), 2% galactose, and 0.004% X-gal. X-gal is a colorless β-galactosidase substrate (5-bromo-4-chloro-3-indolyl β-glucoside) that yields a blue product upon cleavage by β-galactosidase. Galactose induced expression of the E2 gene carried on pYE2 and X-gal gave a color indication of E2-dependent activity of the β-galactosidase gene carried on plasmid pBY-4. On media containing galactose and X-gal, transformants expressing trans-activating E2 homologues were blue, while colonies expressing non-activating homologues were light blue or white. After incubating the cultures for 48 hours at 30° C., we visually assayed colony color, on a scale of 1–8. Approximately 10–15% of the colonies were white or light blue. All E2 mutants listed in FIG. 2 were originally isolated as white or light blue colonies. White colonies harbored trans-activation-abolishing mutations, while light blue colonies harbored trans-activation-reducing mutations. Mutants 366Y/376L, 386W, 360S, 399I, 408*, 411*, and 3SLI were isolated as light blue colonies in the initial screening. The other mutants listed in FIG. 2 were isolated as white colonies. Dark blue colonies harbored either unmutated E2 sequences or E2 mutations that did not reduce E2 trans-activation, and thus were discarded.

The E2 plasmid, pYE2, was isolated from each mutant clone and the mutagenized E2 insert of each clone was sequenced by standard methods.

As detailed above in Example 1, the five mutants at cy8340 did not arise from our screen, but were generated by site-directed mutagenesis.

EXAMPLE 3

Expression of E2 Protein And E2 Homologues In Yeast And In E. coli

We analyzed the selected light blue or white transformants for expression of full-length E2 proteins as follows. Since mutations resulting in premature termination codons or unstable E2 proteins were not desired, we extracted total protein from cultures of the selected light blue and white colonies and tested that protein by standard immunoblot techniques. Only mutant clones that produced nearly wild-type levels of protein that reacted with E2 antibodies and that also had a molecular weight of about 50 kD were further characterized.

First, we cultured each of the selected light blue or white transformants in 50 ml of selective minimal medium containing 2% galactose, for 7 hrs at 30° C. To extract E2 proteins, we harvested the cells by centrifugation and washed them with protein extraction buffer (200 mM Tris/HCl (pH 8.0), 400 mM ammonium sulfate, 10 mM magnesium chloride, 1 mM EDTA and 10% glycerol (v/v)). We then suspended the washed cells in 2 volumes of protein extraction buffer supplemented with 5 mM DTT and the following protease inhibitors: 1 mM PMSF, 1 mM TLCK, pepstatin and 5 mM benzamidinehydrochloride.

After addition of washed 0.45 mm diameter glass beads (about equal in volume to the yeast cell pellet), we disrupted the yeast cells by vigorous vortexing 6 times, for 30 sec. each time. Heavy insoluble debris was removed by a first round of centrifugation and the supernatant clarified by centrifugation at about 13,000×g for 1 hr at 4° C. We added an equal volume of cold, saturated ammonium sulfate solution to the clarified supernatant and allowed proteins to precipitate on ice for 15 min. The precipitated proteins were pelleted by centrifugation in a fixed angle JA-17 rotor at 13000×g for 10 minutes at 4° C. and then dissolved in 50 μl of solubilization buffer (25 mM Tris/HCl (pH 8.0), 2 mM EDTA, 20% glycerol (v/v), 1 mM DTT and the same mixture of protease inhibitors used in the protein extraction buffer.

We expressed the C-terminal 126 amino acids (plus an N-terminal methionine residue) of the BPV1 E2 polypeptide and the corresponding mutant polypeptides (homologues) in the *E. coli* expression vector pETSC, as described by Studier, "Use of T7 RNA Polymerase to Direct Expression of Cloned Genes", *Methods Enzymol.*, 185, pp. 60–90 (1990), after creating a KpnI site immediately 3' to the NcoI site and ATG codon. Mutant E2 sequences were then transferred into pETSC-E2 as KpnI-BstX1 fragments. The pETSC-E2 expression vectors were induced to express the E2 homologues as described by Studier (supra), following transformation of the expression host *E. coli* strain BL21 (DE3)pLYSS (Studier, Supra). We produced 50 ml cultures of the transformed expression host strain grown under inducing conditions and harvested the cells by centrifugation.

The harvested cells were suspended in 4 ml of 20 mM MES (pH 6.0) containing 1 mM PMSF and subjected to freeze-thaw lysis. Insoluble debris was removed by centrifugation. The E2 polypeptides and E2 homologues were partially purified by chromatography on S-Sepharose (Pharmacia-LKB, Piscataway, N.J.). We applied the protein solution to a 0.2 ml column of S-Sepharose that had been pre-equilibrated with the freeze-thaw lysis buffer. The column was washed with 20 mM MES (pH 6.0), 100 mM NaCl, 5 mM DTT and 1 mM EDTA. E2 polypeptides and E2 homologues were then eluted from the column with a solution containing 20 mM MES (pH 6.0), 600 mM NaCl, 5 mM DTT, 1 mM EDTA, 10% glycerol (v/v), 1 mM PMSF, 1 μM pepstatin, 2 μg/ml leupeptin and 2 μg/ml aprotinin. As described below, we then tested for the presence E2 homologues in the eluate by conventional immunoblot procedures, which may be carried out by those of ordinary skill in the art using standard techniques.

We resolved proteins in the eluate according to molecular weight by SDS polyacrylamide gel electrophoresis. Following electrophoresis, we transferred the resolved proteins onto nitrocellulose membranes by standard blotting techniques. We then treated the nitrocellulose membranes with bovine serum albumin to saturate non-specific protein binding sites on the membrane and exposed the membrane to polyclonal rabbit anti-E2 serumat a serum dilution of 1:2500, for 2 hours, at room temperature. After washing the membrane to remove unbound antibodies, we visualized antibodies bound to electrophoretic protein bands via alkaline phosphatase conjugated to antibodies that bind to rabbit immunoglobulins.

EXAMPLE 4

DNA Binding Assays

In order to determine which mutant E2 polypeptides (homologues) bound to E2 DNA binding sites, we carried out DNA binding assays.

We first mixed between about 0.5 and 4.0 μl of partially purified E2 polypeptides or homologues, at a concentration of about 1 ng/μl (prepared as described in Example 3 above) with about 1.5 μg of poly dI-dC and about 300 ng of sheared salmon sperm DNA, in a total volume of about 20 μl, for 10 min. at 4° C. We then added between about 0.5 and 2.0 ng of end-labelled DNA fragments (about 10,000 cpm/reaction) containing one, two or four E2 DNA binding sites and placed the mixture on ice. The DNA fragments (probes) containing E2 binding sites consisted of NsiI restriction fragments from pBY-1 (one E2 binding site), pBY-2 (two E2 binding sites), or pBY-4 (Morrissey et al., supra). After 30 minutes, we added 1/10 volume of 20 mM Hepes (pH 7.5), 20% glycerol (v/v) and 0.25% bromophenol blue to the DNA-protein mixture, for electrophoresis. We then resolved DNA-protein complexes from unbound DNA and protein by electrophoresis in 4–5% polyacrylamide gels for about 3–4 hours, at 150 v. The electrophoresis buffer was 0.5×TBE. Following electrophoresis, gels were dried and exposed to X-ray film. Our DNA binding assay was in accord with well-known methods (see generally: F. Ausubel et al., "Mobility Shift DNA Binding Assay Using Gel Electrophoresis", in *Current Protocols in Molecular Biology*, pp. 12.2.1–12.2.10 (1988)).

FIG. 3 shows autoradiograms of electrophoresis gels from these DNA binding "gel shift" assays. As depicted in that figure, the sample in each lane included radioactive DNA probe containing E2 binding sites. The DNA in panels A and B contained two E2 binding sites, and the DNA in panel C contained 4 DNA binding sites. Sample designations are as follows: "P", radioactive DNA probe containing E2 binding sites, in the absence of added protein; "wt", native E2 repressor; "333"7, mutant polypeptide 333V; "337", mutant polypeptide 337L; "339", mutant polypeptide 339M; "344", mutant polypeptide 344L; "360", mutant polypeptide 360S; "316", mutant polypeptide 316Y; "370", mutant polypeptide 370I; "340R", "340F", "340Y", "340S", "340G" and "3SLI" refer to mutant polypeptides having those designations. The basis of the assay is that protein bound to the DNA probe slows electrophoretic migration of the DNA. Thus, binding of protein to the DNA causes the DNA band to be "shifted" from its electrophoretic position observed in the absence of bound protein. FIG. 3 shows that mutant polypeptides 333V, 337L, 339M, 344L, 340F, 340R, 340Y and 360S did not "shift" the electrophoretic position of the DNA probe, and thus they did not bind to the E2 binding sites on the DNA probe. Mutants 333V, 337L, 339M, 344L, 340R, 340Y, 340F, 360S all failed to stably bind the E2 DNA element in this gel-shift assay.

To further characterize homologues that were dimerization defective, we performed super-shift DNA binding assays, using monoclonal antibodies to BPV1 E2 protein. The super-shift assays were carried out to determine whether dimerization defective E2 homologues would bind to E2 DNA binding sites when held together in pairs by monoclonal antibodies, to simulate dimerization. In the super-shift assays, we first incubated the E2 homologues on ice with between about 2 to 4 μl of culture medium (DulBecco's modified medium with 10% fetal calf serum) from a monoclonal antibody-producing hybridoma cell culture, for 30 min., before addition of labelled DNA. We then placed the mixture on ice. After 30 min., we added 1/10 volume of 20 mM Hepes (pH 7.5), 20% glycerol (v/v) and 0.25% bromophenol blue to the DNA-protein-antibody mixture, for electrophoresis. Electrophoresis was as in the DNA binding assay described above.

FIG. 4 shows autoradiograms of electrophoresis gels from a super-shift DNA binding assay performed with dimerization-defective mutant polypeptide 360S. In that figure, Gel A shows that in the absence of anti-E2 monoclonal antibody, mutant polypeptide 360S did not bind to DNA probes having 1, 2 or 4 E2 binding sites. Gel B shows that in the presence of anti-E2 monoclonal antibody, however, mutant polypeptide 360S did exhibit binding to DNA probes having 2 or 4 E2 binding sites. Gel A samples were as follows: "1P", DNA probe with one E2 binding site, in the absence of added protein; "1A", DNA probe with one E2 binding site, in the presence of mutant polypeptide 360S; "1B", DNA probe with one E2 binding site, in the presence of native E2 repressor; "2P", DNA probe with two E2 binding sites, in the absence of added protein; "2A", DNA probe with two E2 binding sites, in the presence of mutant polypeptide 360S; "2B", DNA probe with two E2 binding sites, in the presence of native E2 repressor; "4P", DNA probe with four E2 binding sites, in the absence of added protein; "4A", DNA probe with four E2 binding sites, in the presence of mutant polypeptide 360S; "4B", DNA probe with four E2 binding sites, in the presence of native E2 repressor. Gel B samples were as follows: "1P", DNA probe with one E2 binding site, in the absence of added protein; "1A", DNA probe with one E2 binding site, in the presence of mutant polypeptide 360S and monoclonal antibody; "1B", DNA probe with one E2 binding site, in the presence of native E2 repressor and monoclonal antibody; "2P", DNA probe with two E2 binding sites, in the absence of added protein; "2A", DNA probe with two E2 binding sites, in the presence of mutant polypeptide 360S and monoclonal antibody; "2B", DNA probe with two E2 binding sites, in the presence of native E2 repressor and monoclonal antibody; "4P", DNA probe with four E2 binding sites, in the absence of added protein; "4A", DNA probe with four E2 binding sites, in the presence of mutant polypeptide 360S and monoclonal antibody; "4B", DNA probe with four E2 binding sites, in the presence of native E2 repressor and monoclonal antibody.

In the initial screening of mutants for loss of E2 trans-activation, we noted that while mutant 360S was unable to activate the promoters with one or two E2 binding sites, trans-activation was approximately 40% of native E2 protein control levels in assays involving four E2 binding sites. In DNA binding assays with DNA probes having one or two E2 binding sites, mutant polypeptide 360S had practically no DNA binding activity, but in assays with a DNA probe having four E2 binding sites, 360S bound a small fraction— approximately 1% of the DNA probe. This suggested that the 360S mutation might retain slight residual dimerization activity.

We complemented the dimerization defect of mutant polypeptide 360S with a monoclonal antibody, with the two antibody "arms" holding two 360S monomers in close proximity, to simulate dimerization. Monoclonal antibody (Mab) B202, whose epitope is immediately upstream from the DNA binding domain, or Mab B201, whose epitope maps further upstream between amino acids 160 and 220 of E2 protein, were included with the 360S polypeptide and DNA the probe. While monoclonal antibodies are preferred, polyclonal antibodies prepared by conventional techniques may also be employed in super-shift assays. The presence of Mab 202 restored practically complete binding of polypeptide 360S to DNA probes having two or four E2 binding sites. Mab 202 did not restore binding of 360S to the probe having only one E2 binding site (FIG. 4). Mab 201 was only 5–10% as effective in restoring binding of mutant polypeptide 360S to E2 binding sites (data not shown). This was predictable, since the epitope of Mab 201 was further from the E2 DNA binding domain, which contains the E2 dimerization region, than was the Mab 202 epitope. We therefore expected Mab 201 to be less efficient at holding the 360S dimerization regions together than was Mab 202. To exclude the possibility that the monoclonal antibody binding restored DNA binding by altering the conformation of the 360S polypeptide, we performed super-shift assays on 360S with normal dimeric B202 antibodies, which bind two E2 polypeptides (or homologues), and monomeric B202 antibody fragments, which bind only a single E2 polypeptide, and therefore do result in simulated E2 dimers. While the normal dimeric Mab 202 allowed 360S to bind to DNA, the monomeric form of Mab 202 did not restore binding of 360S to DNA in gel shift DNA binding assays. Separate controls confirmed that the monomeric form of Mab 202 did bind to E2 polypeptides. These data strongly support our belief that E2 monomers cannot bind to E2 DNA binding sites.

Since the E2 binding domain has no primary sequence homology to that of any other known transcription factor, the amino acids of E2 responsible for DNA binding interactions ("DNA contact subdomain") were unknown prior to the instant invention.

Four of the mutant polypeptides of this invention, 333V, 337L, 339M and 344L, were isolated from a twelve amino acid span from positions 333 to 344 of E2 protein, which is a highly conserved region of that protein among all papillomaviruses. All were isolated as white colonies in the initial screen (Example 2). All failed to stably bind the E2 DNA element by gel-shift assay. Replacement of glycine 333 with valine also prohibited dimer formation (see Example 5), but since the other mutations (337L, 339M, 344L) existed as pre-formed dimers, we inferred that this region was responsible for DNA interactions. These latter three mutations altered the positively charged amino acids glutamine, lysine and arginine, recognized to be involved in protein nucleic acid interactions. 333V also appeared to be transcriptionally distinct from other dimerization defective mutants (described below) which demonstrated activity with four E2 binding sites, while 333V did not. The high conservation of glycine at this position suggested that it is critical for proper tertiary folding of the C-terminal portion of E2 protein.

Comparison of the amino acid sequence of the region (amino acid residues 333 to 344) of the native E2 polypeptide to the DNA binding domain of other transcription factors failed to reveal similarities to the helix-turn-helix, helix-loop-helix, homeodomain, β-sheet, or zinc finger classes of DNA binding domains. This region of the E2 polypeptide includes several basic amino acids and no acidic residues, yet bears virtually no primary sequence homology to the basic region of the jun/fos family of transcription factors, which has been shown to be required for their DNA binding capability. In common with these, however, this E2 domain also contains a central cystsine (amino acid 340).

The 340R, 340Y and 340F E2 mutations, in which cysteine 340 was replaced with arginine, tyrosine or phenylalanine, respectively, had comparable characteristics to the mutations isolated in this region by chemical mutagenesis and phenotypic selection. These failed to trans-activate the E2 dependent promoter with one, two or four E2 elements, and were likewise defective for DNA binding by gel shift (FIG. 3). These cystsine mutants were able to dimerize (see Example 5). These data suggest that substitution of bulky amino acids at cysteine 340 blocked DNA interactions, not through inhibition of protein-protein interactions, but through destabilization of the DNA contact subdomain.

EXAMPLE 5

In Vitro Dimerization Assay

In order to determine which mutant E2 polypeptides retained the capacity to form dimers, subunits of dimeric E2 proteins were covalently bound by standard cross-linking reactions. Reaction conditions were adjusted so that the covalent bonding between subunits of pre-existing dimers occurred readily, with minimal covalent bonding between monomers. Following the cross-linking reaction, the standard technique of sodium dodecyl sulfate polyacrylamide gel electrophoresis ("SDS-PAGE"), which separates proteins on the basis of size, was employed to determine which E2 mutations yielded polypeptides that formed dimers. Wild type E2 protein dimerizes in the absence of DNA.

For use in the cross-linking reactions, we prepared crude extracts of E2 homologues from cultures of yeast clones (as described in Example 3, supra). We then carried out cross-linking by exposing samples from those yeast crude extracts to an ultraviolet (354 nm) light box, for 30 sec., at a distance of 1 cm.

Following the cross-linking reactions, we prepared the protein samples for SDS polyacrylamide gel electrophoresis by adding SDS to a final concentration of 3% and β-mercaptoethanol to a final concentration of 5%. We then heated the samples and maintained them at 65° C. for about 3 min. We used a 9% polyacrylamide gel to resolve proteins. Following electrophoresis, we transferred the resolved proteins onto nitrocellulose sheets using standard electroblotting techniques. We then detected mutant E2 monomers and cross-linked dimers (at about 50 kD and about 100 kD, respectively) by immunoblot using polyclonal antisera to BPV1 E2 protein.

The results of these assays are set forth in FIG. 2. As shown in that figure, the dimerization-preventing mutations mapped from amino acid position 360 to at least amino acid position 402 of E2 protein, with the dimerization region potentially extending almost to the end of the polypeptide (i.e., position 410). Mutation 360S was the only single amino acid change that removed all dimerization activity. The 360S mutation interestingly altered a highly conserved tryptophan residue shared among the papillomaviruses. Analyses by UV cross-linking of 360S utilizing yeast and bacterial expression vectors demonstrated the inability of this tryptophan point mutant to form dimers. Mutant 360S was a very poor repressor, strongly supporting our belief that the dimerization function is required for repression of papillomavirus trans-activation and viral replication. Dimerization-defective mutants, 3SLI and 402, likely had intact DNA binding domains, since like mutant 360S, 3SLI and (to a lesser extent) 402* could super-shift—they could bind DNA and give a shift in a band retardation assay in the presence of a monoclonal antibody that recognizes the DNA domain binding of E2 protein (see Example 4). We believe that this super-shift activity resulted from the E2 mutant polypeptides being held together as a simulated dimer by the antibody. Mutants such as 402*, which have small insertions or deletions, may have failed to dimerize due to gross perturbations in protein folding. Thus, it is not clear whether the region of that mutation is directly involved in dimerization.

E2 Dimerization Function

We have partially characterized a previously published (Haugen et al., supra) E2 mutant, 3812i (called 402* herein), which is DNA binding-defective and inactive in our yeast trans-activation assay system, with even four E2 binding sites. Mutant 402* has an in-frame insertion of 4 amino acids at position 402. Analysis of the biochemistry of this mutant revealed that it does not dimerize in vitro and does not bind to E2 binding sites on DNA in DNA binding (gel shift) assays. However, 402* can be complemented for DNA binding with a polyclonal anti-E2 serum in a super-shift assay. These results suggest that the E2 protein dimerization region itself spans, or is affected by, the region from amino acids 360 to 402 of E2 protein.

Other mutations in the E2 protein dimerization region were isolated as light blue colonies on our initial screening. Mutants 3SLI and 366Y/376L displayed intermediate levels of transcriptional activation, mutant 399I converted a C-terminal methionine to isoleucine and this had slightly reduced ability to activate the E2 dependent promoters. Mutant 386W replaced a highly conserved arginine with tryptophan and was also found to be partially defective for promoter activation. Biochemical characterization of these reduced activation mutants demonstrated DNA binding activity in gel shift assays (Example 4) and formed dimers in vitro. In the repression studies, mutant proteins 386W and 399I were efficient repressors (see Example 6). These mutant polypeptides dimerize and bind DNA. Mutant protein 3SLI had a reduced level of E2 transcriptional repression. Biochemical studies demonstrated that it has decreased dimerization capability, but not as defective as the 360S mutant protein. Mutations 408* and 411* affected the 3' terminus of E2. While this segment of E2 is not highly conserved among the papillomaviruses, the loss of dimerization activity upon insertion of four amino acids at position 402 revealed the requirement of this region for dimerization. Nonetheless, both 408*, which had alteration of the last 3 amino acids and added an additional 8 residues, and 411*, which had the translational stop codon replaced with a leucine codon, resulting in an extra 22 C-terminal amino acid residues, retained trans-activation function in large part. Consistent with its defective dimerization, mutant polypeptide 402* was not able to repress E2 trans-activation. Mutant polypeptides 408* and 411* both can bind DNA and dimerize as 126 amino acid forms purified from the E. coli expression host. 408* was a weak repressor, but 411* failed to repress. It is not clear why 411* does not repress E2 trans-activation, but we believe that it may have reduced ability to form inactive heterodimers with full-length E2 proteins due to the 22 amino acid peptide fused to its carboxyl terminus.

These genetic and biochemical analyses suggest that the region of E2 protein that interacts with DNA directly is between about amino acids 333 and 344, and that dimerization activity is encoded by a complex domain that spans the segment between about amino acids 360 and 402. Accordingly, we believe that the DNA binding recognition and the dimerization functions of E2 proteins are separable and mediated by two novel motifs. A short basic region, unlikely to be helical, is required for DNA binding but not dimerization. While a conserved central cystsine in this motif is not necessary, this represents a critical position for modifying the DNA binding capacity of E2 protein, since replacement of cysteine with large amino acids adds efficiently abrogated DNA binding. The dimerization motif includes a critical tryptophan at position 360 in BPV-1 E2 polypeptide.

It should be noted that DNA binding capacity was lost by a mutant in every instance in which dimerization capacity was lost. These results indicate that dimerization is a prerequisite for DNA binding. However, some mutant gene products that lost the capacity for DNA binding retained the capacity for dimerization. In those mutant gene products, which represent the novel class of E2 trans-activation repressors of this invention, the dimerization function was separated from the DNA binding function. Mutants 337L, 339M, 340F, 340R, 340Y and 344L are included in this group. These mutants that dimerized without binding to E2 DNA binding sites were further tested for capacity to repress E2-dependent trans-activation in cultured animal cells.

EXAMPLE 6

Repression Of E2-Dependent trans-activation In Cultured Animal Cells

We next assayed the capacity of E2 mutants that dimerized without binding to E2 DNA binding sites to repress E2-dependent trans-activation in cultured mammalian cells. In this assay, an E2 dependent reporter plasmid (characterized by either the gene encoding chloramphenicol acetyltransferase (CAT) or the gene encoding human growth hormone (hGH) driven by a truncated SV40 promoter having three upstream E2 binding sites), the full-length wild type E2 trans-activator protein driven by the actin promoter and the mutant clones in an E2-repressor format starting at nucleotide 3089 of BPV, (i.e., amino acid 160), also driven by the actin promoter, were simultaneously introduced into cultured mouse embryo fibroblast cells by well-established electropotation techniques. The E2 repressor DNA was present at a four-fold excess. The E2 repressor assay was performed at an E2 trans-activator level below the saturation level, since high amounts of E2 repress transcription, perhaps by "squelching". Transfections which resulted in the greatest E2 inductions also gave the best E2 repression (see Table II, infra) and the greatest reproducibility.

The reporter plasmid was constructed so that expression of the reporter gene was highly dependent on E2 trans-activation (i.e., it comprised one, two or four E2 DNA binding sites appropriately placed relative to the promoter and reporter gene coding sequence). The choice of a reporter gene is largely a matter of convenience. In general, any gene whose expression, either directly or indirectly, results in a product that can be measured with reasonable accuracy and reliability can be used as a reporter gene. Preferred reporter genes for the assay of E2 trans-activation in the cultured mammalian cells according to this invention are the gene encoding hGH and the gene encoding CAT.

Figure 5:
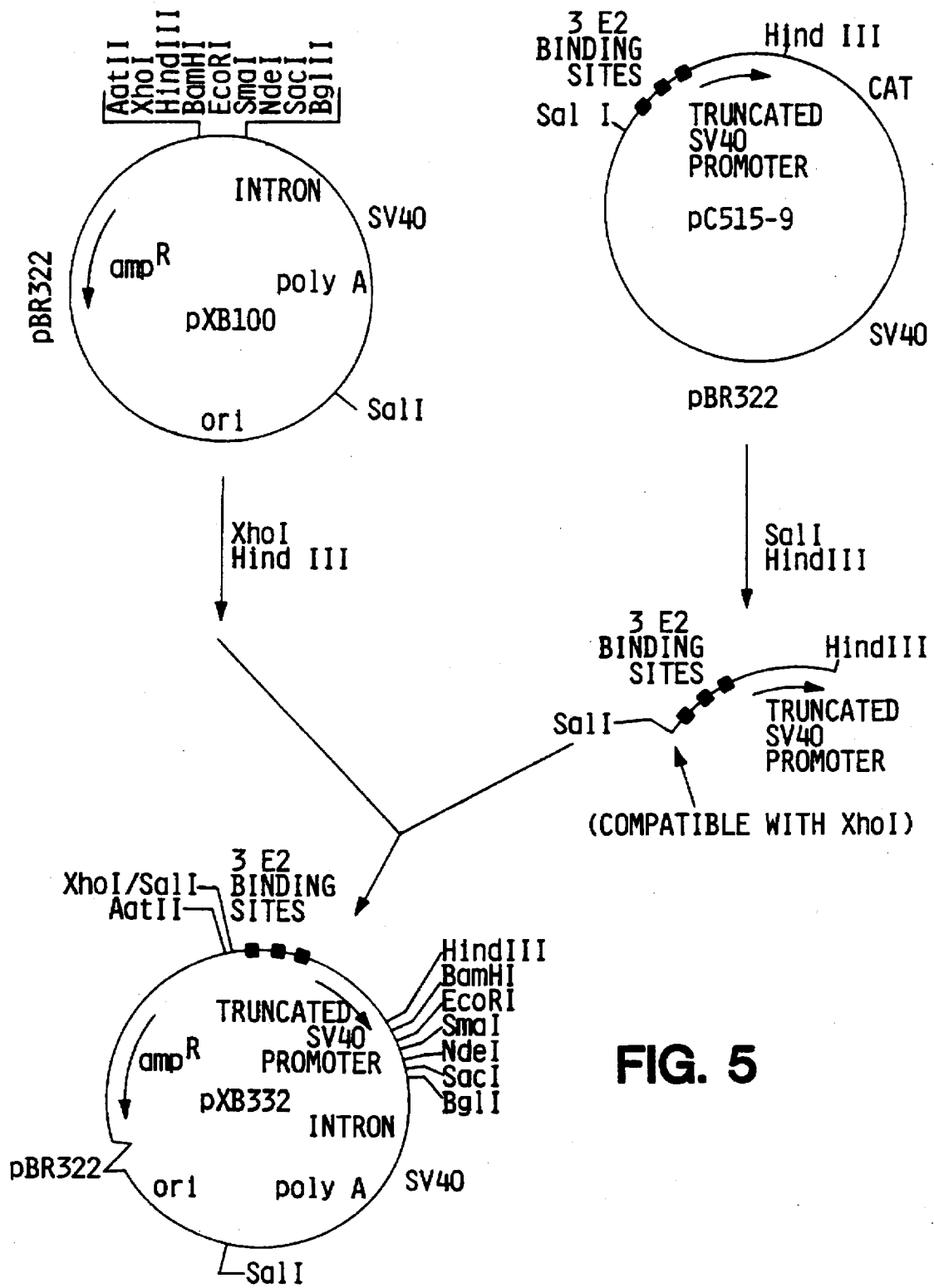
FIG. 5 schematically depicts the construction of plasmid pXB332.
Figure 6:
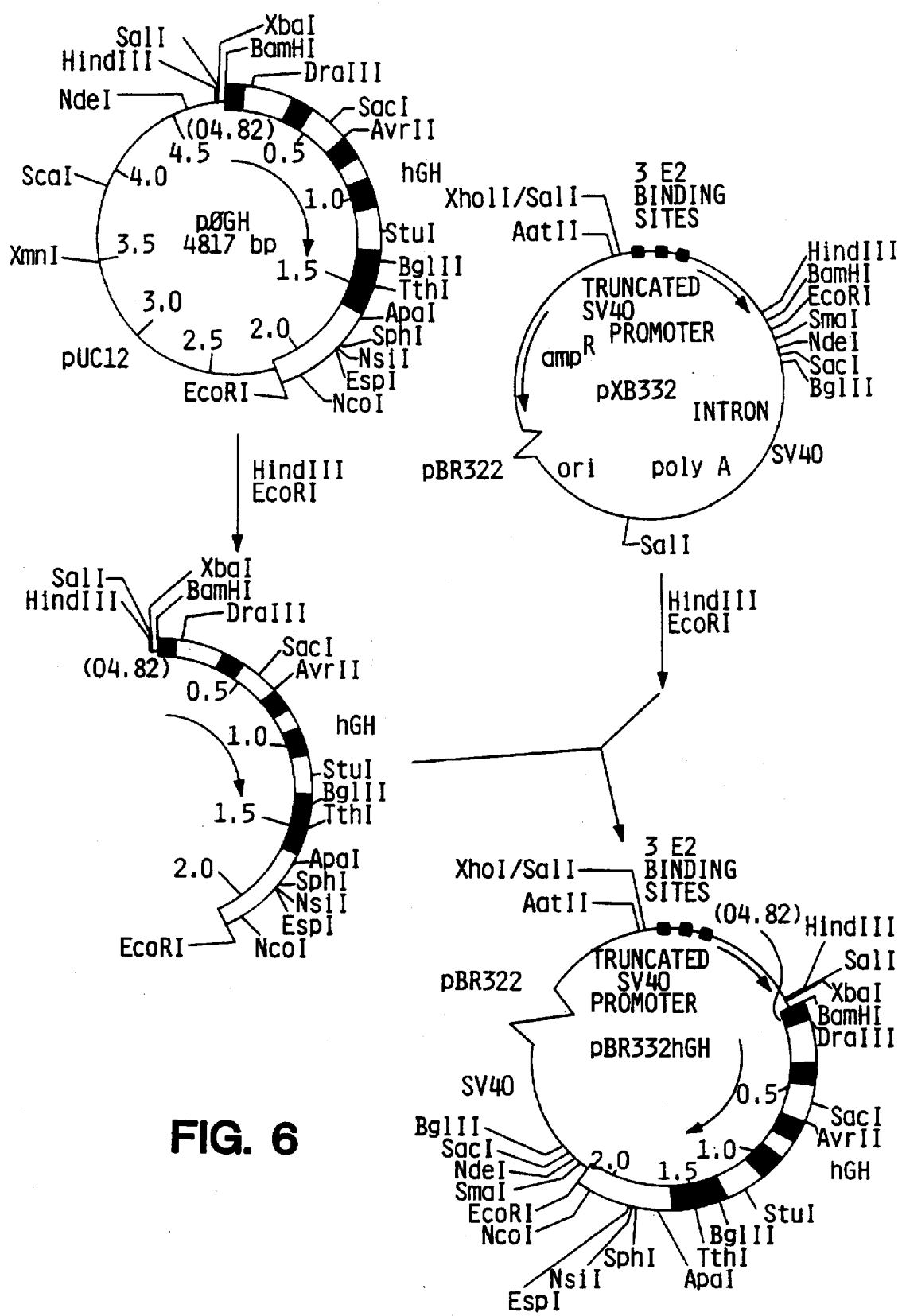
FIG. 6 schematically depicts the construction of plasmid pXB323hGH.

We constructed the hGH reporter plasmid, pXB332hGH, in a two-step process (FIGS. 5 and 6). First, we constructed pXB332 by inserting the E2-dependent promoter (SalI-HindIII fragment) from the E2-dependent reporter plasmid pC515-9 (Hawley-Nelson et al., supra, (1988)) into plasmid vector pXB100 (see FIGS. 5 and 7) that had been previously cleaved with XhoI and HindIII, to form plasmid pXB332. We then inserted the hGH gene as a HindIII-EcoRI fragment from pOGH (Nichols Institute, San Juan Capistrano, Calif.) into pXB332 that had been cleaved with HindIII and EcoRI to create pXB322hGH (FIG. 6). We constructed the CAT reporter plasmid according to a published method (P. Hawley-Nelson, supra).

The E2 trans-activator plasmid vector comprised a full-length native BPV1 E2 gene from pCO-E2 (Hawley-Nelson et al., supra), operatively linked to control sequences that rendered its expression essentially constitutive. Thus, the E2 trans-activator plasmid directed synthesis of E2 protein for trans-activation of the reporter gene. In order to ensure that repressor effects were observable, however, the promoter controlling expression of the full-length E2 gene was not so active as to yield saturating levels of full-length E2 protein in the transfected mammalian cells of the repressor assay system. If the E2 trans-activator gene is overexpressed, repression data are unreliable. In a preferred embodiment of this invention, a chicken β-actin promoter is employed for expression of the E2 trans-activator gene.

We expressed the native E2 coding sequences and mutant E2 coding sequences from the chicken βactin promoter (T. A. Kost et al., "The Nucleotide Sequence of the Chick Cytoplasmic β-Actin Gene", *Nucl. Acids Res.*, 11, pp. 8287–8301 (1983); A. Seiler-Tuyns et al., "Expression and Regulation of Chicken Actin Genes Introduced into Mouse Myogenic and Non-Myogenic Cells", *Proc. Natl. Acad. Sci. USA*, 81, pp. 2980–84 (1984)) in animal cells using vector pXB101 (See FIG. 7).

Figure 7:
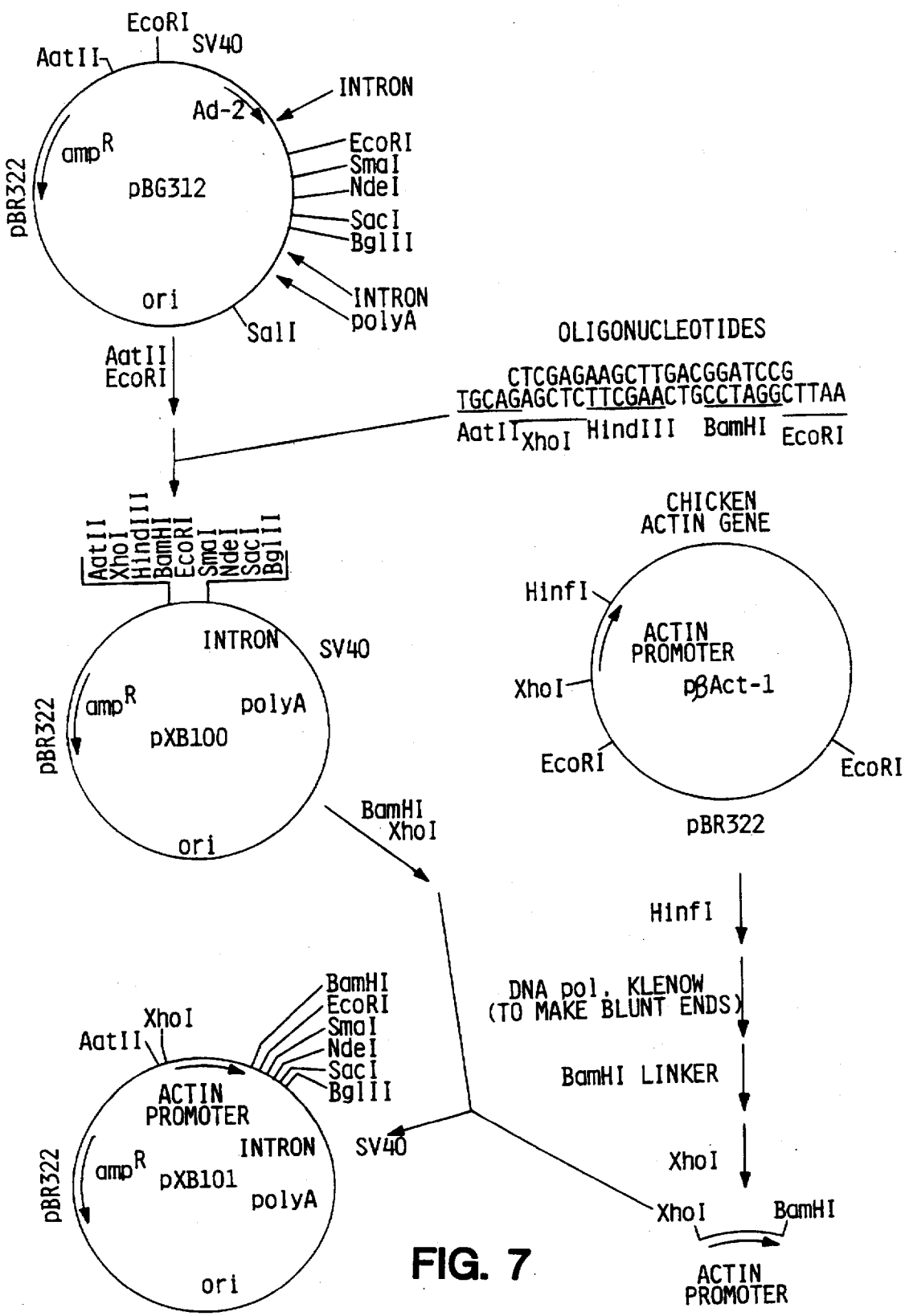
FIG. 7 schematically depicts the construction of plasmid pXB101.

We constructed plasmid pXB101 in a 2-step process (FIG. 7). Two oligonucleotides were synthesized and annealed to form a polylinker:
5' CTCGAGAAGCTTGACGGATCCG 3' (SEQ ID NO: 18)
3' TGCAGAGCTCTTCGAACTGCCTAGGCTTAA 5' (SEQ ID NO: 19)

This polylinker contained XhoI, HindIII, and BamHI restriction sites internally, with an AatII compatible overhang at the 5' end and an EcoRI compatible end at the 3' end. We then cleaved plasmid pBG312 (R. L. Cate et al., "Isolation of the Bovine and Human Genes for Mullerian Inhibiting Substance and Expression of the Human Gene in Animal Cells", *Cell*, 45, pp. 685–98 (1986)) with AatII and EcoRI to release a fragment containing the Ad-2 promoter of pBG312. We inserted the polylinker into the cleaved pBG312 in place of the Ad-2 promoter to form the promoterless vector pXB100. We then cleaved pXB100 with XhoI and BamHI (exploiting the polylinker sites) and inserted the chicken β-actin promoter from pBAct-1 (Kost et al., supra) as a 280 bp XhoI-BamHI fragment, to form pXB101.

Figure 8:
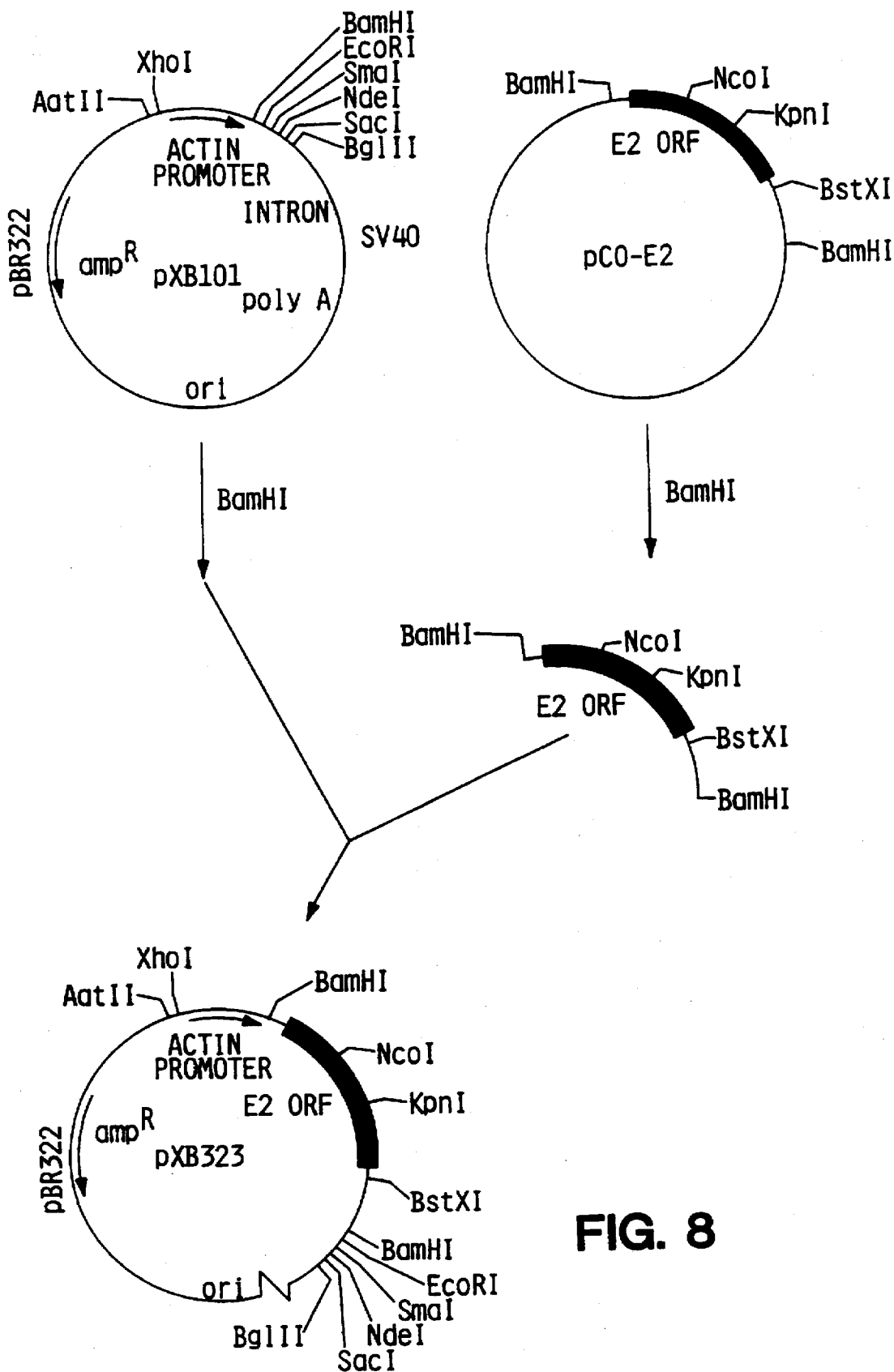
FIG. 8 schematically depicts the construction of plasmid pXB323.

For expression of native full-length E2 protein, we inserted a 1866 bp BamHI fragment from pCO-E2 (Hawley-Nelson et al. supra) into the BamHI site of pXB101, to form plasmid pXB323 (FIG. 8).

Figure 9:
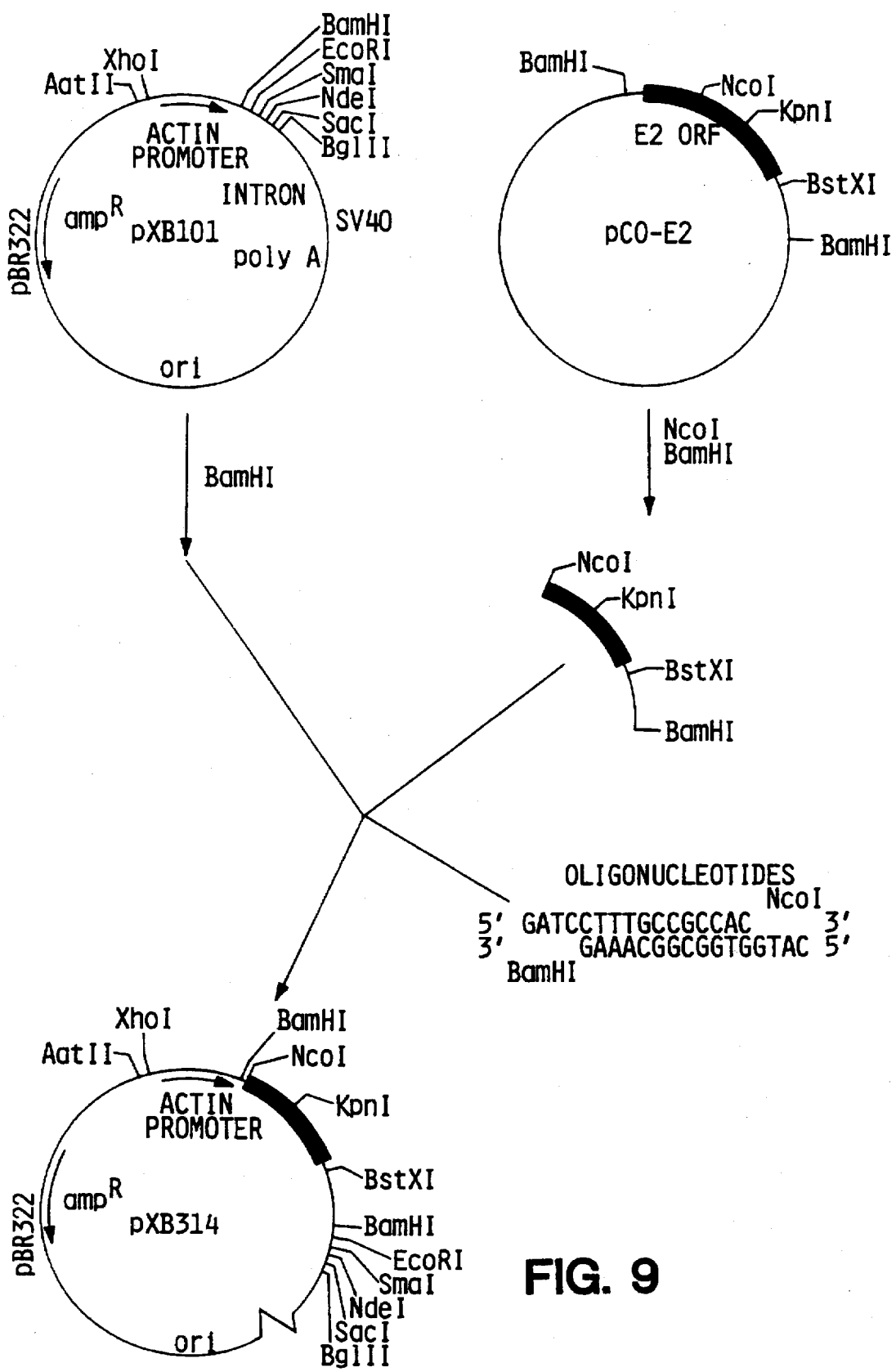
FIG. 9 schematically depicts the construction of plasmid pXB314.

A polypeptide consisting of the C-terminal 249 amino acids of the native E2 protein lacks trans-activation capacity and can repress trans-activation by native full-length E2 protein (P. F. Lambert et al., supra). For expression of the native BPV1 E2 repressor, the 1362 bp NcoI-BamHI fragment of pXB323 (encoding the C-terminal 249 amino acids of the BPV1 E2 protein and starting with a methionine at the NcoI site), was inserted into the BamHI site of pXB101, to form pXB314 (FIG. 9). Synthetic oligonucleotides were also inserted in order to join the NcoI cohesive end of the 1362 bp fragment to the BamHI cohesive end of pXB101. Those synthetic oligonucleotides are shown below:
5' GATCCTTTGCCGCCAC 3' (SEQ ID NO: 20)
3' GAAACGGCGGTGGTAC 5' (SEQ ID NO: 21)

Figure 10:
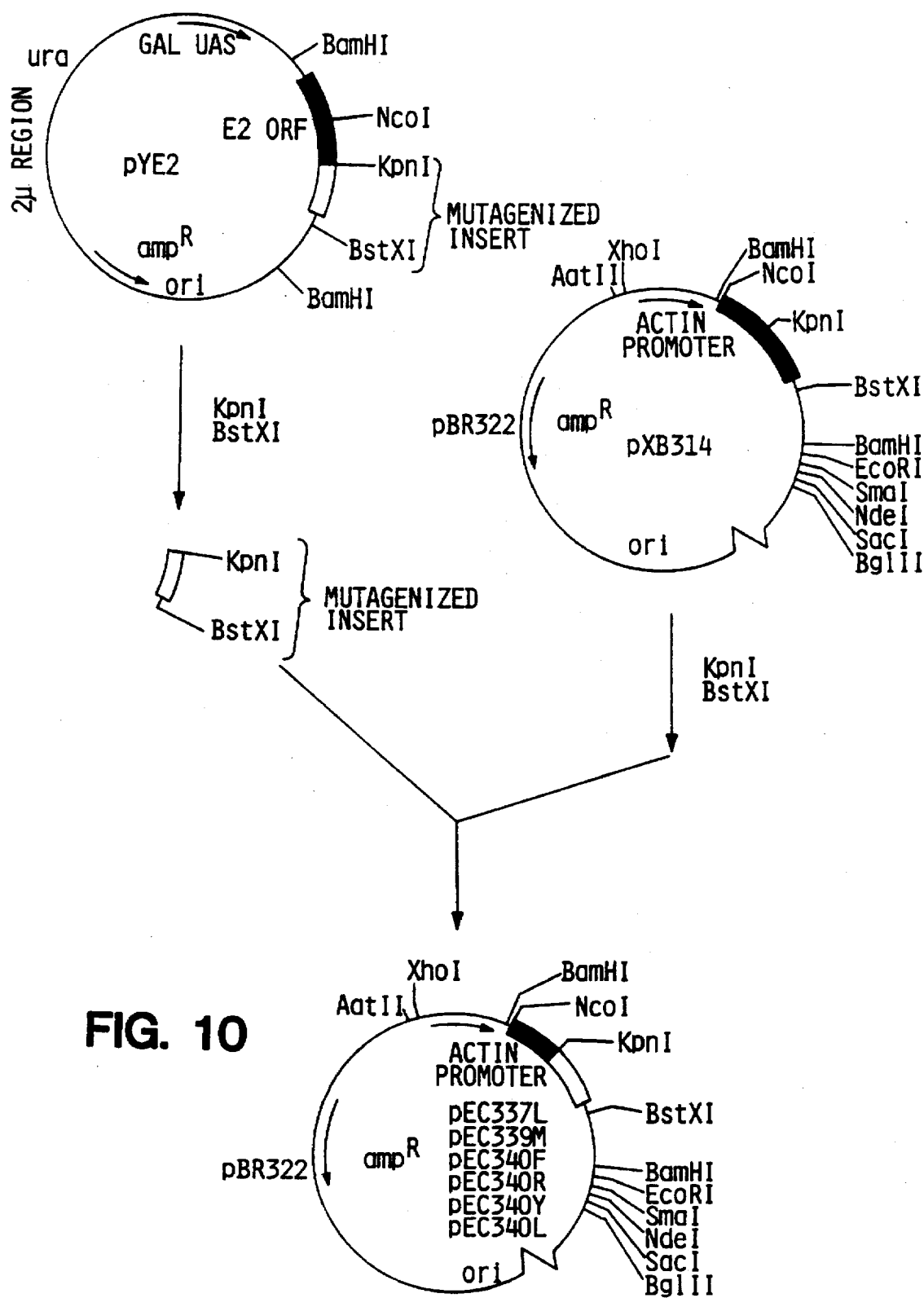
FIG. 10 schematically depicts the construction of plasmids pEC337L, pEC339M, pEC340F, pEC340R, pEC340Y and pEC344L.

In order to test E2 homologues for their capacity to repress E2 trans-activation, mutant forms of the E2 DNA binding domain (from clones selected in the phenotype screening described in Examples 2 and 3 above) were inserted as KpnI-BstXI fragments into KpnI-BstXI-cleaved pXB314 (see FIG. 10). In this way, the C-terminal 126 amino acids of the polypeptide consisting of the C-terminal 249 amino acids of the native E2 polypeptide were replaced with the corresponding mutant sequences to form each of the mutant E2 repressor plasmids assayed, including pEC337L, pE339M, pEC340F, pEC340R, pEC340Y and pEC344L.

All transfections and assays were performed at subsaturating levels of the E2 trans-activator. This was done by using the moderately weak actin promoter to drive expression of the protein. Unless otherwise indicated, all steps were carried out at room temperature.

The transfections were carried out on the mouse embryo fibroblast cell line Balb/c 3T3, clone A31 (S. A. Aaronson and G. J. Todaro, "Development of 3T3-Like Lines from Balb/c Mouse Embryo Cultures: Transformation Susceptibility to SV40", *J. Cell Physiol.*, 72, pp. 141–48 (1968)), obtained from the American Type Culture Collection (ATCC accession no. ATCC CCL163). The 3T3 cell culture medium was DulBecco's minimal essential medium (Gibco, Grand Island, N.Y.), with 10% donor calf serum (Hazelton, Lenexa, Kans.) and 4 mM glutamine (Whittaker, Walkersville, Md.). We maintained the 3T3 cell cultures in an incubator at 37° C., in an atmosphere containing 5.5% $CO_2$. Cells were grown in 100 mm culture dishes (Corning, Corning, N.Y., cat. no. 25020). The cells were passaged by washing with phosphate-buffered saline solution (Gibco) and treatment with trypsin (Gibco), (to remove adhering cells from the culture vessels), followed by addition of fresh culture medium and dilution of cultures into vessels containing fresh culture medium.

Transient electropotations were carried out to measure the repression activity of the mutants. We employed a commercially available electropotation device (Gens Pulser™, BioRad, Richmond, Calif.) and used an electroporation technique similar to that of G. Chu et al., "Electropotation For the Efficient Transfection of Mammalian Cells With DNA", *Nucl. Acids Res.*, 15, pp. 1311–26 (1987) to introduce plasmids into the 3T3 cells. In each electroporation, we used a total of 400 µg of DNA. Of that 400 µg, 20 µg was reporter plasmid, 20 µg was trans-activator plasmid and 80 µg was repressor plasmid. The remainder of the 400 µg was made up with herring sperm DNA (Boehringer Mannheim, Indianapolis, Ind.), that had been sonicated to fragments of about 300 to 2000 bp in size. To a solution of the DNA (0.4 ml) we added NaCl to a final concentration of 0.1 M and then we precipitated the DNA with 2.5 volumes of ethanol. We pelleted the precipitated DNA in an Eppendorf centrifuge, air-dried it in a tissue culture hood and resuspended the DNA in 0.8 ml of 20 mM Hepes (pH 7.05), 137 mM NaCl, 5 mM KCl, 0.7 mM $Na_2HPO_4$ and 6 mM dextrose, ("1×HeBS"). We allowed the DNA to resuspend in the 1×HeBS from about 3 to 24 hours.

For each electropotation, we removed about $5 \times 10^6$ 3T3 cells (that had been passaged or fed on the previous day) from a culture vessel by trypsin treatment and pelleted the cells by centrifugation at 1000 rpm in a Damon/IECHN-SII rotor (about 250×g) for 4 min. After removal of the medium above the pelleted cells by aspiration, we resuspended the cells in the DNA plus 1×HeBs (see above). We then transferred the solution containing the DNA and cells to an electroporation cuvette. We immediately discharged a 960 µFD capacitor, to yield about 240 v for about 10 msec. We left the cells in the cuvette for about 8 min. and then transferred them to a test tube containing 10 ml of culture medium and pelleted as above. We then aspirated the medium, resuspended the cells in 10 ml culture medium, seeded them into a 10 cm plate and returned the plate to the cell culture incubator.

When using the hGH reporter gene, we harvested the culture medium to assay for secreted hGH after 48 to 72 hrs. Alternatively, when using the CAT reporter, we harvested the electroporated cells after 48 to 72 hours. We controlled for cell number by counting cells, if using the hGH assay, and by measuring total protein concentration in the extracts, if using the CAT assay.

In order to quantitate expression of the reporter gene, we performed hGH assays according to the method of Selden, *Potocols in Molecular Biology*, Greene Publishing Associates, N.Y., pp. 9.7.1–9.7.2 (1987). For hGH assays, we used a commercially available kit (Allegro™ Human Growth Hormone transient gene expression system kit, Nichols Institute, San Juan Capistrano, Calif.). We performed CAT assays according to the method of C. M. Gorman et al. "Recombinant Genomes Which Express Chloramphenicol Acetyltransferase in Mammalian Cells", *Mol. Cell Biol.*, 2, pp. 1044–51 (1982)). Positive and negative controls were employed, as appropriate. Such controls included transfection of a reporter plasmid in the absence of a trans-activator plasmid (reporter background), transfection of a reporter plasmid in the presence of a trans-activator plasmid and absence of trans-activation repressor plasmid (unrepressed trans-activation) and transfection of a reporter plasmid in the presence of a trans-activator plasmid and a plasmid for expression of the BPV1 E2 native repressor (i.e., the C-terminal 249 amino acids of the native E2 polypeptide).

In evaluating the E2 homologues, we utilized data on reporter gens background level, E2 induction level and repression produced by the BPV1 E2 native repressor. Reporter gens background activity was calculated as reporter activity in the absence of E2 trans-activator protein. E2 induction level was calculated as reporter activity in the presence of E2 trans-activator protein divided by reporter background activity. Repression was calculated according to the following formula:

$$\frac{[(ACT \text{ with } E2) - BKG] - [(ACT \text{ with } E2 \text{ and } REP) - BKG]}{(ACT \text{ with } E2) - BKG}$$

TABLE I

| Transfection | hGH (µg/ml) | Induction | Repression |
|---|---|---|---|
| pXB332hGH (reporter) | 0.1 | — | — |
| pXB322hGH + pXB323 (reporter & trans-activator) | 10.0 | 100-fold | — |
| pXB332hGH + pXB323 + pXB314 (reporter & trans-activator & native repressor) | 1.0 | 10-fold | 90.9% |
| pXB332hGH + pXB323 + pXB314.360S (reporter & trans-activator & homologous repressor) | 7.0 | 70-fold | 30.3% |

*In this example, repression by the homologous repressor (360S) could also be expressed as 33% of the repression exhibited by the native repressor.

Table I illustrates a convenient and valid means of comparing repressor activities, with appropriate controls taken into account.

Table II shows raw data and calculated values for several E2 repressor assays carried out as described above. In Table II, CPM represents sample radioactivity counts per minute; CPM—BKGD represents sample counts per minute minus background counts per minute; % Repression represents the value calculated for the mutant, from the formula above, multiplied by 100; % of Native Repression represents the % Repression value for the mutant divided by the repression value for the native repressor, calculated from the formula above; C represents the hGH or CAT reporter plasmid; 323 represents the trans-activator plasmid, pXB323; 314 represents the native repressor plasmid, pXB314; and the numbers followed by an upper case letter or an asterisk refer to the mutant polypeptide sequence being tested (see FIG. 2).

TABLE II

E2 REPRESSION ASSAYS

| SAMPLE | CPM | CPM - BKGD | % REPRESSION | % OF NATIVE REPRESSION |
|---|---|---|---|---|
| CAT ASSAY #3 | | | | |
| C | 234 | — | — | — |
| C + 323 | 3,278 | 3,044 | — | — |
| C + 314 + 323 | 378 | 144 | 95.3 | — |
| C + 340S + 323 | 572.5 | 338.5 | 88.9 | 93.3 |
| CAT ASSAY #4 | | | | |
| C | 161.5 | — | — | — |
| C + 323 | 9,751 | 9,589.5 | — | — |
| C + 314 + 323 | 509.5 | 348 | 96.4 | — |
| C + 337L + 323 | 969.5 | 808 | 91.6 | 95.0 |
| C + 340R + 323 | 538 | 376.5 | 96.1 | 99.7 |
| C + 360S + 323 | 9,096 | 8,934.5 | 6.8 | 7.1 |
| C + 402* + 323 | 51868.5 | 5,707 | 40.5 | 42.0 |
| CAT ASSAY #5 | | | | |
| C | 292 | — | — | — |
| C + 323 | 5,914 | 5,622 | — | — |
| C + 314 + 323 | 398 | 106 | 98.1 | — |
| C + 339M + 323 | 1,738 | 1,446 | 74.3 | 75.7 |
| C + 344L + 323 | 579 | 287 | 94.9 | 96.7 |
| C + 360S + 323 | 2,656 | 2,364 | 57.9 | 59.1 |
| C + 402* + 323 | 3,102 | 2,810 | 50.0 | 51.0 |
| CAT ASSAY #6 | | | | |
| C | 122.5 | — | — | — |
| C + 323 | 2,867 | 2,744.5 | — | — |
| C + 314 + 323 | 218 | 95.5 | 96.5 | — |
| C + 337L + 323 | 418.5 | 296 | 89.2 | 92.4 |
| C + 339M + 323 | 725.5 | 603 | 78.0 | 80.9 |
| C + 370I + 323 | 313.5 | 191 | 93.0 | 96.4 |
| C + 3SLI + 323 | 1,800 | 1,677.5 | 38.9 | 40.3 |
| C + 399I + 323 | 456 | 333.5 | 87.8 | 91.0 |
| C + 366Y/376L + 323 | 2,705.5 | 2,583 | 5.9 | 6.1 |
| CAT ASSAY #EP6 | | | | |
| C | 377 | — | — | — |
| C + 323 | 3,906 | 3,529 | — | — |
| C + 314 + 323 | 1,053 | 676 | 80.8 | — |
| C + 316Y + 323 | 3,607 | 3,230 | 8.5 | 10.5 |
| C + 340Y + 323 | 756 | 379 | 89.3 | 110.5 |
| C + 344L + 323 | 1,429 | 1,052 | 70.2 | 86.9 |
| C + 370I + 323 | 3,214 | 2,837 | 19.6 | 24.3 |
| C + 3SLI + 323 | 2,524 | 2,147 | 39.2 | 48.5 |
| hGH ASSAY #2 | | | | |
| C | 160 | — | — | — |
| C + 323 | 9,937 | 9,777 | — | — |
| C + 314 + 323 | 415 | 255 | 97.4 | — |
| C + 337L + 323 | 862 | 702 | 92.8 | 95.3 |
| C + 340R + 323 | 452 | 292 | 97.0 | 99.6 |
| C + 344L + 323 | 1,680 | 1,520 | 84.4 | 86.7 |
| C + 360S + 323 | 7,925 | 7,765 | 20.6 | 21.1 |
| C + 370I + 323 | 8,175 | 8,015 | 18.0 | 18.5 |
| hGH ASSAY #3 | | | | |
| C | 303 | — | — | — |
| C + 323 | 14,522 | 14,218 | — | — |
| C + 314 + 323 | 2,237 | 1,934 | 86.4 | — |
| C + 317STOP + 323 | 12,830 | 12,527 | 11.9 | 13.8 |
| C + 333V + 323 | 19,853 | 19,550 | 0 | 0 |
| C + 339M + 323 | 16,891 | 16,588 | 0 | 0 |
| C + 340F + 323 | 2,629 | 2,326 | 83.6 | 96.8 |
| hGH ASSAY #5 | | | | |
| C | 239 | — | — | — |
| C + 323 | 2,455 | 2,216 | — | — |
| C + 314 + 323 | 473 | 234 | 89.4 | — |
| C + 316Y + 323 | 2,287 | 2,048 | 7.6 | 8.5 |
| C + 333V + 323 | 4,275 | 4,036 | 0 | 0 |
| C + 340G + 323 | 486 | 247 | 88.8 | 99.3 |
| C + 408* + 323 | 1,219 | 980 | 55.8 | 62.4 |
| C + 411* + 323 | 4,756 | 4,517 | 0 | 0 |

TABLE II-continued

E2 REPRESSION ASSAYS

| SAMPLE | CPM | CPM - BKGD | % REPRESSION | % OF NATIVE REPRESSION |
|---|---|---|---|---|
| hGH ASSAY #6 | | | | |
| C | 169 | — | — | — |
| C + 323 | 5,207 | 5,038 | — | — |
| C + 314 + 323 | 282 | 113 | 97.8 | — |
| C + 340Y + 323 | 289 | 120 | 97.6 | 99.8 |
| C + 386W + 323 | 1,147 | 978 | 80.6 | 82.4 |
| C + 408* + 323 | 2,024 | 1,855 | 63.2 | 64.6 |
| hGH ASSAY #7 | | | | |
| C | 110 | — | — | — |
| C + 323 | 1,692 | 1,582 | — | — |
| C + 370I + 323 | 335 | 225 | 85.8 | ? |
| hGH ASSAY #EP5 | | | | |
| C | 210 | — | — | — |
| C + 323 | 11,207 | 10,987 | — | — |
| C + 314 + 323 | 782 | 572 | 94.8 | — |
| C + 317STOP + 323 | 10,943 | 10,733 | 2.4 | 2.5 |
| C + 339M + 323 | 2,376 | 2,166 | 80.3 | 84.7 |
| C + 340F + 323 | 1,475 | 1,265 | 88.5 | 93.4 |
| C + 340G + 323 | 807 | 597 | 94.6 | 99.7 |
| C + 340R + 323 | 763 | 553 | 95.0 | 100.2 |
| C + 340S + 323 | 1,290 | 1,080 | 90.2 | 95.1 |
| C + 366Y/376L + 323 | 8,314 | 8,104 | 26.3 | 27.7 |
| C + 386W + 323 | 2,151 | 1,94 | 182.3 | 86.9 |
| C + 399I + 323 | 1,750 | 1,540 | 86.0 | 90.7 |
| C + 411L + 323 | 10,206 | 9,996 | 9.1 | 9.6 |

Ratio of Repressor to trans-activator = 4:1
Dashes indicate not applicable.
Question mark indicates that % of Native Repression could not be calculated, because no control with the native repressor plasmid (C + 314 + 323) was done in that assay.

Repression by a four-fold excess (by weight) of the native repressor was never below 80% in any assay. Reproducibility of the assay results shown in Table II was generally high. Mutant polypeptide 339M did not repress at all in one assay but gave good repression in three other assays, when a different DNA preparation was used.

We tested each E2 homologue between two and four times for its ability to repress E2-dependent trans-activation in mammalian cells. A compilation of trans-activation repression assay results is shown in Table III below. The repression activity is also summarized in FIG. 2. It is clear from these assays that the C-terminal portion of E2 protein need not be able to bind DNA in order to repress.

TABLE III

Summary of Mutant E2 Repressor Activity[1]

| Mutant | Repression as % Decrease in Trans-Activation By E2 | Repression As % of Repression By WT Repressor[2] | +/− |
|---|---|---|---|
| 316Y | 8.0 | 9.5 | − |
| 317STOP | 7.1 | 8.1 | − |
| 333V | 0[3] | — | − |
| 337L | 90.4 | 93.7 | + |
| 339M | 76.2 | 78.3 | + |
| 340F | 86.1 | 95.1 | + |
| 340G | 91.7 | 99.5 | + |
| 340R | 95.6 | 99.9 | + |
| 340S | 89.6 | 94.2 | + |
| 340Y | 93.5 | 105.1 | + |
| 344L | 82.6 | 91.8 | + |
| 360S | 32.3 | 33.1 | − |
| 366Y/376L | 16.1 | 16.9 | − |

TABLE III-continued

Summary of Mutant E2 Repressor Activity[1]

| Mutant | Repression as % Decrease in Trans-Activation By E2 | Repression As % of Repression By WT Repressor[2] | +/− |
|---|---|---|---|
| 370I | 66.1 | 70.9 | (±) |
| 374S/375L/391I (3SLI) | 39.0 | 44.4 | − |
| 386W | 81.4 | 84.6 | + |
| 399I | 86.9 | 90.8 | + |
| 402* (4 AA insert) | 45.2 | 46.6 | − |
| 408* (11 AA insert) | 59.5 | 63.5 | (±) |
| 411* | 4.5 | 4.8 | − |

[1]All values represent the average of two to four assays.
[2]Each mutant repressor was compared to the native repressor in the same assay.
[3]"0" indicates that activation was slightly greater in the presence of this mutant than in the control having no repressor present.

Table III shows a compilation of the results of all mutants which have been tested for repression. We arbitrarily defined a repressor as a protein which repressed by at least 70% at a four-fold excess. Mutants 337L, 340F, 340R, 340Y and 344L, all of which could dimerize but did not bind DNA, repressed essentially as well as the native repressor. Dimerization-defective mutants 360S, 3SLI and 402* did not repress. Mutants 316Y, 411*, and 366Y/376L did not repress, despite the fact that they were capable of forming dimers in vitro. However, mutant polypeptide 316Y appeared to be very unstable, suggesting that mutant polypeptides 316Y, 411* and 366Y/376L may have failed to repress as a result of their presence in the cells at very low concentrations, due to instability.

Thus, it appears that DNA binding is not necessary for repression of E2 trans-activation. Instead, a mechanism other than competition for DNA binding sites operates. Mutants which cannot dimerize—or which do so very weakly—317STOP, 333V, 360S, 3SLI and 402* (4 AA insert) either repress poorly or not at all. We believe that the repressors of this invention act through dimer formation. More specifically, we believe that the repressors of this invention form heterodimers with the full-length E2 protein and thereby sequester it in an inactive form.

EXAMPLE 7

Repression of HPV E2-Dependent trans-Activation in Cultured Animal Cells

There is a high level of homology between the E2 binding domains of BPV1 and human papillomaviruses ("HPV"). Accordingly, we tested the ability of homologous HPV E2 sequences to function as E2 trans-activation repressors in a manner similar to that observed with the BPV E2 repressors described in Example 6, supra. To do this, we constructed vectors to express full-length native (trans-activating) HPV E2 protein and putative HPV E2 repressors.

Figure 11:
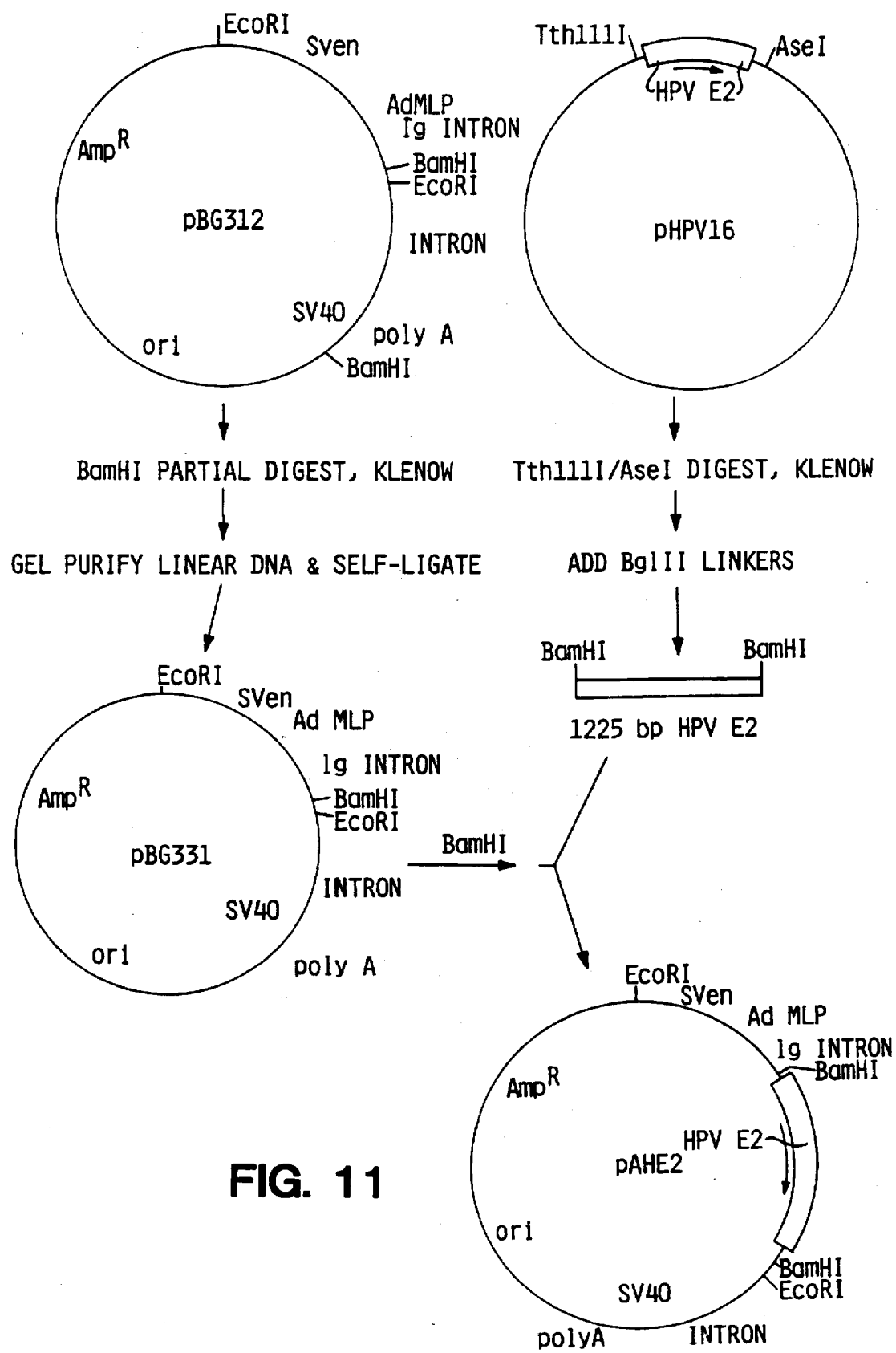
FIG. 11 schematically depicts the construction of plasmids pBG331 and pAHE2.

For expression of a full-length HPV E2 gene, we constructed plasmid pAHE2 (FIG. 11). Plasmid pAHE2 contains the E2 gene from HPV strain 16 operatively linked to the adenovirus major late promoter augmented by the SV40 enhancer upstream of the promoter. We isolated the HPV E2 gene from plasmid pHPV16 (the full-length HPV16 genome cloned into pBR322), described in M. Durst et al., "A Papillomavirus DNA From Cervical Carcinoma And Its Prevalence In Cancer Biopsy Samples From Different Geographic Regions", *Proc. Natl. Acad. Sci. USA*, 80, pp. 3812–15 (1983) as a Tth111I-AseI fragment (Tth111I cleaves at nucleotide 2711, and AseI cleaves at nucleotide 3929 in the HPV16 genome). We blunted the ends of the Tth111I-AseI fragment in a DNA polymerase I Klenow reaction and ligated BamHI linkers (New England Biolabs, cat. no. 1021). We inserted this linker-bearing fragment into BamHI-cleaved plasmid pBG331, to create plasmid pAHE2.

Plasmid pBG331 is the same as pBG312 (Example 6; FIG. 7) except that it lacks the BamHI site downstream of the SV40 polyadenylation signal, making the BamHI site between the promoter and the SV40 intron unique. We removed the unwanted BamHI site by partial BamHI digestion of pBG312, gel purification of the linearized plasmid, blunt end formation by DNA polymerase I Klenow treatment, self-ligation and screening for plasmids with the desired deletion of the BamHI site (FIG. 11).

To provide a positive control (i.e., an E2 repressor) for comparisons in the HPV E2 repression assays, we cloned the DNA sequence ("E2R fragment") encoding the 249-amino acid BPV E2 repressor into plasmid pBG331, to create pBG331E2R. To construct pBG331E2R, we removed the E2R fragment from pXB323 (Example 6; FIG. 8) by BamHI digestion, and then inserted that fragment into BamHI-cleaved pBG331. We used the same procedure to construct plasmid pBG331E2RN, a negative control, to express the dimerization-deficient BPV E2 sequence designated 360N. Since it expresses a dimerization-deficient E2 polypeptide which does not repress E2 trans-activation, we incorporated pBG331E2RN into our repression assays to serve as a negative control. Plasmid pBG331 E2RN expresses a BPV1 E2 repressor with a tryptophan to asparagine mutation at amino acid residue 360. This analogue is dimerization defective. It is similar to analogue 360S, described in Example 5, supra, but exhibits lower dimerization activity.

Figure 12:
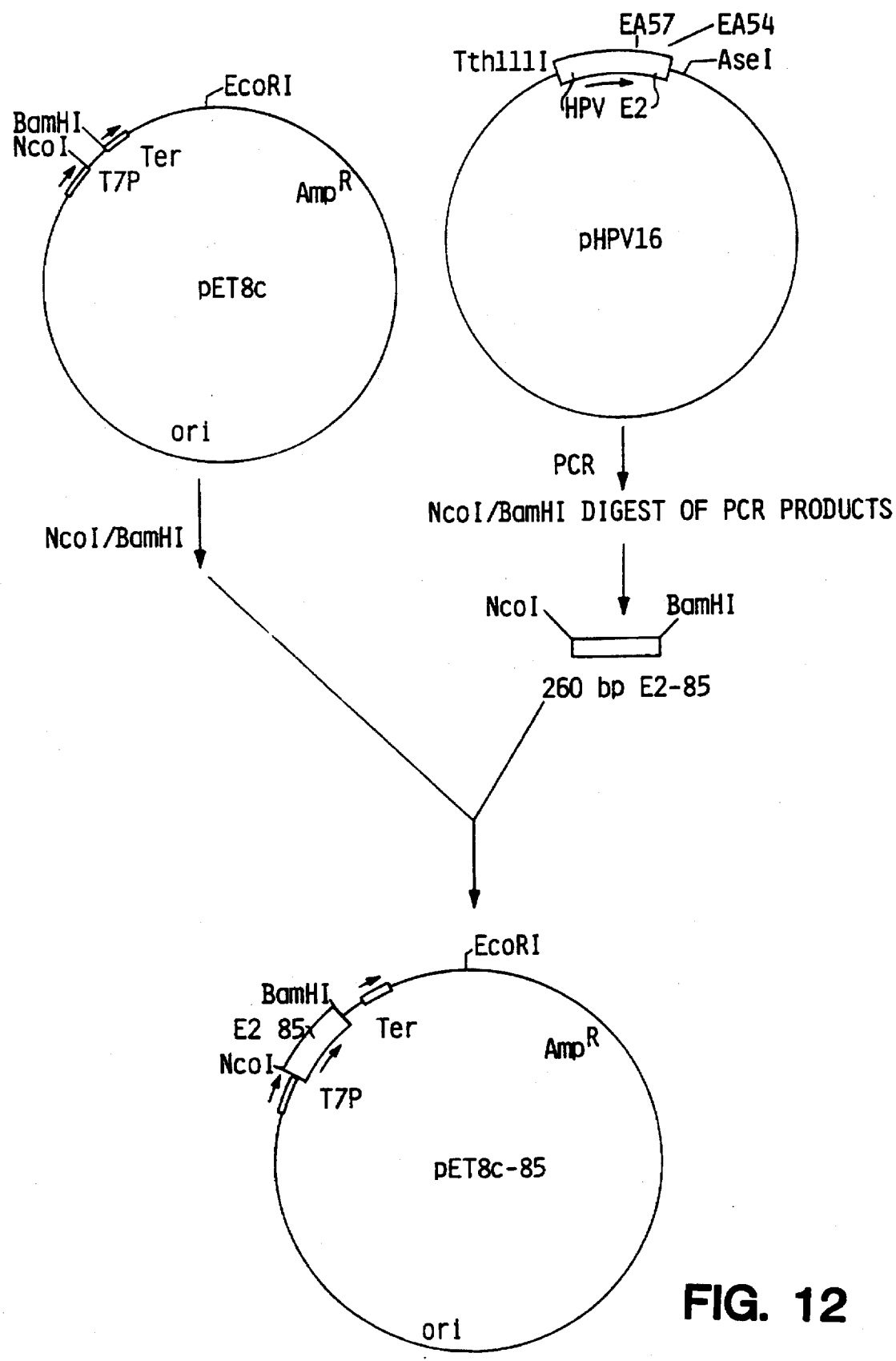
FIG. 12 schematically depicts the construction of plasmid pETSc-85.

Based on our comparison of the BPV1 and HPV16 sequences, we expected the C-terminal 83 amino acid residues of the HPV E2 protein to exhibit dimerization and DNA binding activity, and thus to repress E2 trans-activation. We therefore constructed plasmid pHE2-85 from expression plasmid pBG331 (FIGS. 12 and 13) by inserting a 260 base pair NcoI-BamHI fragment ("E2-85") containing methionine and alanins codons immediately followed by codons for the C-terminal 83 amino acids of HPV16 E2. Similarly, we constructed plasmid pHE2-123 (FIGS. 14 and 15) by inserting into pBG331 a 374 base pair fragment ("E2-123") containing methionine and valine codons immediately followed by codons for the C-terminal 121 amino acids of HPV16 E2.

Figure 13:
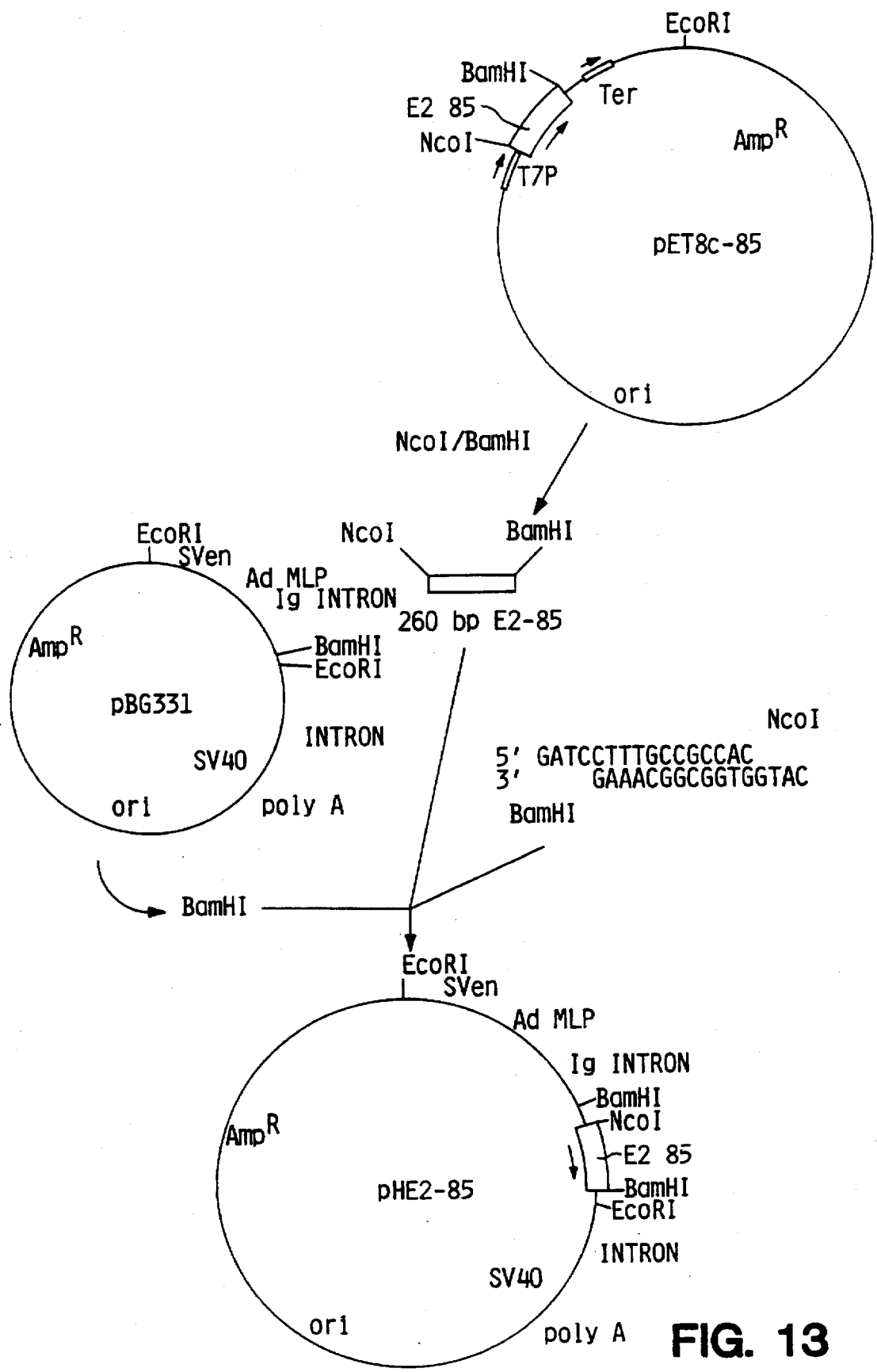
FIG. 13 schematically depicts the construction of plasmid p HE2-85 using a BamHI-NcoI linker (SEQ ID NO'S: 32 and 33).
Figure 14:
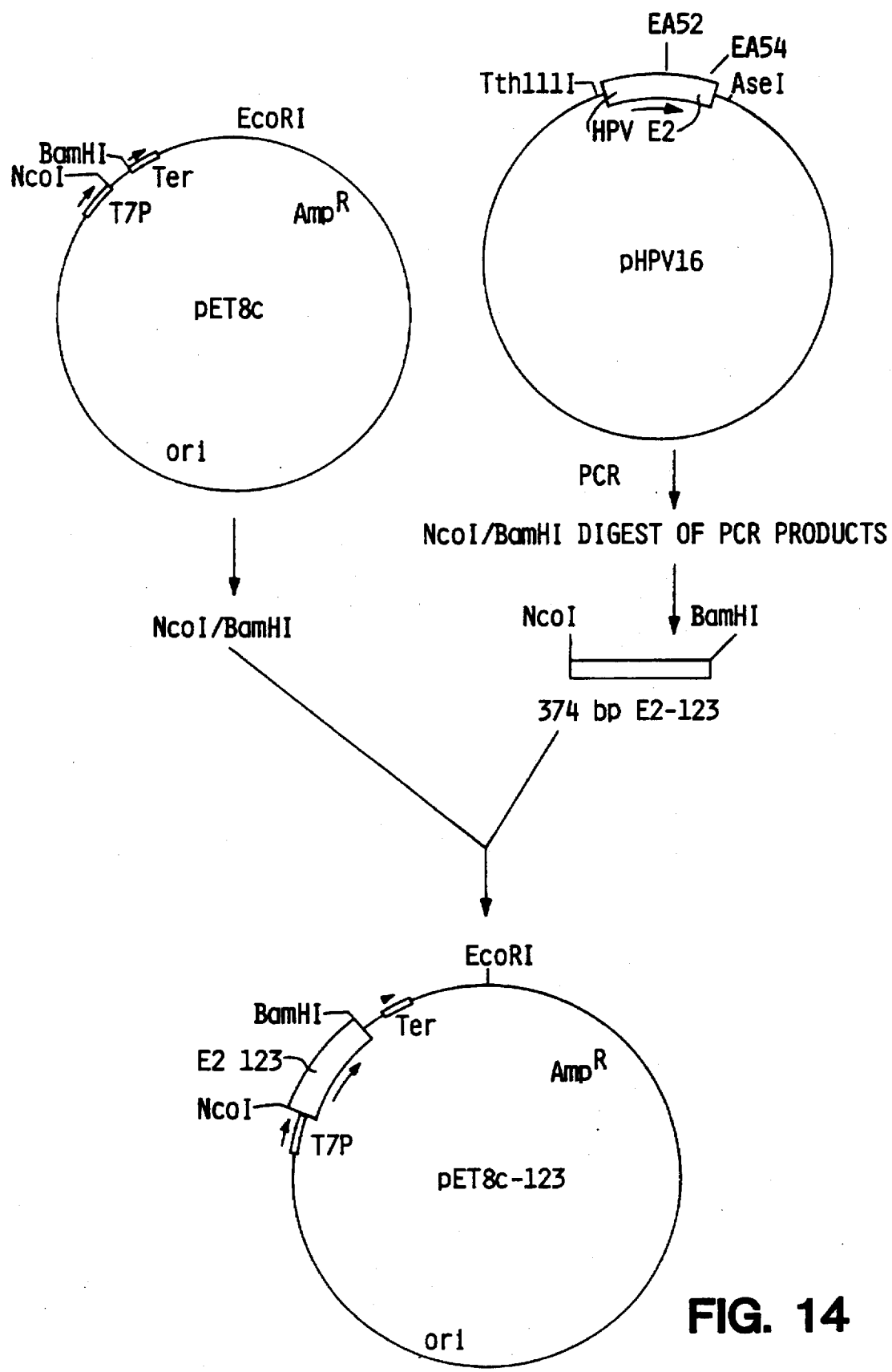
FIG. 14 schematically depicts the construction of plasmid pETSc-123.
Figure 15:
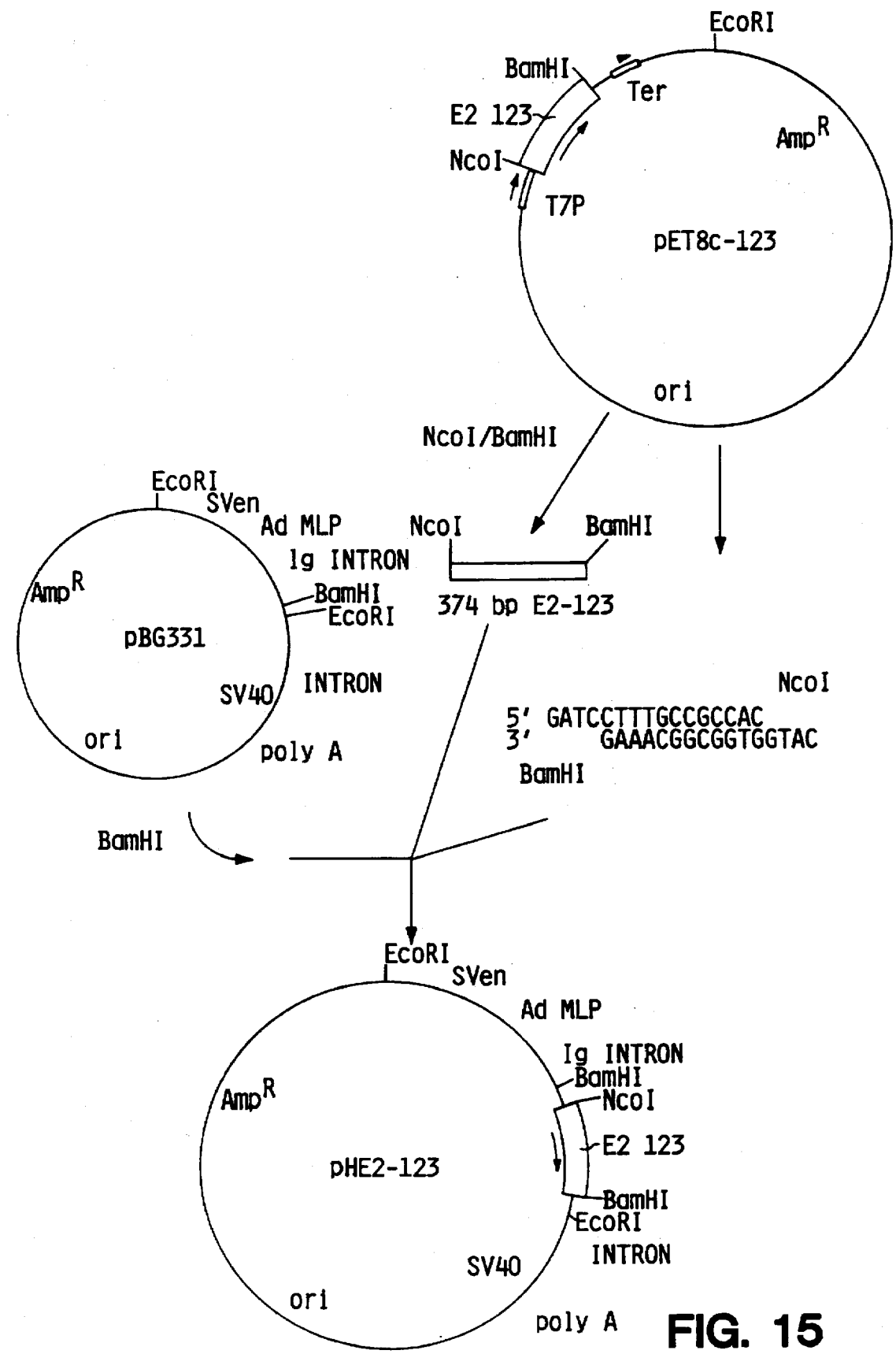
FIG. 15 schematically depicts the construction of plasmid pHE2-123 using a BamHI-NcoI linker (SEQ ID NO'S: 32 and 33).

For construction of plasmids pHE2-85 and pHE2-123, we produced the necessary DNA fragments by standard polymerass chain reaction ("PCR") techniques with pHPV16 as the template. PCR chemicals and equipment are commercially available. For a general discussion of PCR techniques, see Chapter 14 of Sambrook et al., *Molecular Cloning—A Laboratory Manual*, 2nd Ed., Cold Spring Harbor Press (1989). The nucleotide sequence of EA57, the PCR oligonucleotide primer for the 5' end of the 260 base pair E2-85 fragment, is set forth in the Sequence Listing under SEQ ID NO:28. The nucleotide sequence of EA52, the PCR oligonucleotide primer for the 5' end of the 374 base pair E2-123 fragment, is set forth in the Sequence Listing under SEQ ID NO: 29. The nucleotide sequence of EA54, the PCR oligonucleotide primer used for the 3' end of both fragments, is set forth in the Sequence Listing under SEQ ID NO: 30. We digested the PCR products with NcoI and BamHI and cloned the resulting fragments into NcoI/BamHI-digested expression plasmid pET8c (Studier et al, supra), to create plasmids pETSc-85 and pETSc-123. As depicted in FIGS. 13 and 15, we cleaved pETSc-85 and pETSc-123 with NcoI and BamHI and transferred the fragments E2-85 and E2-123 into the unique BamHI site of plasmid pBG331, with the use of the BamHI-NcoI linker described in Example 6 (SEQ ID NO: 20 and SEQ ID NO: 21), to create plasmids pHE2-85 and pHE2-123.

We performed repression assays by transient transfections of mouse fibroblast 3T3 cells, using reporter plasmid pXB332hGH, as described in Example 6, supra. The HPV E2 repression assay results are shown in Table IV, below. In Table IV, C represents the reporter plasmid, pXB332hGH. The other plasmids co-transfected in the repression assays have the same designation in Table IV as in the foregoing discussion. CPM represents sample radioactivity counts per minute; CPM—BKGD represents sample counts per minute minus background (reporter plasmid alone) counts per minute; INDUCTION represents counts per minute for the combination of reporter plasmid with the trans-activator plasmid (pAHE2), divided by counts per minute for the reporter plasmid alone; % REPRESSION represents the value calculated from the formula in Example 6, multiplied by 100.

TABLE IV

HPV E2 REPRESSION ASSAYS

| SAMPLE | CPM | CPM-BKGD | INDUCTION | % REPRESSION |
|---|---|---|---|---|
| hGH assay HE2.4 | | | | |
| C | 461 | — | — | — |
| C + pAHE2 | 3,726 | 3,265 | 8.1 | — |
| C + pAHE2 + pBC331E2R | 433 | 0 | 0 | 100.0 |
| C + pAHE2 + pBG331E2RN | 3,815 | 3,354 | 8.3 | 0 |
| C + pAHE2 + pHE2-85 | 879 | 418 | 1.9 | 87.2 |
| C + pAHE2 + pHE2-123 | 422 | 0 | 0 | 100.0 |
| hGH assay HE2.5 | | | | |
| C | 513 | — | — | — |
| C + pAHE2 | 2,760 | 2,247 | 5.4 | — |
| C + pAHE2 + pBG331E2R | 549 | 36 | 1.1 | 98.4 |
| C + pAHE2 + pBG331E2RN | 2,405 | 1,892 | 4.7 | 15.8 |
| C + pAHE2 + pHE2-85 | 1,016 | 503 | 2.0 | 77.6 |
| C + pAHE2 + pHE2-123 | 488 | 0 | 0 | 100.0 |

Ratio of Repressor to trans-activator = 4:1
Dashes indicate not applicable.

We observed a 5 to 8-fold level of trans-activation by full-length HPV16 E2 protein. This was approximately 10-fold lower than the level of trans-activation shown by full-length BPV1 E2 protein. To compensate for the lower level of trans-activation, we used expression plasmid pBG331 for the HPV repression assay plasmid constructs. Plasmid pBG331 has a stronger promoter and therefore presumably expresses higher levels of E2 protein than pXB101, which we used for plasmid constructs in the earlier BPV E2 repression assays described in Example 6.

As expected, the 249 amino acid BPV1 E2 repressor (positive control) completely repressed trans-activation by the full-length HPV16 E2 protein, and the dimerization-defective BPV1E2RN analogue (negative control) showed negligible repression. Also as expected, the C-terminal 85 and 123 amino acids of HPV16 E2 protein functioned as repressors. The 85 amino acid HPV16 E2 protein fragment gave 87.2 and 77.6% repression, while the 123 amino acid HPV16 E2 protein fragment gave 100% repression in both assays. We believe that these HPV E2 repressors would maintain their repression activity upon introduction of mutations that destroy DNA binding without inhibiting dimerization. Examples of such mutations are cysteine to arginine at position 300 in HVP16 E2 (which corresponds to position 340 in BPV1 E2), and arginine to leucine at position 304 (which corresponds to position 344 in BPV1 E2).

EXAMPLE 8

Cellular Uptake of E2 Repressor Proteins

The E2 repressor proteins are not taken into cells at detectable levels. Thus, to deliver an E2 repressor protein into cells, we fused it to tat, a protein which naturally enters cells. Tat is a small, basic protein encoded by human immunodeficiency virus type I ("HIV-I"). It binds to the cell surface and gains entry by non-specific endocytosis in all cell types so far tested. Uptake of more than 10 million tat molecules per cell have been observed. E2 repressors can be linked to tat by expression of a recombinant fusion protein in transformed host cells or by chemical cross-linking of the two proteins. We have produced a tat-E2 repressor fusion protein in E. coli by recombinant DNA techniques.

Figure 16:
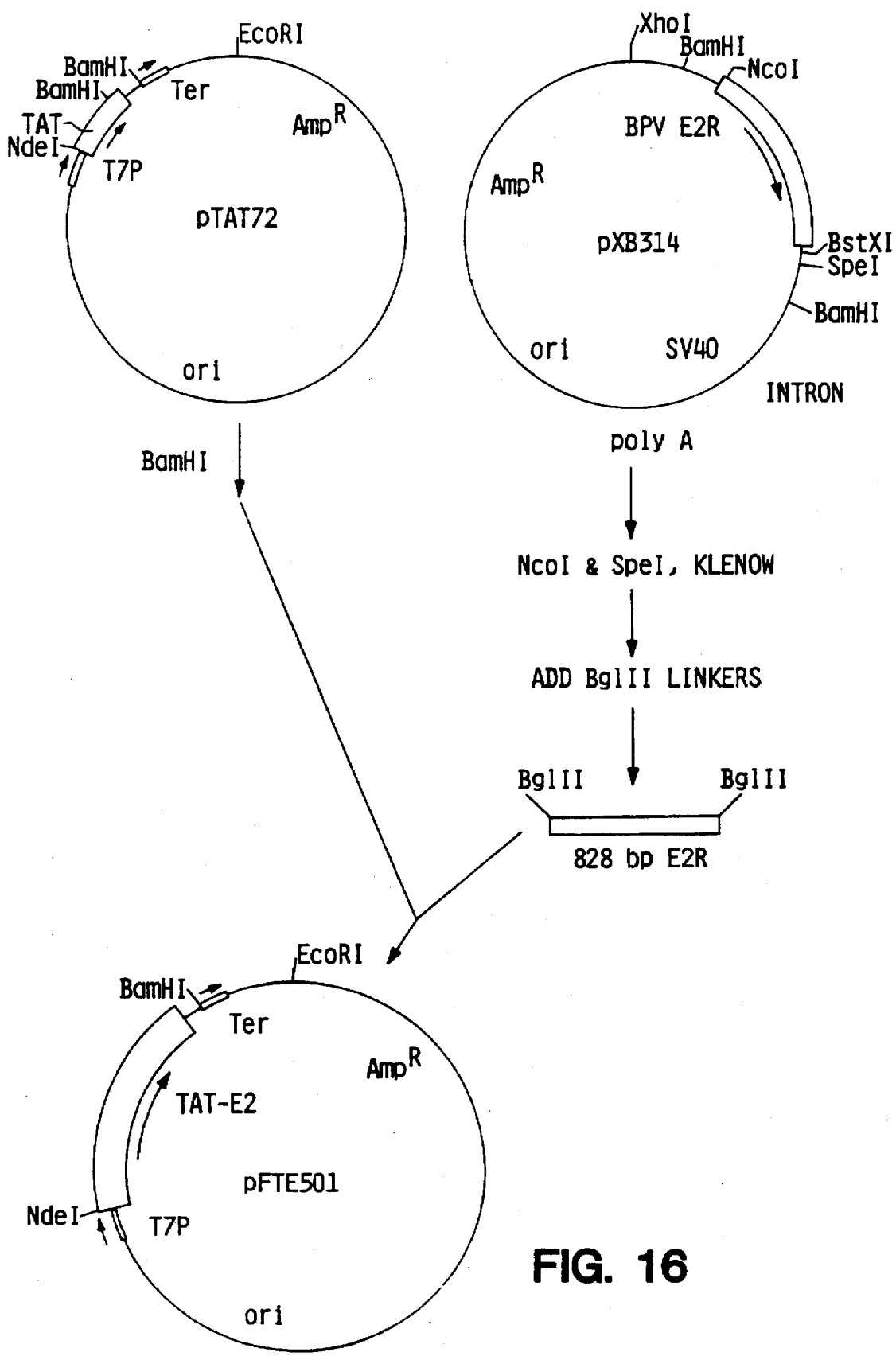
FIG. 16 schematically depicts the construction of plasmid pFTE501.

From plasmid pXB314 (Example 6; FIG. 9) we isolated the NcoI-SpeI DNA fragment encoding the 249 amino acid BPV1 E2 repressor, E2R. (NcoI cleaves at nucleotide 296, and SpeI cleaves at nucleotide 1118 of pXB314.) We blunted the ends of this fragment by DNA polymerase I Klenow treatment and added the BglII linker (New England Biolabs, cat. no. 1090) described in Example 6 (supra) and FIG. 9 (SEQ ID NO: 20 and SEQ ID NO: 21). We inserted this linker-bearing fragment into BamHI-cleaved (complete digestion) plasmid pTAT72. Plasmid pTAT72 is described in A. D. Frankel and C. O. Pabo, "Cellular Uptake Of The Tat Protein From Human Immunodeficiency Virus", Cell, 55, pp. 1189–94 (1988). In plasmid pTAT72 there is a BamHI cleavage site within the tat coding region, near its 3' end, and a second BamHI cleavage site slightly downstream of the tat gene. The BglII linker joined the tat and E2 coding sequences in frame to encode a fusion of the first 62 amino acids of tat protein followed by a serine residue and the last 249 amino acids of BPV1 E2 protein. We designated this bacterial expression plasmid pFTE501 (FIG. 16). We expressed the tat-E2R fusion protein in E. coli strain BL21 (DE3) as described in Studier et al., (supra). We purified the tat-E2R fusion protein from the insoluble fraction of E. coli according to the following procedure.

We pelleted the bacteria and resuspended them in ten packed cell volumes of 25 mM Tris-HCl (pH 7.5), 1 mM EDTA, 10 mM DTT, 1 mM PMSF, and lysed with 2 passages through a French press. We pelleted the membrane fraction by centrifugation at 10,000 rpm for 30 minutes in a Sorval SS-34 rotor, and then resuspended the membrane fraction in 6 M urea. We added solid guanidine-HCl to a final concentration of 6 M, and DTT to a concentration of 10 mM. After 30 minutes at 37° C., we clarified the solution by centrifugation at 10,000 rpm for 30 min. in a Sorval SS-34 rotor. We then loaded the sample onto an A.5 agarose gel filtration column in 6 M guanidine-HCl, 50 mM sodium phosphate (pH 5.4), 10 mM DTT and collected tat-E2R-containing fractions from the gel filtration column, according to the appearance of a band of the appropriate molecular size on Coomassie-stained SDS polyacrylamide electrophoresis gels. We loaded the gel filtration-purified sample onto a C18 reverse phase HPLC column and eluted with a gradient of 0–75% acetonitrile in 0.1% trifluoroacetic acid. We collected the tat-E2R fusion protein in a single peak with an apparent molecular weight of 40,000 Da.

We assayed cellular uptake of the tat-E2R fusion protein by indirect immunofluorescence in mouse fibroblast 3T3 cells. In the indirect immunofluorescence procedure our primary antibody was either a rabbit polyclonal antibody against BPV1 E2, generated by injection of the purified C-terminal 85 amino acids of E2, or a rabbit polyclonal antibody against tat protein, generated by injection of the purified 72 amino acid tat protein. We purified each of these 2 types of antibodies on an affinity column bearing the protein antigen against which the antibody was raised. Our secondary antibody was a rhodamine-conjugated goat anti-rabbit IgG (Cappel cat. no. 2212-0081).

We seeded the 3T3 cells into 4-chamber tissue culture chamber/slide (commercially available from LabTek). The following day we added tat-E2R fusion protein or unfused tat protein to the culture medium at 1 mg/ml, with 0.1 mM chloroquine to inhibit lysosomal protease activity. Six hours later we observed immunofluorescence according to the following procedure.

We removed the culture medium and washed the cells twice with phosphate buffered saline ("PBS"). We fixed the cells by treatment with 3.5% formaldehyde at room temperature, and permeabilized the cells by treatment with a solution of 0.2% Triton X-100, 2% bovine serum albumin ("BSA") in PBS containing 1 mM MgCl$_2$ and 0.1 mM CaCl, which solution is designated PBS+. We blocked the cells by treatment with whole goat serum (Cappel cat. no. 5006-1380) diluted 1:30 with PBS+ containing 2% BSA, for 1 hour at 4° C. We added primary antibody at a 1:100 dilution in PBS+ containing 2% BSA for 1 hour at 4° C., and then we added secondary antibody at a 1:100 dilution in 0.2% Tween-20, 2% BSA, in PBS+ for 30 minutes at 4° C. We washed the slides with 0.2% Tween-20, 2% BSA in PBS+, and then mounted in 50% glycerol in PBS. For viewing slide preparations, we used a fluorescent microscope with a rhodamine filter.

With the tat antibody in the above procedure, we observed intense internal fluorescence in cells exposed to tat-E2R protein, and in positive control cells exposed to non-fused tat protein. The E2 antibody gave intracellular fluorescence in cells exposed to the tat-E2R fusion protein, but not in cells exposed to unfused tat protein. No internal fluorescence appeared in negative controls that were not exposed to the tat-E2R fusion protein or the unfused tat protein. In additional experimental controls, neither antibody resulted in significant intracellular fluorescence in cells to which an E2 repressor alone was added. The intensity and subcellular location of fluorescence was similar whether the tat protein or the tat-E2R fusion protein was added to the cells. This indicates that the tat-E2R fusion protein entered the cells as efficiently as tat protein. These results indicate that the antibodies were specific for their respective proteins, and that the tat protein can deliver the E2R protein into animal cells. An indication of the efficiency of the tat-induced uptake is that the intracellular fluorescence was far more intense when tat-E2R was added to cells than when the tat-E2R or E2R gene constructs were expressed in transfected cells. We have obtained similar results in tests with other forms of tat and shorter forms of E2 repressors.

Microorganisms and recombinant DNA molecules prepared by the processes of this invention are exemplified by cultures deposited in the In Vitro International, Inc. culture collection ("IVI"), in Linthicum, Md. on Jan. 18, 1991 and identified as:

314: E. coli DH5/pXB314
337L: E. coli DH5/pEC337L
339M: E. coli DH5/pEC339M
340F: E. coli DH5/pEC340F
340R: E. coli DH5/pEC340R
340Y: E. coli DH5/pEC340Y
344L: E. coli DH5/pEC344L.

These cultures were assigned accession numbers IVI 10262, IVI 10263, IVI 10264, IVI 10265, IVI 10266, IVI 10267 and IVI 10268, respectively. These cultures were subsequently transferred from IVI to the American Type Culture Collection ("ATCC") in Rockville, Md., on Jun. 20, 1991. They were assigned ATCC accession numbers 68740, 68735, 68736, 68737, 68738, 68739 and 68740, respectively.

Microorganisms and recombinant DNA molecules prepared by the processes of this invention are further exemplified by cultures deposited in the American Type Culture Collection, Rockville, Md. on Jan. 24, 1992 and identified as:

pHE2-123
pHE2-85
BL21(DE3)/pLYSS/pFTE501

These cultures were assigned ATCC numbers 68896, 68897 and 68898, respectively.

While we have hereinbefore described a number of embodiments of this invention, it is apparent that our basic constructions may be altered to provide other embodiments which utilize the processes and products of this invention. Therefore, it will be appreciated that the scope of this invention is to be defined by the claims appended hereto, rather than by the specific embodiments which have been presented hereinbefore by way of example.

In the following "Sequence Listing", we have provided nucleotide sequence and amino acid sequence information for the SEQ ID Numbers referred to in this application. It should be noted that SEQ ID Numbers 2, 4, 6, 8, 10, 12, 14, 16, 23, 25 and 27 repeat the amino acid sequences listed with the nucleotide sequences of SEQ ID Numbers 1, 3, 5, 7, 9, 11, 13, 15, 22, 24 and 26, respectively.

We claim:

1. A method for isolating mutations yielding E2 homologous polypeptides that repress trans-activation by native E2 proteins comprising the steps of:
   a) producing a population of mutant DNA fragments by mutagenizing a DNA fragment encoding the amino acids of the native minimal DNA binding domain of a papillomavirus E2 protein;
   b) operatively linking said population of DNA fragments to expression control sequences;
   c) inserting said population of DNA fragments operatively linked to expression control sequences into a vector;
   d) transforming a unicellular host with said vector, said host comprising a full-length native E2 gene operatively linked to expression control sequences and a reporter gene whose transcription is activated by dimers comprising full-length native E2 proteins;
   e) screening for clones of transformed hosts that do not display E2 trans-activation;
   f) testing E2 homologous polypeptides from said clones for their ability to dimerize with themselves;
   g) testing said E2 homologous polypeptides for their ability to bind to E2 DNA binding sites;
   h) testing said E2 homologous polypeptides for their ability to repress transcriptional activation by full-length native E2 protein in a eukaryotic cell.

* * * * *